United States Patent [19]
Regnier et al.

[11] Patent Number: 5,958,202
[45] Date of Patent: Sep. 28, 1999

[54] CAPILLARY ELECTROPHORESIS ENZYME IMMUNOASSAY

[75] Inventors: Fred E. Regnier, West Lafayette, Ind.; Xian-Wei Yao; Todd A. Taylor, both of Framingham, Mass.; Martin Fuchs, Uxbridge, Mass.; Dieter Schmalzing, Cambridge, Mass.; Lance Koutny, Milton, Mass.; Wassim Nashabeh, Foster City, Calif.

[73] Assignee: PerSeptive Biosystems, Inc., Framingham, Mass.

[21] Appl. No.: 08/792,933

[22] Filed: Jan. 22, 1997

Related U.S. Application Data

[63] Continuation-in-part of application No. 08/386,224, Feb. 9, 1995, Pat. No. 5,810,985, which is a continuation of application No. 07/944,846, Sep. 14, 1992, abandoned.

[51] Int. Cl.$^6$ .......................... G01N 27/26; G01N 33/53; G01N 33/561; C12Q 1/68
[52] U.S. Cl. .............................. 204/451; 204/601; 435/6; 435/7.7; 435/7.92; 436/516
[58] Field of Search ...................................... 204/451, 455, 204/452, 461, 601, 605, 603, 612, 606; 435/4, 7.7, 6, 7.91, 7.92, 7.9; 436/515, 516

[56] References Cited

U.S. PATENT DOCUMENTS

| | | | |
|---|---|---|---|
| 4,181,589 | 1/1980 | Brooks | 435/173.9 |
| 4,288,425 | 9/1981 | Lee et al. | 436/516 |
| 4,312,727 | 1/1982 | Shainoff | 204/469 |

(List continued on next page.)

FOREIGN PATENT DOCUMENTS

| | | |
|---|---|---|
| 2 040 3132 | 8/1980 | United Kingdom . |
| WO 91/06850 | 5/1991 | WIPO . |
| WO 94/07132 | 3/1994 | WIPO . |
| WO 95/20161 | 7/1995 | WIPO . |
| WO 97/22825 | 6/1997 | WIPO . |

OTHER PUBLICATIONS

Schmalzing et al. (1995), "Solution–Phase Immunoassay for Determination of Cortisol in Serum by Capillary Electrophoresis," 41 *Clin. Chem.* 9:1403–1406, month unknown.

Caplus abstract of Masanari Imamura ("A new quantitative determination of antigen by capilary agarose immunoelectrophoresis", Toho Igakkai Zasshi, 1977, 24(4), 612–15), month unavailable.

Masanari Imamura ("A new quantitative detrmination of antigen by capillary agarose imunoelectrophoresis", Toho Igakkai Zasshi, 1977, 24(4), 612–15), month uavailable.

Aebersold et al., "Analysis of Dilute Peptide Samples by Capillary Zone Electrophoresis," *J. Chromatogr.*, 516:79–88 (1990), month unavailable.

Chien et al., "Field Amplified Sample Injection in High––Performance Capillary Electrophoresis," *J. Chromatogr.*, 559:141–152 (1991), month unavailable.

(List continued on next page.)

*Primary Examiner*—Robert Warden
*Assistant Examiner*—Alex Noguerola
*Attorney, Agent, or Firm*—Testa, Hurwitz & Thibeault, LLP

[57] ABSTRACT

Disclosed are methods and apparatus for performing highly sensitive enzyme-amplified assays using channel electrophoresis of an enzyme having a biorecognition moiety. Combining a binding reaction of an analyte and an enzyme having a biorecognition moiety, and an electrophoretic separation which uses enzyme-amplified detection methodology, assay methods and apparatus are provided that offer simplicity, quantitative sensitivity and rapid analysis. Also disclosed are highly sensitive catalytically-amplified assays using a capillary electrophoresis format in which the binding reaction prior to electrophoresis is heterogeneous or homogeneous, and direct or competitive. The methods and apparatus for conducting sensitive automated catalytically-amplified assays using electrophoresis may be conducted in a microscale format.

29 Claims, 23 Drawing Sheets

U.S. PATENT DOCUMENTS

| | | | |
|---|---|---|---|
| 4,753,875 | 6/1988 | Ryan | 435/7.4 |
| 4,849,353 | 7/1989 | Harpel | 435/7.4 |
| 4,865,706 | 9/1989 | Karger et al. | 427/8 |
| 4,865,707 | 9/1989 | Karger et al. | 204/453 |
| 5,045,172 | 9/1991 | Guzman | 204/452 |
| 5,055,415 | 10/1991 | Imai et al. | 436/516 |
| 5,061,361 | 10/1991 | Gordon | 204/452 |
| 5,084,150 | 1/1992 | Karger et al. | 204/453 |
| 5,089,099 | 2/1992 | Chien et al. | 204/453 |
| 5,116,471 | 5/1992 | Chien et al. | 204/453 |
| 5,122,248 | 6/1992 | Karger et al. | 204/453 |
| 5,137,609 | 8/1992 | Manian et al. | 204/452 |
| 5,145,567 | 9/1992 | Hsieh | 204/452 |
| 5,194,133 | 3/1993 | Clark et al. | 204/608 |
| 5,264,095 | 11/1993 | Hsieh | 204/452 |
| 5,500,071 | 3/1996 | Kaltenbach et al. | 156/272.8 |
| 5,536,382 | 7/1996 | Sunzeri | 204/451 |
| 5,645,702 | 7/1997 | Witt et al. | 204/501 |
| 5,646,048 | 7/1997 | Templin et al. | 436/180 |
| 5,650,846 | 7/1997 | Yin et al. | 356/318 |

OTHER PUBLICATIONS

Nashabeh et al., "Capillary Zone Electrophoresis of Proteins with Hydrophilic Fused–Silica Capillaries," *J. Chromatogr.*, 599:367–383 (1991), month unavailable.

Emmer et al., "Improved Capillary Zone Electrophoretic Separation of Basic Proteins, Using a Fluorosurfactant Buffer Additive," *J. Chromatogr.*, 547:544–550 (1991), month unavailable.

Bruin et al., "Capillary Zone Electrophoretic Separations of Proteins in Polyethylene Glycol–Modified Capillaries," *J. Chromatogr.*, 471:429–436 (1989), month unavailable.

Jorgenson et al., "Zone Electrophoresis in Open–Tubular Glass Capillaries," *Analytical Chemistry*, 53:1298–550 (1981), month unavailable.

Lauer et al., "Capillary Zone Electrophoresis of Proteins in Untreated Fused Silica Tubing," *Analytical Chemistry*, 58:166–170 (1986), month unavailable.

Nielsen et al., "Capillary Zone Electrophoresis of Insulin and Growth Hormone," *Analytical Biochemistry*, 177:20–26 (1989), month unavailable.

Schlabach et al., "Rapid Assessment of Isoenzymes by High–Performance Liquid Chromatogrphy," *Clinical Chemistry*, 24:1351–1360 (1978), month unavailable.

Snyder, "Reaction Colorimeters as Detectors in High–Performance Liquid Chromatography," *J. Chromatogr.*, 125;287–306 (1976), month unavailable.

Towns et al., "Synthesis and Evaluation of Epoxy Polymer Coatings for the Analysis of Proteins by Capillary Zone Electrophoresis," *J. Chromatogr.*, 599:227–237 (1992), month unavailable.

Wu et al., "High–Performance Capillary Isoelectric Focusing with a Concentration Gradient Detector," *Anal. Chem.*, 64:219–224 (1992), month unavailable.

Yoshida, "Hemolytic Anemia and G6PD Deficiency," *Science*, 179:532–537 (1973), month unavailable.

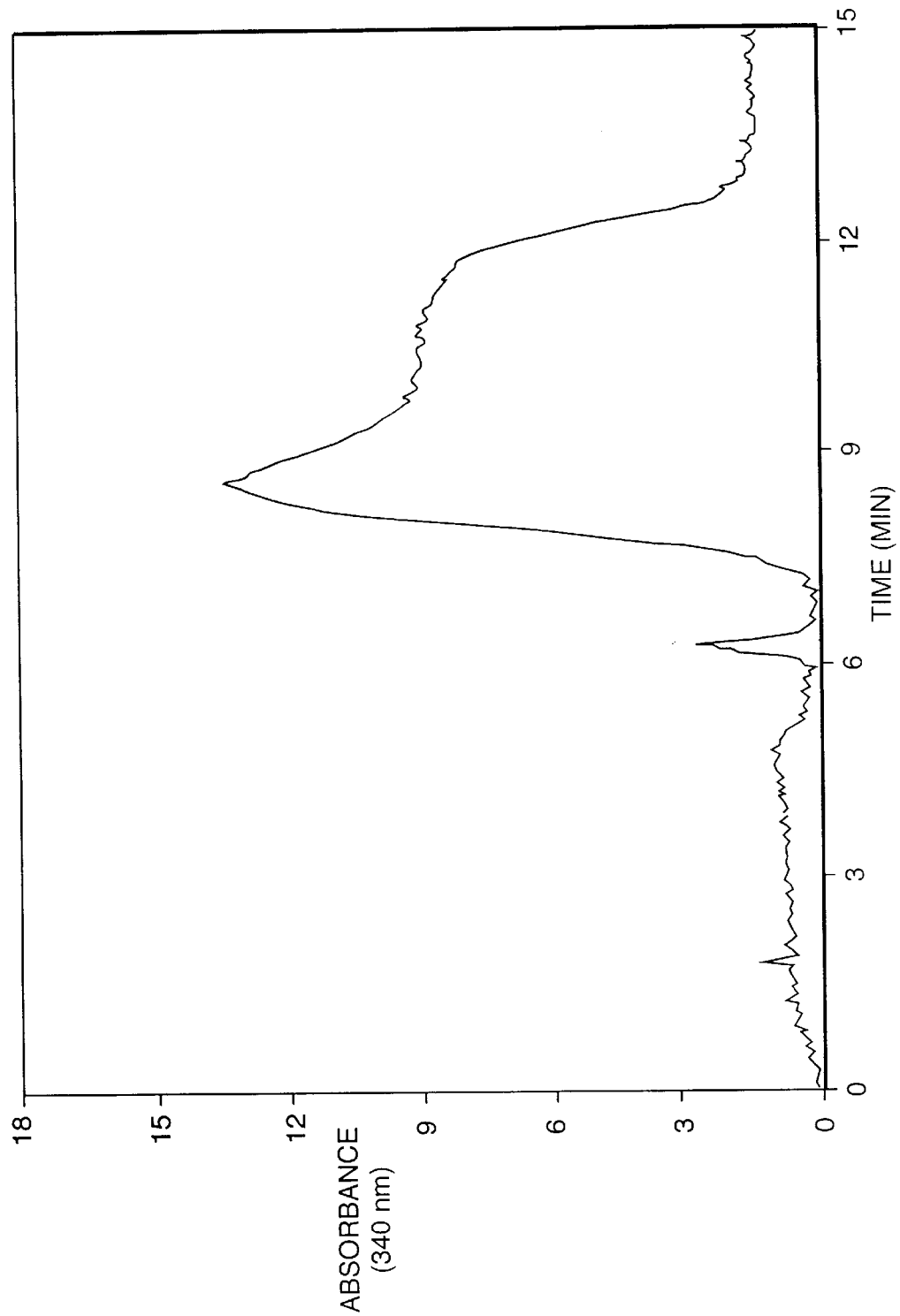

CAPILLARY ELECTROPHORESIS ENZYME IMMUNOASSAY

This is a continuation-in-part of U.S. patent application Ser. No. 08/386,224, filed on Feb. 9, 1995, which, in turn, is a continuation of U.S. patent application Ser. No. 07/944,846, filed on Sep. 14, 1992, now abandoned.

FIELD OF THE INVENTION

The invention relates in general to techniques for analysis of chemical species, and in particular to analyses involving electrokinetic separation.

BACKGROUND OF THE INVENTION

Capillary electrophoresis is a well-known procedure for separation of chemical components. A sample solution containing molecules to be separated is placed in a length of capillary tubing containing an electrophoretic medium. Upon application of an electric field across the capillary, different components within the sample migrate at distinct rates towards the oppositely charged end of the capillary dependent upon their relative electrophoretic mobilities in the electrophoretic medium. Due to the varying electromigratory rates, the sample components become increasingly separated into distinct zones or groups as they progress along the capillary. At some position along the capillary, the components of the sample are detected.

Electrophoresis has been applied to the separation of charged materials such as proteins, nucleic acids, and cells. These separations depend upon differences in charge density, molecular size, and partitioning or complexation with a mobile phase additive. U.S. Pat. No. 5,061,361 relates to a capillary zone electrophoresis system in which a nanoliter volume of sample is introduced into the capillary tube, and an electric field is imposed on the system to effect separation of the charged components. After migration along the length of the tube, the sample components are detected via ultra-violet absorbance. U.S. Pat. No. 5,084,150 relates to an electrokinetic method of separation in which the surface of moving charged colloidal particles is treated so as to interact selectively with the sample molecules to be separated. An electric field is imposed on a capillary tube containing the colloidal particles and the sample to achieve separation. U.S. Pat. No. 5,045,172 relates to a capillary electrophoresis apparatus in which electrodes are attached at each end of a capillary tube, and a detector is coupled to the tube. U.S. Pat. No. 4,181,589 relates to a method for separating biological cells using an electric field. The above-described U.S. patents are hereby incorporated by reference.

Various types of assays are used as clinical diagnostics. Immunoassays of various formats widely are used in clinical diagnosis to measure analytes in body fluids. Immunoassays also are used for the sensitive and specific measurement of analytes in complex mixtures in research, industrial and environmental applications. For example, an enzyme linked immunosorbent assay ("ELISA") has been used to determine levels of cytokines, Thyroid-Stimulating Hormone ("TSH") and other analytes in serum and other biological samples. Engvall, *Methods in Enzymology*, 70:419 (1980); Schurrs and VanWeeman, *J. Immunoassay*, 1:229 (1980); and Scharpe, et al., *Clin. Chem.*, 22:733 (1976) are general references to enzyme immunoassay techniques and are herein incorporated by reference in their entirety.

Patent Cooperation Treaty ("PCT") publications WO 93/220553 and WO 93/22054, and U.S. Pat. No. 5,304,487, herein incorporated by reference, describe various types of assays performed in microscale analytical devices. Devices for detecting the presence of a preselected analyte in a fluid sample or for analyzing a fluid cell containing a sample are disclosed. The devices typically are made of a solid substrate that is microfabricated to have a sample inlet port and a mesoscale flow system. Other embodiments have various flow restriction designs. The solid substrate may be a few millimeters thick and about 0.2 to 2.0 cm square. The flow channel typically on the order of 0.1 $\mu$m to 500 $\mu$m. The devices are used in a wide range of automated, sensitive and rapid tests using various flow inducing means.

Immunoassays using electrophoretic separation of free and bound antigen have been explored. Assays using capillary electrophoresis have provided rapid separation and accurate quantitation. Moreover, the microvolume scale of capillary electrophoresis reduces the amount of sample and reagents required, as well as decreasing the amount of waste generated. However, many assays require analyte quantitation to be at levels of $10^{-10}$ to $10^{-12}$ Molar. Given these low concentrations of analyte, even laser induced fluorescence detection coupled with capillary electrophoresis may not be sufficient for the detection of an analyte. Overall, sensitivity, speed and cost are important factors to be considered in designing and conducting an immunoassay.

SUMMARY OF THE INVENTION

The invention encompasses methods of analysis of an analyte in a sample, and is based on the discovery that analyte determination may be performed rapidly using capillary electrophoresis on exceedingly small amounts of sample by performing enzyme amplification with a compound having a biorecognition moiety in a capillary electrophoresis format.

One object of the invention is to provide methods and apparatus for performing highly sensitive enzyme-amplified assays using capillary electrophoresis of an enzyme having a biorecognition moiety. Combining a binding reaction of an analyte with an enzyme having a biorecognition moiety and an electrophoretic separation which uses enzyme-amplified detection methodology, assay methods and apparatus are provided that offer simplicity, quantitative sensitivity and rapid analysis. Another object of the invention is to provide highly sensitive enzyme-amplified assays using a capillary electrophoresis format in which the binding reaction prior to electrophoresis is heterogeneous or homogeneous. Another object of the invention is to provide enzyme-amplified immunoassays using capillary electrophoresis. Yet another object of the invention is to provide methods and microscale apparatus for conducting sensitive automated enzyme-amplified assays using electrophoresis.

Unlike traditional electrophoresis, electrophoresis utilized according to the invention exploits inherent or induced differences in electrophoretic velocities of a detectable product and/or a competitor (the amount of competitor being proportional to an analyte of interest), and a reactant in a given electrophoretic medium in order to mix and separate these components. The electrophoretic mixing of chemical species confers a special advantage over the traditional methods in the field of chemical analysis; i.e., electrophoretic mixing of competitor and reactant is performed without substantial dilution of the chemical species contained within the zones. Under the influence of an applied potential and a chosen electrophoretic medium, a chemical species may possess a distinct electrophoretic mobility which will allow it to electrophorese essentially independently of the bulk solution. Thus, a zone of competitor and a zone of reactant, which move in the electric field with different electrophoretic mobilities, may become interpenetrated without the volumetric addition of the bulk solutions. In addition, electrophoretic mixing does not require turbulent flow to fully merge two zones. Thus, the inventive methods of chemical analysis are simpler and more efficient than conventional chemical analysis methods. At high potentials, e.g., 300–2000 volts/cm, full electrophoretic mixing of two zones can often be achieved in milliseconds.

The electrophoretic separation capability of methods of the invention allows for separation of chemical species prior to as well as after the chemical reaction that produces detectable product. This powerful ability confers many advantages which are absent in previous methods of chemical analysis. One of skill in the art may manipulate a range of experimental parameters of the inventive methods which allow control of the engagement and disengagement of the competitor and reactant zones, as well as selective monitoring of the detectable product. As a result, analysis methods of the invention encompass any chemical reaction for the analysis of samples containing single and multiple analytes. The reactions conducted using electrophoretic mixing are catalyzed reactions which provide amplification of the catalytic chemical species thereby permitting low detection levels readily to be achieved.

Methods of the invention relate to a novel concept of performing an assay in which a first reactant and a sample containing a competitor are brought into contact electrophoretically and a chemical reaction is allowed to occur to form or deplete a detectable product. The sample typically is an aliquot of a reaction solution where an analyte of interest and a competitor underwent a competitive or direct reaction. That is, the competitor has a biorecognition portion that participates in a binding reaction either directly with the analyte or in competition with the analyte. After the binding reaction, an aliquot of reaction solution is introduced to a channel and subjected to an electric potential. Subsequently, a second reactant portion of the competitor catalyzes a reaction with the first reactant in the channel to form or deplete a detectable product. The competitor typically is an enzyme linked to an antigen, antibody, DNA or PNA.

In embodiments of the invention, the first reactant and the sample are introduced into a channel that contains an electrophoretic medium. An electric potential sufficient to mix the first reactant and the competitor and to migrate the detectable product along the channel is imposed along the length of the channel. In more preferred embodiments, the detectable product is detected, quantitated and the amount of analyte is indirectly determined. The invention also features an analytical device useful in conducting methods of the invention. In its simplest form, the analytical device has a channel which contains an electrophoretic medium and a first reactant for reacting with a second reactant portion of a competitor to form or deplete a detectable product. The first reactant may be spaced apart from the competitor so that electrophoretic movement permits the first reactant and the second reactant portion of the competitor to react to form or deplete the detectable product. In other embodiments of the invention, the analytical device may have an electrophoresis apparatus, a detector and/or a quantitator. In certain embodiments of the invention, the channel is a capillary, is part of a capillary array, or defines a flow system present on a chip such as a microchip. In another embodiment of the invention, the analytical device has a sample injection zone and a channel. The sample injection zone may be a well in a chip. The sample injection zone typically is the location of a binding reaction. The analytical device of this embodiment also has an electrophoretic medium and a first reactant that are introduced into the channel. Many features and concepts present in the device described above are present in these embodiments of the invention such as an electrophoresis apparatus, a detector and/or a quantitator. In a preferred embodiment, the device is a chip such as a microchip. The chip includes at least a sample injection zone and a channel. However, multiple sample injection zones and channels are contemplated by the invention.

Advantages of the invention include the following. Methods of the invention allow for rapid analysis of one or more analytes in a sample. Because the volume of the capillary used in the analysis is small, e.g., 10–100 nanoliters/cm, the volume of sample which is necessary for analysis according to the invention is exceedingly small; e.g., as little as 1 nanoliter may be consumed per minute of analysis in very small capillaries, and thus the invention allows for less expensive analysis of a sample. Multiple analytes in a sample may be analyzed concurrently according to the invention, and only one product may be determined, or several products if desired.

Another advantage of the methods of the invention is that no mechanical pump is necessary to propel the chemical components through the capillary system. The components are transported through the system electro-osmotically, i.e., by virtue of their electrical charge and mobility in an electric field. Thus, components which are highly charged will be transported quickly through the capillary towards the oppositely charged pole; similarly, relatively uncharged components will move slowly.

The system can be designed to be self-flushing such that between runs there is a net convective flow of buffer towards one pole of the capillary due to electro-osmosis. Electro-osmosis is a property which is created by a net negative or positive charge of ions on the walls of the capillary. These ions move when the electric potential is applied to the capillary, and drag the liquid in the capillary along with them. There is a diminishing effect of this drag; i.e., the liquid closest to the inner wall of the capillary is dragged faster than liquid in the center of the capillary. One effect of electro-osmosis is that the capillary need not be flushed mechanically between runs because the electrophoretic system continuously pumps the buffer through the capillary at a rate of 1–70 nL/min. The electro-osmotic effect may be varied by varying the charge on the capillary wall, or by varying the viscosity of the polymers which coat the inner wall of the capillary, or by the viscosity of the solution in the capillary.

The control of the parameters of the methods described herein, e.g., sample volume, reactant volume, electric potential, capillary length, electro-osmotic flow, etc., confers on one of skill in the art exquisite control over the chemical reaction itself, and thus of the sensitivity of the system.

Another advantage of the methods of the invention is that the time during which the chemical components are allowed to interact may be controlled by increasing or decreasing the electric potential. For example, if a chemical reaction occurs only slowly, the potential may be decreased or turned off in order to allow the chemical components more time to interact and form or consume product. Alternatively, if a chemical reaction occurs quickly, the potential may be increased so that product is separated as it is formed or depleted. This shortens the time required for analysis significantly.

Analysis of a sample according to the invention may be performed repeatedly and routinely after the initial profile of the chemical reaction has been produced. A test for a specific analyte in a sample may be performed routinely on hundreds of samples once it is known when the product peak will pass the detector relative to other components in the capillary, i.e., reactant, unreacted analyte, or contaminants. In addition, multiple analytes may be analyzed concurrently according to the invention. More complex reactions are also analyzable according to the invention. For example, competitor (a) may catalyze the formation of product (a); competitor (b) forms product (b); and competitor (c) forms product (a). If competitors (a) and (c) possess different electrophoretic mobilities in an electric field, then analysis of product (a) for each of competitors (a) and (c) is easily accomplished according to the invention. In addition, where products (a) and (b) possess different properties for detection, these products are also easily analyzed. Thus, multiple reactions which produce the same product and multiple reactions which produce different products may be analyzed according to the invention.

The invention may encompass the analysis of many different analytes using different reactants. Examples of competitors or reactants include but are not limited to the following. Where the competitor has an enzyme, the reactant may be a substrate for the enzyme. Conversely, where the competitor has a substrate portion, the reactant may be an enzyme capable of converting the substrate to a product. The competitor or reactant may also include any substance which may be converted to a product stoichiometrically where quantitation of an analyte is desired, or nonstoichiometrically where simple detection of the analyte is desired. Products detectable according to the invention include any substance which possesses a property detectable by any conventional means, e.g. heat, electromagnetic energy, radiation, or fluorescence. Conventional means of detection are used according to the invention and are described herein.

Further advantages of the invention include the simplicity, speed and sensitivity achieved for conducting an assay of an analyte using enzyme-amplified detection methodology in conjunction with a competitor having a biorecognition moiety. Assays of the invention are applicable to a wide variety of diagnostic tests including the routine screening and monitoring of the health of humans and animals, as well as environmental monitoring and industrial processing. On-line amplification and quantitation of an enzyme having a biorecognition moiety from complex mixtures such as serum are performed in a sensitive electrophoresis format. Specifically, using a capillary electrophoresis format in conjunction with a enzyme amplification, assays routinely can be conducted in 15 minutes or less. The method involves less manual processing and can be fully automated. Detection sensitivity of $10^{-10}$ Molar and lower readily is achieved. Moreover, the channel electrophoresis format provides control of the amplification and detection processes for easy assay optimization and flexibility of assay design. In addition, multichannel devices can dramatically increase throughput.

These and other objects, features and advantages of the invention will be apparent from the drawings, description and claims which follow.

BRIEF DESCRIPTION OF THE DRAWINGS

FIG. 6(a) is the resulting electropherogram of a heterogeneous competitive or direct reaction. FIG. 6(b) is the resulting electropherogram of a homogeneous reaction.

FIGS. 14(a) and 14(b) are electropherograms showing the accumulated peak resulting from (a) NADPH accumulated before electrophoresis was initiated, and (b) NADPH accumulated just before G-6-PDH passed the detection window.

DETAILED DESCRIPTION OF THE INVENTION

Figure 1:
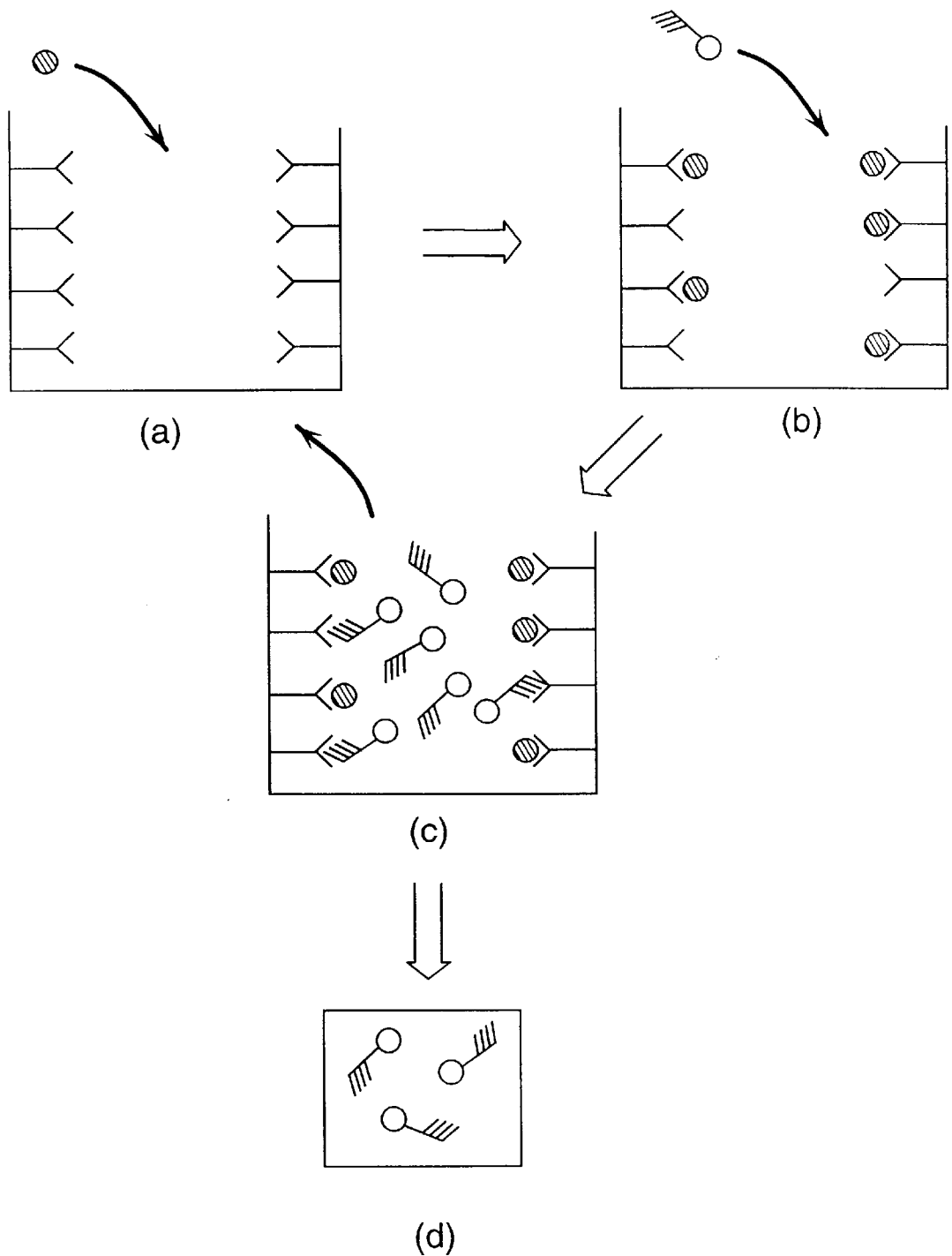
FIGS. 1: (a)–(d) are schematic representations of the steps of a heterogeneous competitive reaction that is part of a preferred embodiment of the invention in which the solid circles represent an analyte to be quantitated, the "Y's" are immobilized antibodies, and the open circles with hashed tails are competitors.

It should be understood that as used herein the term "first reactant" is used interchangeably with the term "reactant." The first reactant may be an enzyme substrate.

The term "competitor" is a compound that has a second reactant portion and a biorecognition portion. The second reactant portion and biorecognition portion of the competitor may be directly linked or independently attached through a linker or other entity. The second reactant portion typically is an enzyme but can be another entity that catalyzes a reaction with a first reactant to form or deplete a detectable product. The biorecognition portion is a moiety that has the ability to react, associate or bind with any analyte of interest, and particularly antigens and biomolecules, such as an antibody, a DNA and an RNA. Biorecognition portions include, but are not limited to, affinity ligands, antibodies, antigens, enzymes and their substrates, peptides, peptide nucleic acids, oligonucleotides, deoxyribonucleic acids, ribonucleic acids, biotins and their target binding complexes, lectins and their target carbohydrate binding complexes, and cellular receptor binding proteins and their complementary or target binding products including co-factors, agonists, antagonists, inhibitors and stimulators. Biorecognition portions also may be receptors that are able to associate with organelles, organisms and tissue slices. References to biorecognition techniques and species are Morgan et al., *Clin. Chem.,* 42:193–209 (1996) and Mattos et al., *Nature Biotechnol,* 14:595–599 (1996), which are incorporated by reference herein. In preferred embodiments, competitors are enzyme-labelled antigens, enzyme-labelled antibodies or enzymes labelled with a peptide nucleic acid ("PNA"). PCT publications WO 92/20702 and WO 92/20703 disclose syntheses and properties of PNAs and are herein incorporated by reference.

As used herein, the term "competitor" may refer to a compound called an "analyte" in certain applications, i.e., the introduction of a "competitor" into a channel or capillary may be equivalent to the introduction of an "analyte" into a channel or capillary. In other words, in certain embodiments of the invention, an "analyte" is introduced into a channel and may participate in a chemical reaction to produce a product. In other embodiments, a "competitor," such as an immunologically active species, is introduced into a channel and a second reactant portion of the competitor will react with a first reactant to form a detectable product. In certain aspects of the invention where a competitor is used, the amount of analyte indirectly will be determined by the amount of competitor introduced into the channel. In other aspects of the invention where a competitor is used, the amount of analyte indirectly will be determined by the amount of analyte-competitor complex present.

The term "product" often refers to a "detectable product" that is formed, e.g., by the interaction between the first reactant and the second reactant portion. The terms "capillary" and "channel" are often referred to interchangeably, except where specific reference is made to particular embodiments that entail a "capillary." The term "vessel" refers to any area, zone or location where intermingling of reagents or a reaction can occur. In preferred embodiments, a vessel is a contained area, zone or location made of a material that is inert to the reagents present in the vessel. Examples of vessels are, among others known to those skilled in the art, cups, beakers, flasks, test tubes, syringes, columns, capillaries, channels, microtiter plates and microwells.

The term "immobilized reactant" refers to any chemical species that remains in a fixed area and is capable of association with an analyte. The association between the immobilized reactant and the analyte may occur by various means known to those skilled in the art such that the analyte will remain in the fixed area of the immobilized reactant. The immobilized reactant may remain in a fixed area by a variety of means including, but not limited to, physical adsorption or chemical attachment. In preferred embodiments, the immobilized reactant is an immobilized antibody or an immobilized PNA.

The term "analyte-competitor complex" refers to a species that is formed by the association of an analyte and a competitor. The association can be by any means known to those skilled in the art that is related to the biorecognition portion of the competitor.

The invention relates to novel methods for determining the presence and/or concentration of an analyte in a sample by contacting the sample with a competitor having a biorecognition moiety and a second reactant portion, then placing an aliquot of the reaction solution into a capillary electrophoresis system to initiate a chemical reaction which converts a first reactant, e.g., an enzyme substrate, to a detectable product. Initiation of the chemical reaction depends upon the mixing of the competitor and the first reactant via electrophoretic migration or electro-osmotic flow, and detection of the product depends upon electrophoretic transport of the product to a detector.

The detection of product which is produced or depleted by the chemical reaction is an indication of the presence of the analyte. Where determination of the analyte is quantitative, the conversion of the first reactant to product or the depletion of product will be stoichiometric. For stoichiometric conversion of the first reactant to product, measurement of the product detected can be used to calculate the amount of analyte present in the sample. Methods of the invention thus allow for measurement of the presence of an analyte in a sample.

Capillary electrophoretic methods of the invention involve three phases for the determination of an analyte in a sample: mixing of a competitor and a first reactant; the chemical reaction itself; and detection of a species whose production or depletion is indicative of the presence, concentration, or quantity of an analyte of interest.

The time required to perform an assay according to the invention ($t_{assay}$) encompasses each of the following temporal phases: the time required for the electrophoretic mixing of the analyte and reactant ($t_{mix}$), the time in which the chemical reaction occurs ($t_{rxn}$), and the time needed to transport the detectable species to the detector ($t_{det}$):

$$t_{assay} = t_{mix} + t_{rxn} + t_{det} \tag{1}$$

The time window available to perform the mixing and reaction phases of the analysis in order to form the product which is ($t_{form}$) is generally limited to the time interval between the injection of the analyte and its passing by the detector:

$$t_{form} = \frac{lL}{(\mu_{em} + \mu_{eo})V} \tag{2}$$

where l is the effective length of the capillary measured from the point of injection to the point of detection, L is the total length of the capillary over which the potential, V, is applied, $\mu_{em}$ is the electrophoretic mobility of the analyte in the given electrophoretic medium, and $\mu_{eo}$ is the electro-osmotic flow of the capillary electrophoretic system.

1. Overview

Figure 2:
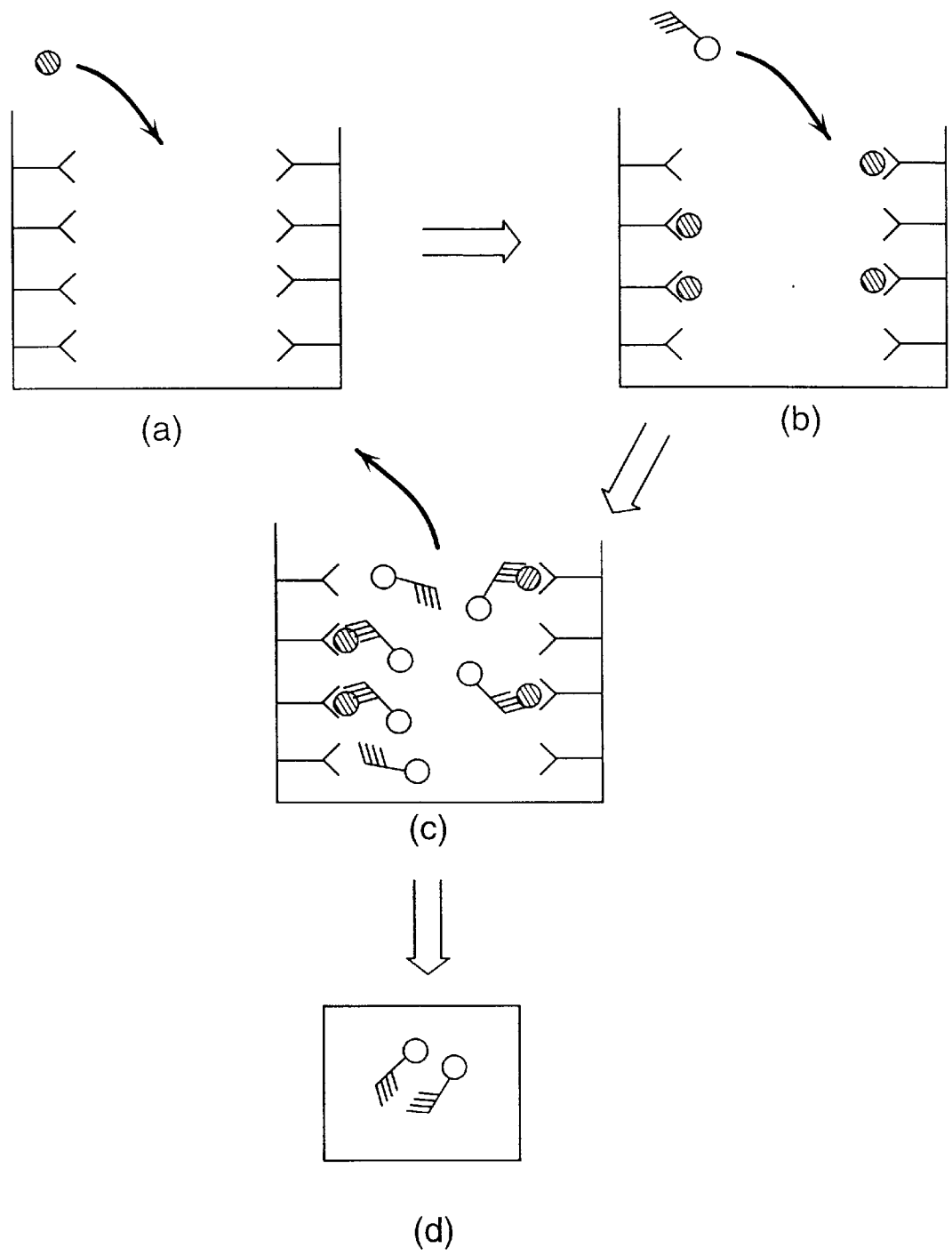
FIGS. 2: (a)–(d) are schematic representations of the steps of a heterogeneous direct reaction that is part of a preferred embodiment of the invention in which the solid circles represent an analyte to be quantitated, the "Y's" are immobilized antibodies, and the open circle with hashed tails are competitors.
Figure 3:
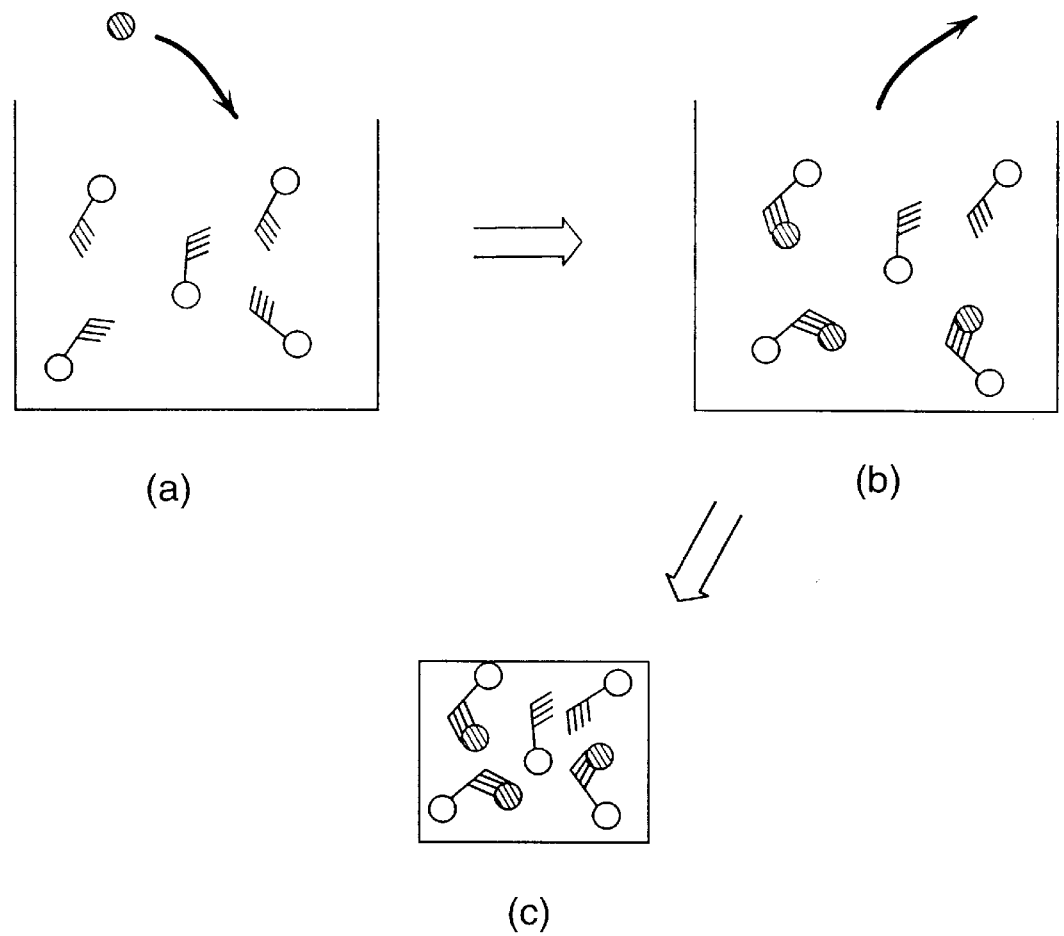
FIGS. 3: (a)–(b) are schematic representations of the steps of a homogeneous reaction that is part of a preferred embodiment of the invention in which the solid circles represent an analyte to be quantitated and the open circles with hashed tails are competitors. The compound having a solid circle overlapping a hashed tail portion of a competitor represents an analyte-competitor complex.

A brief overview of pre-electrophoretic reactions used in the practice of the invention is shown in FIGS. 1–3. FIG. 1 depicts a heterogeneous competitive reaction as part of a preferred assay method of the invention. In FIG. 1(a), immobilized antibodies, represented by the horizontal "Y's," are present in a vessel. The solid circle represents an analyte to be measured, such as an antigen. The analyte is contacted with the immobilized antibodies and binds to the immobilized antibodies as shown in FIG. 1(b). Subsequently, an excess of a competitor, represented by an open circle with a hashed tail, is added to the solution. The hashed tail portion represents the biorecognition portion of the competitor and the open circle represents the second reactant portion of the competitor. The second reactant portion typically is an enzyme. In FIG. 1, the competitor may be an enzyme labelled antigen so that the competitor competes with the analyte for binding sites on the immobilized antibodies (FIG. 1(c)). An excess of the competitor is used so that an aliquot (FIG. 1 (d)) removed from the vessel after completion of the competition reaction essentially will contain unbound competitor. However, because the reaction is a competition between the analyte and the competitor for immobilized antibody binding sites, there also may be unbound analyte present in the aliquot that is introduced into the channel for electrophoretic analysis. The amount of unbound analyte in the aliquot will be influenced by the reaction conditions and the binding constant of the chemical species.

The aliquot containing the unbound competitor (FIG. 1(d)) then is introduced to a channel containing a first reactant, typically an enzyme substrate. Electrophoretic motion is used to mix the competitor and the first reactant so that the second reactant portion of the competitor and the first reactant react to form a detectable product that is migrated along the channel past a detector. The detector detects the detectable product and if coupled to a quantitator such as a computer, the amount of detectable product can be automatically calculated.

The electrophoretic motion often is stopped for a period of time to permit the second reactant portion of the competitor to catalyze the production of a greater amount of detectable product. In this way, small undetectable amounts of competitor can be measured by the formation of large amounts of detectable product that can be accurately quantitated. In the heterogeneous competitive reaction shown in FIG. 1, the amount of unbound competitor subjected to channel electrophoresis enzyme amplification is directly proportional to the amount of detectable product formed. The amount of analyte in the original sample is directly proportional to the amount of unbound competitor. Thus, using these relationships, the amount of analyte can be calculated from the amount of detectable product formed.

In FIG. 2, an example of a heterogeneous direct reaction is shown as part of preferred assay methods of the invention. FIG. 2(a) shows the immobilized antibodies present in a vessel (like structures in FIGS. 1–3 will be represented similarly). An analyte is added that binds to the immobilized antibodies and after an appropriate period of time, an excess of competitor is added (FIG. 2(b)). In this example, the biorecognition portion of the competitor is able to recognize and bind to the analyte, forming a "sandwich-type" arrangement (FIG. 2c)). For example, the analyte may be an antigen and the competitor may be an enzyme labelled antibody. A common example of this type of reaction technique is ELISA. Subsequent to an incubation period, an aliquot of the reaction containing unbound competitor (FIG. 2(d)) is introduced into a channel containing a first reactant and an electrophoretic medium. Electrophoretic motion is used to mix the competitor and the first reactant and the process continues as described above with the second reactant portion of the competitor catalyzing a reaction with the first reactant to form a detectable product.

The heterogeneous direct reaction scheme depicted in FIG. 2 has a different relationship between the amount of competitor and the amount of analyte. Although the amount of detectable product formed still is proportional to the amount of unbound competitor introduced into the channel, the amount of analyte is inversely proportional to the amount of unbound competitor. That is, the more unbound competitor in the aliquot subjected to channel electrophoresis enzyme amplification, the less competitor that is bound to the analyte in the vessel which is directly proportional to the amount of analyte in the original sample. Again, using these relationships, the amount of analyte can be calculated from the amount of detectable product formed.

FIG. 3 depicts a homogeneous reaction scheme that forms part of the preferred assay methods of the invention. In a homogeneous reaction, no immobilized compounds are present in the initial binding reaction (FIG. 3(a)) or in the channel electrophoresis assay. The analyte and competitor may be any species that will bind to each other via the biorecognition moiety of the competitor. After sufficient time is allowed for association to occur between the analyte and an excess amount of the competitor (FIG. 3(b)), an aliquot containing the analyte-competitor complex and the excess competitor is introduced into the channel containing a first reactant.

Typically in a direct homogeneous reaction, a large excess of the competitor is used to drive the formation of the analyte-competitor complex to near completion so very little unbound analyte will be present in the aliquot subjected to electrophoretic analysis. On the other hand, in a competitive homogeneous reaction, the analyte and competitor are in a dynamic reversible binding interaction so that the analyte, competitor and analyte-competitor complex will be contained in the aliquot of reaction solution to be subjected to electrophoretic analysis. The amount of each species present at a given time is influenced by the reaction conditions and the binding constants of the species.

Subsequent to the introduction of the aliquot into the channel, electrophoretic motion is used to mix the chemical species in the aliquot with the first reactant. Upon application of an electric current along the channel, the competitor and the analyte-competitor complex separate because of different electrophoretic velocities, each producing detectable product in their respective zones. Differences is electrophoretic velocity may be inherent in the compounds and/or may be due to charge modification of the chemical species by techniques known to those skilled in the art. Ultimately, detectable product passes the detector in two bands producing two product peaks on the electropherogram. One peak corresponds to product produced by the excess competitor and the other peak corresponds to product produced by the analyte-competitor complex, the latter peak being directly proportional to the amount of analyte in the original sample. A computer attached to the output device of the detector will be able to manipulate the generated data to mathematically distinguish each product peak into its respective source, allowing an accurate quantitation of the analyte.

It should be understood that the reactions described above may involve multiple immobilized reactants, multiple analytes and/or multiple competitors having different biorecognition portions. Consequently, more than one competitor may be subjected to electrophoretically mediated microanalysis and/or more than one analyte-competitor complex may be formed in a direct or competitive homogeneous reaction. In multiple analyte assays, typically more than one first reactant is introduced into the channel and plural detectable products are formed or depleted.

2. Mixing of Reagents

The mixing of the analyte and reactant is accomplished according to the invention by exploiting differences in electrophoretic velocity between chemical species. The inventive methods require that at least one chemical species, the reactant or the analyte, be electrically charged and, thus possess a characteristic mobility in an electric field. Where both analyte and reactant are charged, differences in charge density will result in differential electrophoretic mobilities in an electric field. Electrophoretic mixing may be achieved where (i) the faster moving component overtakes the slower moving component while one or both are migrating towards the same electrode, or (ii) ionic components moving in opposite directions electrophorese into each other during migration through the capillary.

The electrophoretic velocity of a given species is defined as the sum of a chemical species' electrophoretic mobility, gem, and the capillary electrophoretic system's electroosmotic flow, $\mu_{eo}$. Electrophoretic mobility is dependent upon the nature of the chosen electrophoretic medium. In free zonal capillary electrophoresis system employing a buffered electrophoretic medium, the electrophoretic mobility of a charged species is governed by the charge density of the substance, and is defined by the equation:

$$\mu_{em} = \frac{Ze}{6\pi\eta a} \quad (3)$$

where Z is the effective net charge of the species, e is the electrical charge, $\eta$ is the solution viscosity, and a is the hydrodynamic radius of the species.

Sieving medium is employed as in capillary gel electrophoresis, electrophoretic mobility is determined by both charge density and molecular dimensions. In micellar electrophoretic separations, electrophoretic mobility is dependent upon both the chemical species' electrophoretic mobility in the bulk solution and the partitioning coefficient of the species as a charged micellar additive with its own electrophoretic mobility. In various forms of capillary electrophoretic separations involving complexatory additives in the electrophoretic medium, electrophoretic mobility is determined by the charge density of the analyte as well as the degree of complexation with a charged or uncharged additive possessing its own electrophoretic mobility. The availability of different electrophoretic media allows various physical properties of analyte or reactant to be exploited so as to vary its electrophoretic velocity. This, in turn, allows the components to electromigrate at different rates in an electric field. Therefore, spatially distinct zones of chemical species can be brought into physical contact within an electric field.

Figure 4:
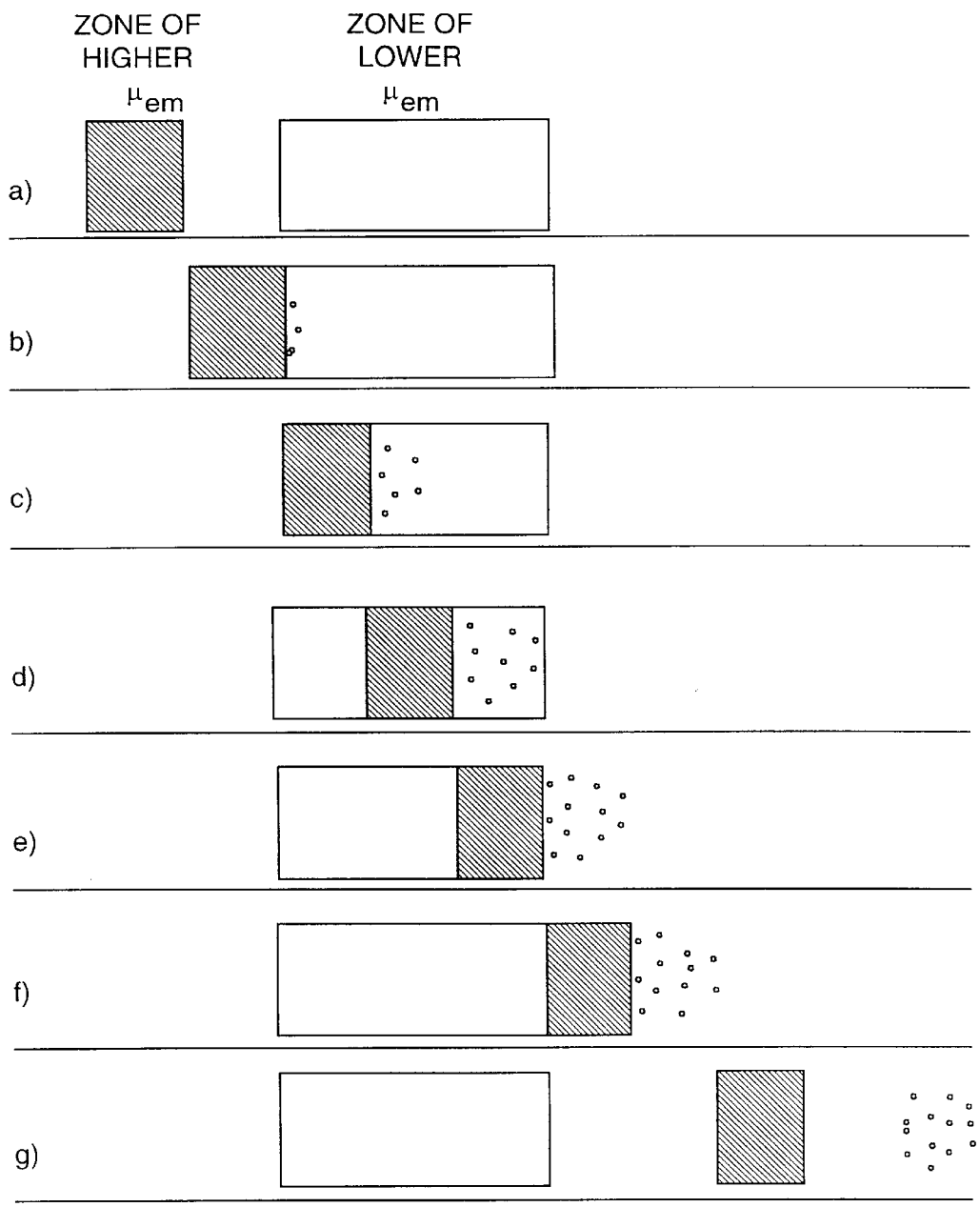
FIGS. 4: (a)–(g) are schematic illustrations of the process of the invention, wherein two zones (a) approach each other, (b) initiate chemical contact and begin to produce a product, (c) become superimposed, (d) interpenetrate one another, (e) begin to disengage, (f) fully disengage, and (g) move away from each other. The product, indicated by dots, is simultaneously formed and electrophoretically separated from the reacting chemical species within the zones.

Typically, in an assay of the invention, a zone or plug containing analyte will be merged with a zone containing reactant. As a potential is applied, the zones will migrate towards each other, as shown in FIG. 4(a), at a rate dependent upon the difference in electrophoretic mobilities of the two components of interest in the given electrophoretic medium. At a given point along the capillary, the zones will come into contact and begin to merge (FIG. 4(b)). Simultaneously, product will begin to form, and migrate towards the detector at its own characteristic velocity. In FIG. 4, product is indicated as dots. The time required for the reagent zones to make physical contact ($t_{contact}$) can be calculated based upon the difference in electrophoretic mobility between the two species ($\Delta\mu_{em}$), the distance between the zones (d, the distance between the leading edge of the zone of greater electrophoretic velocity and the trailing edge of the zone of lower electrophoretic mobility), and the applied electric field strength (V/L):

$$t_{contact} = \frac{dL}{\Delta\mu_{em}V} \quad (4)$$

The interpenetration of the two zones will continue as the potential is maintained, and formation and separation of product continues. Equation (4) also can be used to calculate the time required for the two reagent zones to fully interpenetrate (e.g. the smaller zone is completely merged within the larger zone) if d is defined as the shorter distance of that between the two leading edges or the two trailing edges (FIG. 4(c)). The full interpenetration of the smaller zone within the larger zone will continue, as shown in FIG. 4(d), until disengagement of the zones begins (FIG. 4(e)).

The time at which full interpenetration of the smaller zone within the larger zone ends can be calculated from equation (4) if d is defined as the greater distance of that between the two leading edges or the two trailing edges. The time interval during which total merging of the zones occurs ($\Delta t_{merge}$) can be estimated as $$\Delta t_{merge} = \frac{\Delta wL}{\Delta\mu_{em}V} \quad (5)$$

where $\Delta w$ is the difference in widths of the two peaks.

The zonal engagement will cease (FIG. 4(f)) as the two zones completely pass by each other (FIG. 4(g)). The time at which the two zones fully disengage can be calculated from equation (4) if d is defined as the distance from the trailing edge of the zone of greater electrophoretic velocity to the leading edge of the zone of lesser electrophoretic velocity.

There are numerous advantages to electrophoretic mixing over conventional mixing of bulk solutions. As molecular species electromigrate essentially independently of the bulk solution, electrophoretic mixing merges two or more zones of electromigrating components without a substantial change in volume and, therefore, without dilution of the zones. Present theory on capillary electrophoresis systems suggests that lateral diffusion is the major factor causing dilution of reagent zones. A zone of analyte can be made to engage several hundred times its own volume of reactant by allowing a small zone of analyte to migrate through a larger zone of the reactant. The ratio ($R_{vol}$) of reactant volume to analyte volume encountered by a relatively narrow analyte zone as it interpenetrates a wide reactant zone is dependent upon the difference in electrophoretic mobility between the two species ($\Delta\mu_{em}$), the width of the analyte zone (w), the time over which engagement of the two zones occurs ($t_{engage}$), and the electric field applied (V/L):

$$R_{vol} = \frac{\Delta\mu_{em} t_{engage} V}{LW} \quad (6)$$

Electrophoretic mixing allows for two zones to be fully interpenetrated without the need for turbulent flow and resulting bandspreading. In the chemical analysis of the invention, nanoliter streams of eluent and substrate are mixed within a few seconds, and the product is transported through a laminar flow system to the detector with minimal bandspreading. Bandspreading is minimized due to quick transport of product to detector relative to the duration of the chemical reaction; i.e., as soon as product is formed, it is transported to the detector. The fast transport time may be attributed to the small size of the capillary and the large electric potential applied to the system. Typically, the capillary is 25–100 $\mu$m in diameter and 5–100 cm in length. The range of electric potential applied to the system is usually in the range of 1–300 volts/cm, but may be as high as 2000–3000 volts/cm. Shorter assay times may be achieved in a number of ways, e.g., by decreasing the length of the capillary and coordinately decreasing the voltage applied to the system, or by increasing the length of the capillary and coordinately increasing the voltage. Thus, the inventive methods are optimized such that, once rapid electrophoretic mixing initiates the chemical reaction and product is formed, product is quickly transported to the detector. The efficiency of analysis methods of the invention, typically greater than $10^5$ theoretical plates, allows for the transport and mixing of reagent zones with minimal bandspreading. The absence of significant turbulence also simplifies theoretical and experimental considerations of the analytical methods.

The pre-reaction phase of the inventive methods also can be used to separate different analytes of a sample which interact with the same or different analytical reagent to produce or deplete the same or similar detectable products. Differences in electrophoretic velocities of the analytes in an electrophoretic medium may be exploited by performing a separation of the analytes prior to their engagement with the zone containing the reactant. This capability allows for the determination of plural analytes which are converted to indistinguishable detectable products if the analytes themselves possess dissimilar electrophoretic mobilities in the chosen electrophoretic medium.

Electrophoretic mobility also can used to separate unbound competitor from bound analyte, bound competitor and an immobilized reactant before mixing the unbound competitor with a first reactant. The analyte may be an antigen or a biological molecule. The immobilized reactant may be an immobilized antibody, an immobilized DNA or an immobilized PNA. Generally, the analyte to be quantitated binds to the immobilized reactant by a variety of mechanisms known to those skilled in the art, e.g., among others, hydrogen bonding, affinity bonding, covalent bonding, ionic bonding, electrostatic charge attraction and hydrophobic-hydrophobic interaction. Although the immobilized reactant preferably is an antibody and the analyte is an antigen, the following discussion equally is applicable to any analyte and any immobilized reactant.

In the binding reaction of an assay, an antigen will bind to an immobilized antibody. A competitor will either compete with the antigen for antibody binding sites (a "competitive" assay; FIG. 1) or will bind to the antigen in a "sandwich-type" arrangement (a "direct" assay; FIG. 2). In a properly designed experiment, an excess of the competitor is used so that unbound competitor will be present after all of the antigen is bound. Subsequent to an incubation period, an electrical current is applied to electrophoretically migrate the unbound competitor into a channel containing an electrophoretic medium. Typically the buffer solution in the reaction of the competitor with the immobilized antibody and the analyte is similar to the electrophoretic medium. Following migration of the unbound competitor into the channel which contains a first reactant, a second reactant portion of the competitor will catalyze a reaction with the first reactant to produce a detectable product which also migrates along the channel and ultimately is detected. Many of the same concepts discussed herein are applicable to the reaction, electrophoresis and detection of the competitor, the first reactant and the detectable product. Quantification of the analyte is accomplished using methods described elsewhere herein.

The binding reaction described above also may be conducted outside of an analytical device of the invention or outside of the electrophoresis apparatus, e.g., in a vessel. When the binding reaction is conducted independently, after an appropriate incubation period, an aliquot of the solution from the vessel is introduced into the channel containing an electrophoretic medium and a first reactant. Subsequently, the assay is completed as described elsewhere herein.

Electrophoretic mobility also may be used to separate a competitor from an analyte-competitor complex before mixing with a first reactant in a "homogeneous" assay format (FIG. 3). The analyte and competitor may be any species that will bind to each other via the biorecognition moiety of the competitor. After sufficient time is allowed for association to occur between the analyte and an excess amount of the competitor, an aliquot containing the analyte-competitor complex and the excess competitor are introduced into the channel. Introduction of the aliquot and the first reactant into the channel may be by conventional injection methods described herein or by electrophoretic migration. A first reactant also in introduced into the channel. Typically, the first reactant is present in the channel prior to the introduction of the sample. Subsequent to the introduction of the sample into the channel, electrophoretic motion is used to mix the aliquot with the first reactant. Upon application of an electric current along the channel, the competitor and the analyte-competitor complex separate because of different electrophoretic velocities. Thus, the mixing of the first reactant with the competitor and the analyte-competitor complex will occur in different zones of the channel as time progresses.

3. Chemical Reactions Useful in the Invention

The chemical reactions which may be performed electrophoretically according to the invention to analyze an analyte involve a pre-electrophoretic binding reaction with the analyte and a competitor, followed by an electrophoretically mediated reaction of the second reactant portion of the competitor with a reagent to produce or deplete a detectable product. The product is detectable by virtue of its unique electrophoretic mobility or electrophoretic properties. The reactions which are performed according to the invention fall within three categories, all of which involve the formation of a product or complex caused by reaction between a sample analyte and a competitor, or a competitor and a reactant.

(1) Non-catalyzed reactions. Thermodynamics favor the spontaneous occurrence of a some reactions without the aid of a catalyst. For example, the analyte being determined may react stoichiometrically with a competitor to produce or deplete a product which possesses a property which is more easily detected than the analyte itself. The product is detectable by virtue of a unique electrophoretic property.

(2) Catalyzed reactions. The energy required for activation of a chemical reaction is decreased by a catalyst, e.g., an enzyme. Some reactions occur only in the presence of a catalyst. The inventive methods may be used to analyze the competitor, analyte-competitor complex, enzyme, substrate or any species essential to the reaction, e.g., a coenzyme.

(3) Coupled reactions. In some chemical reactions, the reaction of analyte and a competitor, or a competitor and reactant to produce product does not produce or deplete a product which is detectable. However, product can be converted to yet another product which is detectable. For example, glyceraldehyde kinase converts glyceraldehyde and ATP to glyceraldehyde-3-phosphate (G-3-P) and ADP. G-3-P in the presence of NAD is converted by glyceraldehyde-3-phosphate dehydrogenase into 3-phosphoglyceric acid and NADH. NADH has a unique absorbance at 340 nm that allows it to be quantitated in the presence of other substances in the sample. The presence of NADH can be correlated to the presence of the analyte in the sample (e.g., glyceraldehyde, glyceraldehyde kinase, or ATP). This coupled set of reactions allows a substance without a unique chromophore to be determined spectrophotometrically by coupling the reaction to reduction of NADH. Coupled reactions may be catalyzed or non-catalyzed. Multiple coupled reactions may be performed substantially simultaneously, where different analyte, competitor and reactant zones have differing electrophoretic velocities.

The separative capability of capillary electrophoresis also can eliminate the need to couple the analytical reaction to a reaction which produces a species with unique detection properties. If the analytical reaction produces or depletes a product with unique electromigratory properties, the separative capability of capillary electrophoresis can allow this substance to be detected without the need to produce or consume species with unique detection properties. For example, glucose is converted to glucose-6-phosphate by hexokinase with the concurrent transformation of ADP to ATP. Because none of these chemical species possess unique UV detection properties, the clinical enzymatic determination of glucose requires that glucose-6-phosphate be enzymatically converted to 6-phosphogluconate by glucose-6-phosphate dehydrogenase with the simultaneous conversion of NAD to NADH. An increased absorbance observed at 340 nm resulting from the production of NADH in the coupled reaction can be correlated to the amount of glucose present in the sample. Alternatively, glucose may be analyzed via its reaction with hexokinase without coupling the conversion of glucose to a second reaction. ADP and ATP each exhibit a similar molar absorptivity at 270 nm. However, ADP and ATP possesses different charge density and, therefore, a different electrophoretic mobilities. As a result, the consumption of ATP or the production of ADP in the chemical reaction between glucose, hexokinase, and ATP may be analyzed by monitoring the electromigration of ADP and/or ATP past the detection window. The resulting ADP peak and ATP deficit peak each serve as a quantitative measure of the glucose present in the sample.

Listed in Table I of U.S. patent application Ser. Nos. 08/386,224 and 07/944,846 and in PCT publication WO 94/07132, which are herein incorporated by reference, are some representative examples of chemical reactions which may be performed according to the capillary electrophoretic methods of chemical analysis described herein. (This list of chemical reactions which can be performed according to the invention is not meant to be comprehensive, but merely represents some of the chemical reactions which may be performed during the course of an analysis.) In each reaction, different components of the chemical system may be measured. For example, in an enzymatic system, the disappearance of substrate, the accumulation of product, or the appearance or disappearance of a by-product of the reaction (e.g. a coenzyme, such as NAD or NADH) may be detected. Furthermore, the stoichiometric relationship between the species monitored and the analyte of interest allows for quantitation of various components of the reaction system. In an enzymatic system, the species monitored can be used to quantitate the substrate, the enzyme, a cofactor, or an analyte.

For example, in the triiodothyronine ("T3") enzyme immunoassay subsequently described in more detail in Example 2, T3-Alkaline Phosphatase ("T3-ALP conjugate"), the competitor, converts AttoPhos Substrate, a non-fluorescent compound, into a fluorescent product that is detected and quantitated. Basically, after competition between the T3 and the T3-ALP conjugate for immobilized anti-T3 monoclonal antibody binding sites, the amount of unbound T3-ALP conjugate in the sample is proportional to the amount of T3 present in the original biological specimen. That is, the more unbound competitor, the more T3 present in the sample.

The unbound T3-ALP conjugate from the immunological reaction then is introduced into a capillary containing the AttoPhos Substrate. The amount of fluorescent product formed by the T3-ALP conjugate is proportional to the amount of unbound T3-ALP conjugate. The amount of unbound T3-ALP conjugate is determined by measurement of the amount of fluorescent product produced. Thus, ultimately, the amount of T3 in the original specimen can be quantified since the amount of unbound T3-ALP conjugate is proportional to the amount of T3 in the original specimen.

4. Kinetic Considerations

The chemical reaction performed according to the invention is governed by the kinetics of a chosen system. A simple irreversible reaction, such as $$A+R \rightarrow P$$

where A is the analyte, R is the analytical reagent, and P is the detectable product, serves as an example. An assay according to a method of the invention is typically performed with the analytical reagent in excess of the analyte ([A][R]) and pseudo-first order kinetics are expected as the analyte plug passes through the reagent zone. As the analyte zone engages the analytical reagent zone, A will be depleted and P will be produced at a rate directly proportional to the instantaneous concentration of the depleting A at a given point within the interpenetrated zones. The integrated pseudo-first order rate equation for an assay performed under these conditions is:

$$[A]_f = [A]_i e^{-kt} \quad (7)$$

where $[A]_i$ and $[A]_f$ are the initial and final concentrations of A, respectively, and k is the pseudo-first order rate constant.

Knowledge of the time necessary to perform the analytical reaction as well as the mixing process permits the design of an assay according to the invention. The assay can be designed in terms of separation length and applied electric field in order to minimize the analysis time, yet allow sufficient time for performance of the assay. Using equation (7), the time of reaction ($t_{rxn}$) required to reach a desired quantitative extent of reaction ($\epsilon$) can be estimated as:

$$t_{rxn} = \frac{\ln(1-\varepsilon)}{k} \quad (8)$$

A second example of the reaction kinetics expected in assays performed according to the invention are those involved in enzymatic reactions. The Michaelis-Menten model accounts for the kinetic properties of many enzymes:

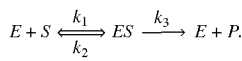

An enzyme (E) combines with a substrate (S) to form an enzyme-substrate complex (ES) with a rate constant of $k_1$. The ES complex can either dissociate to E and S, with a rate constant of $k_2$, or it can proceed to form product, P, with a rate constant of $k_3$. The Michaelis-Menten equation:

$$v = \frac{V_{\max}[S]}{K_m + [S]} \quad (9)$$

shows that the rate or velocity (v) of the reaction of a single substrate with an enzyme is dependent upon the maximal rate of reaction when the enzyme is saturated with substrate ($V_{max}$), the concentration of the substrate ([S]), and the Michaelis-Menten constant ($K_m$). $V_{max}$ is equal to the product of $k_3$ (the turnover number) and the total enzyme concentration ($[E_T]$).

The turnover numbers for most enzymes with their physiological substrates typically lie in the range of 1 to $10^6$ per second. Defined as $(k_2+k_3)/k_1$, $K_m$ values for enzymes range widely though generally lie between $10^{-1}$ and $10^{-7}$ M. The $K_m$ value for an enzyme depends upon the particular substrate as well as environmental conditions such as temperature, pH, and ionic strength.

The Michaelis-Menten equation reveals that at high substrate concentrations ($[S] \gg K_m$), where the enzyme is saturated with substrate, v will approach $V_{max}$ and remain relatively constant until the substrate is depleted or until product accumulation produces inhibition. At low substrate concentrations ($[S] \ll K_m$), the rate of the reaction is directly proportional to the concentration of the substrate. As a zone of substrate merges with a zone containing enzyme, the initial rate of the reaction will depend upon the relative concentrations of the substrate and enzyme within the overlapping region. If the concentration of substrate is high enough so that enzyme-saturating conditions prevail, a relatively constant reaction rate ($V_{max}$) will be observed until sufficient substrate depletion has occurred and enzyme-saturating conditions no longer exist. As the substrate is depleted, the rate of the reaction and, therefore, production or depletion of the detectable product will decrease. The rate at which this depletion of substrate occurs depends upon the relative concentrations of the enzyme and substrate, as well as the turnover number of the enzyme. This rate is also dependent upon the Michaelis-Menten constant of the enzyme for the given substrate.

5. Detection of Product

The detection process according to the methods of the invention is generally performed by allowing the electro-osmotic flow of the capillary electrophoretic system to transport the detectable product to the detector. As long as the detectable product has an electrophoretic mobility that is oriented in the same direction as the electro-osmotic flow, or is oriented in the opposite direction but is of a lower magnitude, any detectable product which is formed prior to the analyte passing by the detection window will be observable.

Because the detectable product is electrophoresed away from the reacting analyte at a constant rate (equal to the difference in electrophoretic mobility between the analyte and the detectable product), the resulting peak in the electropherogram provides a profile of the rate of the reaction. The time required for the observed detectable product to migrate to the detector ($t_{mig}$) can be calculated as shown in equations (10), (11), and 12. $T_{mig}$ depends upon the time during which the analyte moves ($\mu_{em,a}$) within the capillary from the point of injection (d) prior to product formation, and the time ($t_{det}$) required for the product to move ($\mu_{em},p$) the remaining distance (l-d) to the detector window:

$$t_{mig} = t_{form} + t_{det} \quad (10)$$

$$t_{mig} = t_{form} + \frac{(l-d)L}{(\mu_{em,p} + \mu_{eo})V} \quad (11)$$

$$t_{mig} = t_{form} + L - \frac{(\mu_{em,a} + \mu_{eo})V t_{form}}{(\mu_{em,p} + \mu_{eo})V} \quad (12)$$

The following equation allows for estimation of the time at which a given observed product was formed in the assay:

$$t_{form} = \frac{t_{mig} + \dfrac{lL}{(\mu_{em,p} + \mu_{eo})V}}{1 - \dfrac{\mu_{em,a} + \mu_{eo}}{\mu_{em,p} + \mu_{eo}}} \quad (13)$$

The shape of the expected peak can be predicted based upon the kinetics of the reaction. In the simple pseudo-first order example cited previously, if it is assumed that the mixing process occurs very rapidly, such as $t_{mix} \ll t_{rxn}$, the time of formation of the product is approximately equal to the time during which the analyte is merged with the reagent zone and reaction occurs ($t_{form} \cong t_{rxn}$). This assumption allows for the following derivation of an expression for the rate of the reaction and, therefore, amount of detectable product formed with a given migration time.

$$v = k[A]_i e^x \quad (14)$$

$$\text{where } x = (-k)\frac{t_{mig} - \dfrac{lL}{(\mu_{em,p} + \mu_{eo})V}}{1 - \dfrac{\mu_{em,a} + \mu_{eo}}{\mu_{em,p} + \mu_{eo}}}$$

If the electrophoretic mobility of the detectable product is greater than that of the analyte, the condition that $$t_{mig} \geq \frac{lL}{(\mu_{em,p} + \mu_{eo})V} \quad (15)$$

exists, the first detectable product formed by a given region of analyte will be the first to reach the detector, and the kinetic effect on peak shape will be observed on the trailing edge of the peak. If the electrophoretic mobility of the detectable product is less than that of the analyte, the condition that $$t_{mig} \leq \frac{lL}{(\mu_{em,a} + \mu_{eo})V} \quad (16)$$

prevails. In addition, the first detectable product formed by a given region of analyte will be the last to reach the detector, and the kinetic effect on peak shape will be observed on the leading edge of the peak.

An experimental peak shape will be further convoluted by factors such as the width of the analyte volume or plug, diffusion by the analyte and detectable species, and uneven depletion of the analyte zone due to the time required for the reagent zones to interpenetrate. For reactions with fast kinetics, the peak shape predicted by the kinetics may be obscured by these factors. Incomplete reaction of the analyte volume may be observed if the analyte has not fully reacted with the reactant volume prior to the analyte passing by the detector, since any detectable product formed after this point will not be detected. Similarly, an incomplete reaction may be observed if the volume of the reactant zone is insufficient for complete reaction of the analyte prior to the two zones disengaging. An incomplete reaction is indicated by truncation of the peak obtained for the detectable product.

6. Continuous or Interrupted Electric Field

During electrophoretic mixing, contact between analyte and reactant may be transient or continuous. Transient contact occurs when two narrow zones traveling at different velocities meet within the electrophoresis channel. Initially, the two zones migrate into each other and thus mix. This is followed by zone disengagement as the two species move apart due to differences in their electrophoretic mobility. Product will be formed only during the time that the two species are in contact while the two zones are engaged. The chemical reaction stops after the zones disengage.

Continuous contact is achieved in several ways. During zonal engagement and mixing, the chemical reaction may be carried out under either zero potential (the "stopped flow" mode) or constant potential. At zero potential, when the electric field is interrupted by turning off the potential, neither electrokinetic nor electrophoretic transport occurs and the reactants remain mixed in a single zone where product accumulates. This corresponds to a fixed time reaction in conventional enzyme assays. Enzymes which require longer incubation times to produce sufficient product for detection, e.g., a dilute enzyme preparation or an enzyme having a low turnover number, may be assayed in the zero potential mode. Although this method of continuous contact is highly sensitive, it is necessary to ascertain the moment of engagement of the zones in order to interrupt the electric field. This may be accomplished by monitoring a given parameter indicative of the relative positions of the zones, or by standardizing the system such that the positions of the zones are predictable given a certain length and diameter of capillary, electric potential, and analyte and reactant mobilities. If it is not possible to observe the relative positions of the sample and reactant zones, then the zones may be electrophoresed for a long enough time to allow them to pass each other, and the reaction is followed by detection during the entire time interval.

Under constant potential, the analyte and reactant are mixed and separated from product continuously. Conventional assays do not involve electrophoretic mixing and separation of the components of a chemical reaction. Simultaneous product accumulation and separation in conventional assays are difficult to achieve because rapid mixing of analyte and reactant may perturb separation of the product from the other components. That is, mixing and separation of the sample components, the reactant, and the product will occur both during and after the chemical reaction. The methods of the invention overcome perturbation of the separation of product from reactants because both mixing and separation rely on the electrophoretic mobilities of the components of the chemical reaction; i.e., rapid electrophoretic mixing of analyte and reactant initiates the chemical reaction, and the product is then electrophoretically separated from the other components. Assays carried out under constant potential according to the invention usually correspond to short, fixed time assays because the reaction e.g., enzyme catalysis, may occur orders of magnitude faster than the rate of separation. For example, product formation on a molar basis may be $10^2$–$10^4$ times greater than the amount of enzyme, depending on the turn-over number of the enzyme and the potential applied across the zone.

Another method of continuous contact is to use a large volume of reactant relative to the volume of sample containing the analyte. In a small electrophoresis channel, e.g., in a capillary, it will take a period of time for the analyte to migrate through the relatively larger zone of reactant. The reaction of analyte with reactant continues throughout the time during which analyte migrates past the large zone of reactant. In this continuous contact method of mixing, product is formed throughout the zone of reactant and is continuously electrophoresed away from the sample zone. The product is thus more dilute than the accumulated product which formed during interruption of the electric field.

Dilution is greater with small samples and diminishes as the reactant volume becomes larger. In conventional chemical reactions, the dilution of sample which occurs during mixing of the sample and reactant generally lowers the sensitivity of detection. During chemical analysis according to the invention, sample dilution is also a function of relative volumes of sample and reactant, but only up to a certain concentration of sample, as described herein. Beyond that sample concentration, there is no dilution upon mixing.

In electrophoretic mixing, there is an optimum sample volume which will cause little dilution and give maximum sensitivity. This sample volume will be related to the number of theoretical plates, the capillary radius, the diffusion coefficient of the analyte, the viscosity of the running buffer, the electric potential, and the other variables that control bandspreading. This optimum volume may be calculated as follows.

Electrophoretic bandspreading theory reveals that, for a capillary column of a certain number N theoretical plates, a sample is contained in a detection volume ($V_d$) as it passes through the detector. This volume, $V_d$, is said to be independent of the sample volume ($V_s$), i.e., the sample volume is diluted up to the volume $V_d$. In this respect, electrophoretic mixing is similar to other types of mixing; i.e., all methods of mixing result in some dilution of the sample. However, as sample volume $V_s$ increases to approximately $V_d$, there is little increase in $V_d$. Finally, when $V_s$ is much larger than the volume $V_d$ seen in analytical systems, there will be no dilution at all except on the leading and trailing edges of the peak.

The relative sizes of sample zone and reactant zones also affect the speed and ease with which electrophoretic mixing may occur. Mixing of two small zones will be very rapid at high voltage. First the edges of the zones will mix, and then the two zones will be superimposed if they have exactly the same shape and volume. In general, mixing will not be instantaneous. Thus, the reaction may begin before mixing is complete, depending upon both the rate with which analyte and reactant react and the dependence of the reaction rate on the concentration of reactant in the system. It is possible that product formation will not be constant during the course of mixing. When product is accumulated as an electrophoretic peak and transported to a detector, this peak is subject to the same bandspreading (dilution) phenomena that characterize all electrophoretic systems. At small sample volume, the bandspreading effect is greatest. As sample volume increases, there is less bandspreading.

The most convenient volumes for performing the method of the invention include combining a small volume and a large volume. For example, a small sample volume may be mixed with a large reagent volume, as follows. (Where the small volume is the reagent and the large is the sample, the procedure is essentially the same.) The capillary is first filled with the large volume, e.g., reagent; the small sample volume is then introduced at the capillary inlet. An electric field is imposed on the capillary and, after a few seconds of high electric potential (e.g., 100–300 volts/cm) the analyte and reactant will be mixed. It is then possible to vary the electric potential in order to control reaction time and allow the reaction to go to completion. For example, at zero potential, product will accumulate in a limited area and result in greater detection sensitivity. Alternatively, allowing the reaction to occur continuously, i.e., without turning off the potential will promote separation of product from analyte and reactant. Under continuous potential, product will accumulate to a lesser extent than product formed during a reaction performed at zero potential, and there will be a consequent diminished sensitivity of detection.

In contrast to mixing of two small volumes or a small and a large volume, mixing of two large volumes requires a longer time period of electrophoresis. In addition, there is more variability of the extent of the chemical reaction within the merging zones with two large volumes. The leading edges of two large zones make contact before the trailing edges and thus the analyte and reactant in the leading edges will react earlier than analyte and reactant in the trailing edges. This variability may be decreased by increasing the potential applied to the system. Thus, although it is desirable to rapidly mix and initiate a reaction using a small and a large volume, mixing and initiation of two large volumes is also possible if performed at a high potential.

7. Assay for Enzyme Activity or Concentration

The shape of the electropherogram obtained with the Michaelis-Menten kinetics described above depends upon the relative concentrations of the substrate and enzyme. In the assay of any enzyme according to the invention, the reactant zone (in this example, the substrate) contains enzyme-saturating concentrations of any chemical species needed for the reaction, such as substrate and coenzymes. As the analyte (enzyme) zone interpenetrates the reactant (substrate) zone, the enzyme/substrate reaction occurs, thereby producing or depleting the detectable product. If the substrate is of sufficient concentration so as to maintain enzyme-saturating conditions throughout the enzyme's electromigration through the substrate region, a relatively constant reaction velocity and thus a relatively constant production or depletion of the detectable species will be observed. As the zones first begin to interpenetrate, the quantity of detectable product will be low due to minimal zone overlap and low concentrations encountered at the edges of the zones (see FIG. 4(b)). Once the enzyme zone has fully engaged the substrate zone, a relatively constant reaction rate should be observed. Within the enzyme-saturating substrate zone, most of an enzyme will be sequestered in the enzyme-substrate (ES) complex, and the enzyme will traverse the substrate region with the electrophoretic mobility of the ES complex. The electrophoretic mobility of the ES complex can be different than that of either E or S individually.

The highest sensitivity (i.e. greatest product accumulation) is achieved for enzymes with high turnover rates and systems in which the ES complex and detectable product differ little in electrophoretic mobility. The resulting electropherogram displays a plateau representative of the relatively constant rate of the reaction as the enzyme traversed the substrate region. The maximal velocity at which an individual enzyme can react with substrate is fixed by the turnover rate of the enzyme at the given experimental conditions. Variations in the height of the plateau for different injected samples of enzyme corresponding to variations in the observed rate of the reaction must be related to the quantity of enzyme operating at its maximal rate. Thus, the height of the plateau is related directly to the quantity of enzyme contained in analyte injection. The plateau is observed in the resulting electropherogram until the enzyme zone passes by the detector position or until the two zones disengage.

Figure 5:
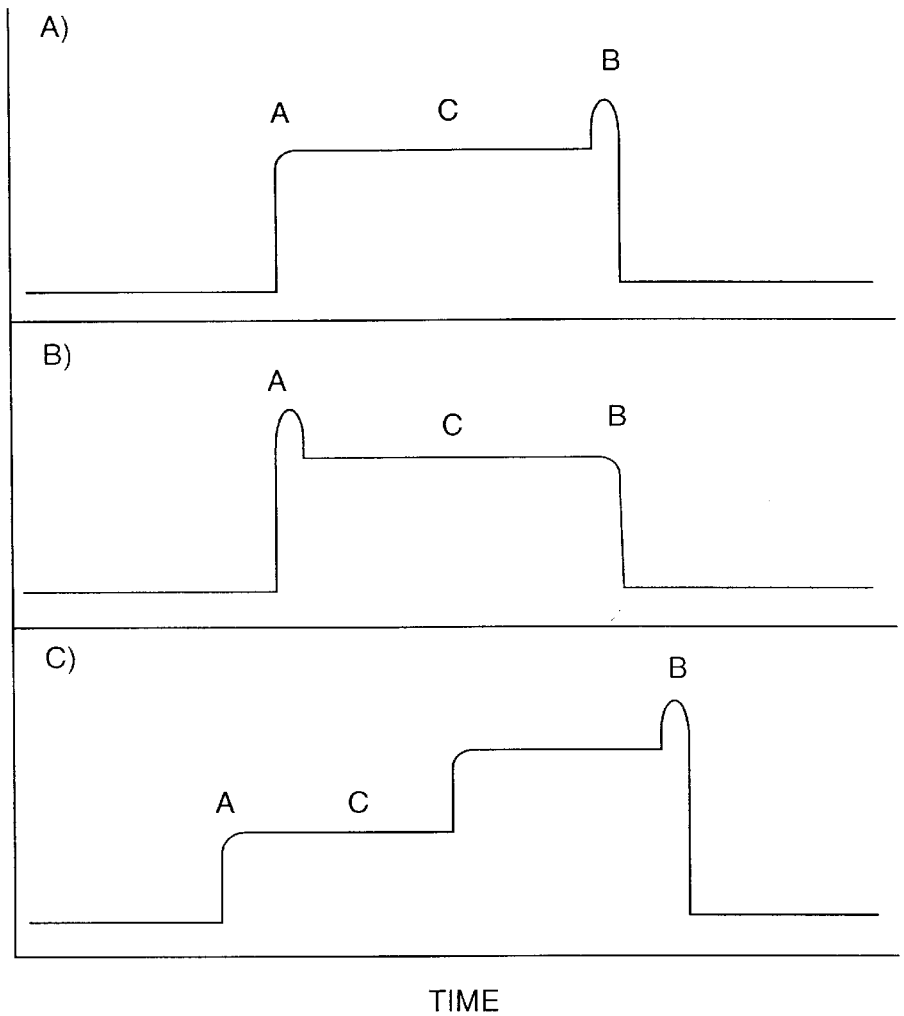
FIGS. 5: (A)–(C) are schematic representations of electropherograms in an EMCA enzyme assay in which (A) ES moves faster than P, and (B) P moves faster than ES, and (C) a multiple isoenzyme assay with the relative mobilities of the products being slower than those of the isoenzymes forming them.

The theoretical electromigration profile of a system in which the electrophoretic velocity of the ES complex is greater than that of the detectable product is shown in FIG. 5(A). Because the ES complex migrates at a faster velocity toward the detector than the detectable product (P), the first product observed at the detector window (point "A" in the electropherogram) is that product formed as the enzyme migrated past the detector. In contrast, product detected at the other end of the electropherogram (i.e., point "B") is that product formed when the enzyme first engaged the substrate zone. The peak or spike at B, often referred to as an "injection peak," is an artifact observed when a volume of enzyme is injected immediately adjacent to a region containing the substrate. This spike is the result of detectable product formed at the interface of the two zones due to diffusion which occurred between the time that enzyme is introduced into the capillary and the time potential is applied. The height of the electropherogram tracing at position "C" corresponds to the amount of product which forms while the enzyme traverses the capillary, and is proportional to enzyme concentration at constant current.

The electropherogram for an ES/P system in which the electrophoretic velocity of the detectable product is greater than that of the ES complex is shown in FIG. 5(B). The first detectable product to reach the detector (i.e., point "A") is that formed as the zones first merged. The last detectable species arriving at the detector (i.e., point "B") is that formed as the enzyme passes by the detection window. In either situation, if the width of injected enzyme volume is relatively narrow, the width of the observed peak represents the difference in electrophoretic mobility between the ES complex and the detectable species. Thus, the transport time of an analyte and the relative transport velocities of ES and P are easily ascertainable from the electropherogram tracings.

The width of the observed peak (Δt) can be related to the difference in electrophoretic mobility of the ES complex and the detectable species ($\Delta\mu_{em}$), the length of capillary in which engagement of the zones occurs (l), and the applied electric field strength (V/L):

$$\Delta t = \frac{lL}{\Delta\mu_{eo}V} \tag{17}$$

FIG. 5(c) illustrates the theoretical profile obtained in the multi-analyte determination of isoenzymes in which the different ES complexes formed by two isoenzymes exhibit different electrophoretic velocities. Although each reaction produces the same detectable species, specificity is obtained due to variability in electrophoretic velocity in the chosen electrophoretic medium.

For assays of enzyme performed in the zero potential mode, the enzyme volume is electrophoretically mixed with the substrate under applied potential, and the potential is then removed while the detectable product is allowed to accumulate for a fixed period of time. If enzyme-saturating concentrations of substrate are maintained throughout the incubation period, the quantity of product produced or depleted during this time period is directly related to the quantity of enzyme operating at maximal velocity. The resulting electropherogram exhibits a peak representing the accumulated product superimposed upon the plateau representing the product indicative of the applied potential periods necessary to induce electrophoretic mixing and transport of the product to the detection window. Due to the higher sensitivity achieved, the zero potential mode is particularly preferred to analyze dilute enzyme solutions or enzymes having a low turnover number.

Figure 6A:
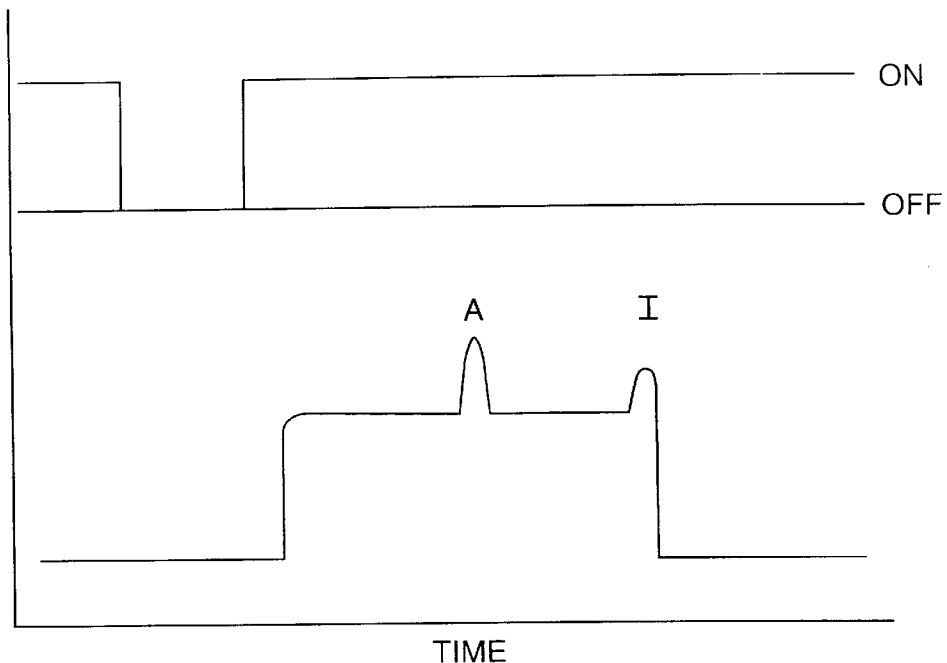
FIGS. 6(a) and 6(b) show a potential program applied according to the invention in which the voltage is dropped to zero and then reapplied (top), and the resulting electropherogram (bottom).

The sensitivity of methods of the invention is inversely related to the electric field applied for a given set of experimental conditions ($\Delta\mu_{em}$, length of capillary, and separation length). This effect is of particular interest when dealing with very small enzyme concentrations in the sample of interest. The sensitivity enhancement is proportional to the turnover number of the enzyme and the amount of time the reaction is allowed to proceed in the absence of an applied potential. FIG. 6(a) illustrates the electric potential program profile (top) employed in the zero potential mode and the expected electrophoretic profile (bottom). The injection peak has an "I" above the peak and the product peak generated during the zero potential period has an "A" above it.

The electrophoretic profile for a homogeneous reaction conducted in a zero potential mode is different. In a homogeneous assay, no immobilized reactant is present. An analyte in a specimen sample and an excess of competitor are mixed so that the resulting sample introduced to the channel contains the unreacted competitor and an analyte-competitor complex. Initially, both species are in the same zone of the channel. After an electric potential is applied, both species begin to migrate at different electrophoretic velocities due to differences in charge and/or mass. Subsequent to the separation of the competitor and the analyte-competitor complex into individual zones, typically the channel is subjected to a zero electric potential incubation period. During this time, detectable product independently is produced in each of the separate zones. After a sufficient time, the electric potential is re-imposed along the channel and the zones of product, the competitor, the analyte-competitor complex and first reactant, e.g., an enzyme substrate, begin to migrate again.

Figure 6B:
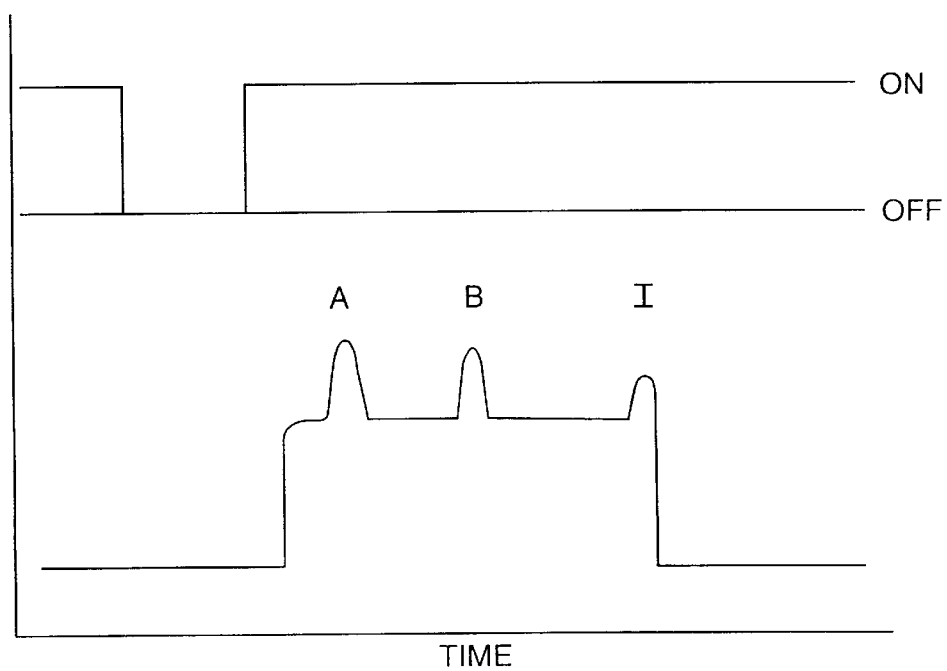

As product passes the detector, an electropherogram similar to FIG. 6(b) will be realized showing the presence of two main product peaks ("A" and "B") above the constant potential product plateau. The peak identified as "I" is the injection peak as discussed previously. One peak corresponds to product generated from the competitor and the other peak corresponds to the product generated from the analyte-competitor complex. The peaks can be distinguished by running the competitor alone under identical assay conditions and determining its retention time. Accordingly, the amount of analyte-competitor complex can be quantified from its corresponding peak, and therefore, the amount of analyte can be determined as well.

8. Assay for Substrate Concentration

The analysis of substrate concentration according to the invention may involve an enzymatic reaction, and thus, the analyte (substrate) zone will encounter the reagent (enzyme) zone with Michaelis-Menten kinetics. At high substrate concentration, the reaction rate and, therefore, production or consumption of detectable product will be relatively constant and independent of substrate concentration. Therefore, purely enzyme-saturating conditions are of little analytical value in the determination of a substrate. However, as the substrate is depleted, so that enzyme-saturating conditions no longer exist, the rate of the reaction will decrease until, eventually, it is directly proportional to the substrate concentration. As the plug of substrate continues to pass through the enzyme zone, the rate of the reaction and, therefore, production or depletion of detectable product, will lessen.

The velocity of a reaction for a region of substrate is a function of time as predicted by Michaelis-Menten kinetics. The detectable species is electrophoresed away from the reacting substrate at a constant rate which is dependent upon the difference in electrophoretic mobility between the substrate and the detectable product. The resulting peak in the electropherogram for the detectable product provides a measure of the velocity of the reaction at any given time within the assay. If the detectable product has a greater electrophoretic velocity than the substrate/analyte, the first detectable product formed will be first to be detected, and the electropherogram will take on the appearance of a descending plateau. If the detectable product has a lesser electrophoretic velocity than the substrate/analyte, the first detectable product formed will be the last to be detected, and the electropherogram will take on the appearance of an ascending plateau. The relative height and width of the peak will depend upon the relative electrophoretic mobilities of the substrate and product, the relative concentrations of the reagents, and the kinetic parameters of $K_m$ and turnover number at the given experimental conditions. The electropherogram obtained experimentally is also convoluted by the width of the substrate volume, dilution of the substrate and detectable species zones, and uneven depletion of the substrate volume which occurs during the interpenetration of the reagent zones.

In a substrate assay according to the invention, if electrophoretic mixing is assumed to occur relatively quickly, and the enzyme zone is sufficiently wide such that the two zones will remain merged throughout the substrate's migration from the injection to detection positions, the time available for the observed reaction of the substrate is equal to the time required for the substrate to migrate from the injection point to the detection window as determined by equation (2). Integration of the Michaelis-Menten equation yields the time required for a given amount of substrate to be enzymatically reacted ($t_{rxn}$):

$$t_{rxn} = \frac{[S]_i - [S]_f}{V_{max}} + \frac{Km}{V_{max}} \log\frac{[S]_i}{[S]_f} \quad (18)$$

where $[S]_i$ and $[S]_f$ are the initial and final concentrations of substrate, respectively.

In clinical assays of substrates, an end-point assay method is often used for determination of substrate concentration, such that the reaction is allowed to essentially reach completion prior to taking a spectrophotometric reading. In the inventive methods, substantially all of the substrate is allowed to react prior to its passing by the detection window. As a result, the descending or ascending plateau obtained eventually reaches the baseline, and the area under the curve is directly proportional to the quantity of substrate injected.

If the reaction is not completed prior to any remaining substrate passing by the detection window, the peak will be truncated without having returned to the baseline as the remaining unreacted substrate passes by the detection window. An attempt to extrapolate the peak to baseline may introduce error into the system due to the non-linear nature of the peak tail. This truncation effect places an upper limit on the linear range of the technique. However, the dynamic range of the method extends just up to that concentration of substrate which remains enzyme-saturating throughout its transit of the capillary. Measurement of the amount of product passing by the detector will be a dynamic measure of the quantity of substrate injected as long as sufficient substrate is depleted prior to the substrate passing by the detection window. It is desirable under these conditions to approximate non-enzyme-saturating conditions, although the resulting measurement may not be linear. While the reaction is never truly complete according to Michaelis-Menten kinetics, the time required to reach an acceptable extent of reaction, $\xi$, defined as the fraction of initial substrate reacted, can be estimated from equation (19):

$$t_r = (1/V_{max})(n[S]_i - K_m \log n) \quad (19)$$

Combining equations (2) and (19) allows for the calculation of the maximum concentration of substrate which can be reacted.

$$t_{rxn} = \frac{\xi[S]_i - K_m \log \xi}{V_{max}} \quad (20)$$

Therefore, the upper limit on the linear range for a given set of experimental conditions is calculated according to equation (21):

$$[S]_i = \frac{lLk_3[E_t]}{(\mu_{em} + \mu_{eo})V\xi} + \frac{k_m \log \xi}{\xi} \quad (21)$$

Higher concentration of substrate will result in truncation greater than that specified by $\xi$. Equation (21) also allows one to estimate the degree of truncation ($1-\xi$) experienced by a given initial concentration of substrate for a set of experimental conditions. As determined by equation (21), the upper limit on the linear range can be expanded by increasing the separation length of the capillary or decreasing the applied electric field. Each of these methods increases the quantity of substrate which can be reacted by increasing the reaction time of the substrate in the capillary. The expansion in the linear range is accompanied by an increase in analysis time proportional to the increase in separation length or inversely proportional to the decrease in applied electric field. Another method of extending the linear range without concurrently increasing the analysis time is to increase the concentration of enzyme (and, if necessary, coenzyme) in the buffer solution. Although this does not alter the turnover number of an individual enzyme, it will proportionally increase the value of $V_{max}$ by raising the number of enzyme molecules capable of operating at a given turnover number.

Typically, one substrate molecule is converted to one molecule of product. Thus, detection of the presence or amount of a product as an assay of substrate in a sample is not amplifiable, as is an assay for enzyme, where an enzyme converts substrate to product multiple times. Substrates which are routinely used in clinical determinations and which may be analyzed according to the invention are, e.g., adenosine 5'-triphosphate ("ATP"), ammonia, bile acids, carbon dioxide, cholesterol, ethanol, glucose, lactate, oxalate, pyruvate, triglycerides, urea, nitrogen, and uric acid.

10. Experimental Parameters

The experimental parameters which may be varied within any method of the invention include electro-osmotic flow, electrophoretic mobility, nature of the electrophoretic medium, pH, temperature, ionic strength, viscosity, sample volume, electric potential, length of capillary, detection method, and the concentrations of the reacting species. These parameters may be optimized for any chemical analysis performed according to the invention. Varying one or more of these parameters allows one of skill in the art to exploit a vast number of chemical analyses in the invention, and confers versatility on any method developed in accordance with the invention.

(a) Electro-osmotic Flow

Control of electro-osmotic flow allows for reproducible chemical analysis. Electro-osmotic flow is an inherent factor in the electrophoretic velocity of each chemical species present in the system, and affects the duration of contact of the reagents as well as transport of the detectable product to the detection window. The magnitude and direction of electro-osmotic flow determines the time available for contact of analyte and reactant and for the chemical reaction, as indicated by equation (2). Consistent and reproducible electro-osmotic flow is essential for quantitative analyses according to the invention, since the velocity of the species past the detection window is inversely proportional to the area of a peak. Electro-osmotic flow may be increased, decreased or reversed by altering the nature of the coating of the capillary. Alteration of the viscosity of the capillary coating directly affects electro-osmotic flow by increasing or decreasing the solution drag on molecules in the system. In addition, the pH of the electrophoretic medium as well as its ionic strength alter the zeta potential at the capillary/solution interface, thereby changing the solution flow.

Electro-osmotic flow also allows for flushing of the capillary without the need for mechanical flushing. An electrophoretic system will typically electro-osmotically pump a few to several hundred nanoliters per minute of bulk solution, depending upon the diameter of the capillary and the applied potential. Thus, the capillary may be cleansed and the electrophoretic conditions for the next analysis regenerated. Electro-osmotic flushing of the system also lowers the temperature of the capillary between runs, and thus counters the effects of Joule heating at high electric fields.

(b) Electrophoretic Velocity

The electrophoretic velocity of a chemical component of the analysis is determined by its electrophoretic mobility in an electric field and the electro-osmotic flow. The electrophoretic mobility of the component is affected by the nature of the electrophoretic medium, e.g., pH, ionic strength, and viscosity. An electrophoretic medium, e.g., free solution, sieving gel, partitioning or complexatory additives, or isoelectric focusing medium, may be chosen for physical properties which will selectively impede the electrophoretic mobilities of certain components of the system. For example, a more viscous medium can increase the molecular drag of the species and, therefore, decrease electrophoretic mobility. In addition, the degree of ionization of charged molecules in the system, e.g., an analyte, a competitor, or an analyte-competitor complex, can be selectively altered by buffering the medium at various pHs and varying the ionic strengths. Additionally, before or after molecules are introduced into the system, charge modifiers can be attached to the molecules or various substituents on the molecules can be charge modified by techniques known to those skilled in the art. Charge modification techniques applicable to electrophoresis is a topic in U.S. patent application Ser. No. 08/425,828, filed on Apr. 20, 1995, which is owned by a common assignee of this invention and is herein incorporated by reference. Equation (4) demonstrates that a difference in electrophoretic mobility can be induced by the selection of electrophoretic medium, pH, ionic strength, and viscosity.

(c) Viscosity

The viscosity of the electrophoretic medium may affect the diffusion coefficient for a given chemical species. Varying the viscosity of the medium is especially useful when performing assays at zero potential. As the viscosity of the medium increases, the diffusion of the components becomes less pronounced. Under zero potential conditions, increased diffusion of chemical components of the system is undesirable in that it diminishes the accumulation of detectable product. The viscosity of the medium may be modified according to any parameter known to one of skill in the art, including the following. Non-partitioning additives may be added to the medium, e.g., ethylene glycol or linear polymers. The medium may be a gel, since gels vastly increase the net viscosity of the solution, and product accumulation over an extended period of time will thus occur with little or no diffusion of the product.

(d) Volume of Sample and Reactant

The volume of sample and reactant, as well as the order in which they are introduced into the system, will be chosen in light of other experimental parameters, e.g., the relative electrophoretic velocities of analyte and reactant, the concentration of analyte or reactant within a zone, and kinetics of the chemical reaction itself. Generally, it is desirable that the zone containing a component having a higher electrophoretic velocity be introduced into the capillary later than the slower moving component zone, so that the faster component may overtake the slower component, provided the electrophoretic velocities of the components are oriented in the same direction. If the species possess electrophoretic velocities of opposite directions, the analyte and reactant zones may be introduced at different ends of the capillary such that they approach each other from opposite directions.

The relative widths of sample and reactant plugs is chosen based on the relative concentrations of analyte and reactant, as well as the desired sensitivity of detection. For example, when injecting a small zone of highly concentrated analyte, it is desirable to use a very large volume, e.g., extending the length of the capillary, of reactant. Thus, the analyte may be quantitatively reacted with reactant as it encounters many times its own volume of reactant (see equation (6)). Typical analyte/reactant volume ratios are 1/10, 1/100, or 1/1000, etc., with use of a larger reactant volume resulting in an increase in the proportion of reacted analyte. Another example under which a larger volume of reactant is preferred is where the reaction kinetics are very slow compared to the rate of zonal traversal of the interpenetrated reagents. Conversely, if the reactant concentration is high relative to the analyte concentration, a small plug of each may be injected to perform the chemical analysis according to the invention. A small analyte or reactant volume may also be used where the time of the chemical reaction is fast relative to the time the zones are interpenetrated.

(e) Applied Potential

The potential required to impart electrophoretic motion is typically applied across the capillary by a high voltage source operated at electric field strengths generally ranging from several hundred volts per centimeter to several thousand volts per centimeter. See U.S. Pat. Nos. 4,865,706 and 4,865,707 hereby incorporated by reference. The application of the potential can be controlled either via manual operation, a waveform generator, or computer control.

The rates of migration of chemical species in capillary electrophoresis are directly proportional to the electric field applied due to electrophoretic and electro-osmotic effects. Although the strength of the electric field strength does not affect the relative rates of migration of chemical species, as is evident from equations (2), (4), (5), and (6), the assay time, the time at which zonal engagement occurs, and the total time of interpenetration and, therefore, reaction are dictated by the applied potential. Once the analyte and reactant zones become engaged, the applied potential determine mine the nature of the contact: dynamic at potentials greater than zero and static at zero potential. Generally, low potential refers to approximately 1 to 100 volts/cm; high potential refers to approximately 100 to 300 volts/cm. However, depending upon the design of the assay conducted and the apparatus used, these voltage ranges may vary considerably. Lower electric field strengths result in slower movement of chemical species, thereby increasing the contact time of two zones. Furthermore, if the detectable species possesses a different electrophoretic mobility than the analyte (or the transient enzyme-substrate complex at enzyme-saturating conditions in an enzymatic assay), lower potential will proportionally decrease the rate of separation of detectable species from the vicinity of the reaction. As a result, low potentials offer the greatest sensitivity. One example of low potential is the zero potential mode in which maximum detectable product accumulates and, thus, higher sensitivity.

Higher potentials offer the advantage of speed as the magnitudes, but not relative values, of the rates of migration of the species involved in the assay increase proportionally. High potentials also offer the ability to mix zones rapidly and, for those reactions for which sufficient reaction time and sensitivity are not a concern, to minimize analysis time. Given knowledge of the demands of a given chemical system involved in an assay, one of skill in the art may choose the potential so as to optimize each of the stages involved in the assay. For example, the zonal merging stage may be done at high potential to induce rapid, uniform mixing. However, the ensuing reaction phase may be done at lower potential to allow sufficient time for the reaction to occur and to provide maximum sensitivity. The potential may then be increased to sweep the detectable species past the detector and minimize analysis time.

It is desirable to initiate a chemical reaction by mixing at a rate other than the rate at which the chemical reaction occurs, i.e., the rate at which product forms. Thus, the rate of mixing should be performed either at a substantially higher or lower rate than the rate of the reaction. The rate of mixing of sample and reactant zones may be controlled by varying the electric potential applied to the capillary. For example, when a reaction occurs rapidly, it is desirable either to mix very rapidly so that product formation is uniform across the sample zone, or very slowly so that product formation is complete across the zone as zone engagement occurs. Electrophoretic mixing occurs faster at high potential, and thus mixing at a high potential is preferred. At several thousand V/cm, mixing will occur in milliseconds. The potential then may be decreased or interrupted after mixing to allow the reaction to occur. In addition, because the time interval at high potential is short, little heat is produced.

A unique feature of electrophoretic mixing relative to mechanical mixing methods is that zones are merged by differential rates of migration. Since concentration is always discontinuous across a zone in an electrophoretic system, the concentration of reactants will vary during zonal engagement. A constant rate of engagement of different areas of a zone is desirable. When the zones are Gaussian, leading and trailing edges of the peaks will be of lower concentration than the center of a peak. As the zones are electrophoretically engaged, the zones of low concentration are the first to mix. Thus, the reaction starts at low concentration and the rate of product formation will not be constant across a peak. To simplify interpretation of data, it is desirable to rapidly engage the zones in order to obtain a rate of product formation which approximates a constant rate. For example, when a capillary is filled with reactant and then a small sample containing analyte is introduced, the leading edges of the zones engage slowly relative to the trailing edges, which engage quickly. If the applied potential is abruptly turned off, the leading edges will be electrophoresed past each other while the trailing edges of the zone may then make contact under zero potential. Thus, the relative positions of the zones should be carefully monitored.

(f) Length of Channel/Capillary

The length of the channel or capillary used in combination with the applied potential determines the strength of the electric field and thus also affects the rates of migration of each chemical species. In addition to the overall length of channel or capillary, the separation length, i.e., the length between the point of introduction of the analyte into the channel or capillary and the position at which the product passes by the detection window, is another parameter which affects the assay. The separation length affects the time available to perform the mixing and reaction phases of the assay, as shown in equation (2). For slower reactions performed under uninterrupted potential, a longer separation length is often necessary to allow sufficient time for the reaction to occur before the analyte passes the detector.

The incorporation of a spacer (zone containing non-reactive medium placed between analyte and analytical reagent zones) also allows for the experimental regulation of the pre-reaction separation of analytes. This option is of importance in systems where many analytes within a sample possessing characteristic electrophoretic velocities react with the analytical reagent(s) to form the same detectable species or species with very similar electrophoretic velocities. Within this scheme, the analyte molecules may be allowed to separate into distinct zones which will encounter the reagent zone(s) at spatially and/or temporally distinct location within the capillary. As a result, the detectable species will be formed at unique locations and/or times within the reaction chamber and, therefore, they will be observed at the detection window at a time indicative of the particular analyte responsible for their formation.

(g) Alteration of Kinetics

Kinetic parameters may be altered by the selection of factors such as pH, ionic strength, viscosity, and temperature. Reaction rates are highly dependent on temperature, as described by the Boltzmann Distribution and the activation energy required for a given reaction. The use of a thermostated capillary electrophoresis system allows for the selection of a reaction temperature. Furthermore, the pH and ionic strength of the electrophoretic medium may be varied to determine the direction and rate of reversible reactions. Most enzymatic reactions are reversible and thus demand optimum pH and ionic strength ranges for maximum turnover of analyte substrate. For reactions which are diffusion controlled, the viscosity of the electrophoretic medium may determine the maximal availability of reactant to analyte and, therefore, overall rate of product formation.

Viscosity, pH, and ionic strength also may be used to enhance the sensitivity of methods of the invention by concentrating species at the interface of two zones of different viscosity, pH, or ionic strength. Chemical species may be "stacked" at such interfaces by virtue of their differing electrophoretic mobilities in the two adjacent regions of viscosity, or due to the variability in electric field between the two regions of viscosity. The principles of isotachophoresis may be used in this manner to concentrate samples in capillary electrophoresis systems (Chien and Burgi, 1991, *J. Chromatogr.* 559:141; Aebersold and Morrison, 1990, *J. Chromatogr.* 516:79).

(h) Electrophoretic Medium

The electrophoretic medium is critical in the EMCA as it is responsible for exploiting physical characteristics of the reagent species in order to impart the variability in electrophoretic velocity necessary to perform the physical processes involved in EMCA, as previously described. Those electrophoretic media employed in EMCA parallel those utilized in capillary electrophoresis. Each offers the capability of exploiting unique physical parameters of the reagent species. These electrophoretic media include, but are certainly not limited to, free solution, gels, complexatory agents, partitionary additives, and ampholytic species.

Free solution electrophoresis typically is performed in a buffered medium. Electrophoretic mobility in free solution is determined by the charge density of the given species, as previously noted in equation (3). The parameters of pH and ionic strength are determined by the identity and concentration of the chosen buffered solution. The buffer may alter the degree of ionization of various moieties contained within the chemical components, and thus their electrophoretic mobilities. The electrophoretic medium also affects the zeta potential at the capillary surface and the resulting electro-osmotic flow. The type of electrophoretic medium chosen by one of skill in the art allows for control over the electrophoretic velocities of chemical components of the system. This control extends over the physical processes involved in the methods of the invention. A myriad of inorganic, organic, and biological buffers throughout the accessible pH range have been utilized in capillary electrophoretic systems. Free solution electrophoretic systems have been used to impart variable electrophoretic mobilities in all types of molecules capable of acquiring a charge, including inorganic, organic and biological molecules of numerous classes.

Gel capillary electrophoresis imparts variability in electrophoretic mobility which is based on a chemical species' charge and molecular dimensions. This phenomenon offers a unique selectivity in the control of the physical processes involved in the inventive methods. Gels most commonly used in capillary electrophoresis are polyacrylamide and agarose gels, and can be used to analyze molecules such as peptides, proteins and DNA fragments.

The use of complexatory agents in the electrophoretic medium offers the selective interaction of charged or uncharged reagent species with charged or uncharged solution additives. One of skill in the art may choose a given additive based on its ability to form a complex with an analyte. The complex will then migrate in the electric field with a characteristic mobility. For example, crown ethers and cyclodextrans have been used as additives capable of selectively complexing with chiral compounds.

The use of partitioning media, e.g., the addition of ionic surfactants to produce micellar solutions, provides another method of fine-tuning the analytical methods of the invention. The selective partitioning of species into charged micelles having their own characteristic electrophoretic mobilities allows for the development of differential velocities for neutral species which have no characteristic velocity in free solution. Numerous ionic surfactants have been utilized, including sodium dodecylsulfate (SDS) and bile salts. Micellar phases have been utilized in the analysis of species such as amino acids, drugs and drug metabolites.

The addition of ampholytic molecules to the electrophoretic medium provides a method of fine-tuning an analysis in which the analyte, reactant and product possess only small differences in electrophoretic mobility. Ampholytic molecules are also useful where the species involved in the reaction migrate to a point in the capillary where electronic neutrality exists and, therefore, electrophoretic mobility ceases. The resulting heterogeneous solution can then proceed past the detector.

9. Multi-Analyte Determinations by EMCA

Methods of the invention allow for the substantially simultaneous determination of plural analytes in a sample. Thus, for example, a blood sample may be analyzed simultaneously for many different analytes. The different analytes may possess similar or different electrophoretic velocities, and the plural analytes may move in the electric field with the same or different velocities as the product formed after contact with one or more reactants. Examples of analyses of plural analytes in a sample are as follows.

Analytes A, B, and C react with reactant R to produce or deplete product P. P may be substantially identical for each chemical reaction involving analytes A, B, and C with R. Alternatively, P may be different for each reaction, but may move at the same rate in the electric field and thus be indistinguishable in terms of its electrophoretic velocity.

$$A+R \rightarrow P$$

$$B+R \rightarrow P$$

$$C+R \rightarrow P.$$

Analytes A, B, and C in this example may be distinguished if they possess different and known relative electrophoretic mobilities in the chosen electrophoretic medium. Their distinctive electrophoretic mobilities may be taken advantage of by allowing for electrophoretic separation of the three analytes prior to their engagement with R. Thus, after each separated analyte, A, B, and C, undergoes a chemical reaction with R to produce P, three distinct zones of P will be produced. As each zone of P migrates past the detector, the amount of P detected can be related to the concentration of each of A, B, and C present in the sample.

Analytes A, B, and C may react with the reactant R to produce or deplete three different products $P_A$, $P_B$, and $P_C$. These products either possess a unique detection property or a unique electrophoretic mobility.

$$A+R \rightarrow P_A$$

$$B+R \rightarrow P_B$$

$$C+R \rightarrow P_C.$$

In this example, a pre-reaction separation of analytes is not necessary, nor is it required that the analytes possess different relative electrophoretic mobilities. The distinct electrophoretic detection properties or mobilities of each of products $P_A$, $P_B$ and $P_C$ must be known. The electrophoretic mixing of analytes A, B, and C with reactant R and the chemical reactions may occur simultaneously and/or at the same rate. As each product migrates past the detector, its detected quantity will correspond to the concentration of the corresponding analyte in the sample.

Analytes A, B, and C may react with reactants $R_A$, $R_B$, and $R_C$ to produce or deplete products $P_A$, $P_B$, and $P_C$.

$$A+R_A \rightarrow P_A$$

$$B+R_B \rightarrow P_B$$

$$C+R_C \rightarrow P_C$$

In this example, if the three products do not possess unique detection or electrophoretic properties, then the analytes must possess differing relative mobilities in the electric field and a pre-reaction separation of analytes must be performed. If the analytes migrate at the same rate in the electric field, then they may be analyzed simultaneously if the products possess distinct relative electrophoretic mobilities or distinct detection properties.

12. Apparatus

Figure 7:
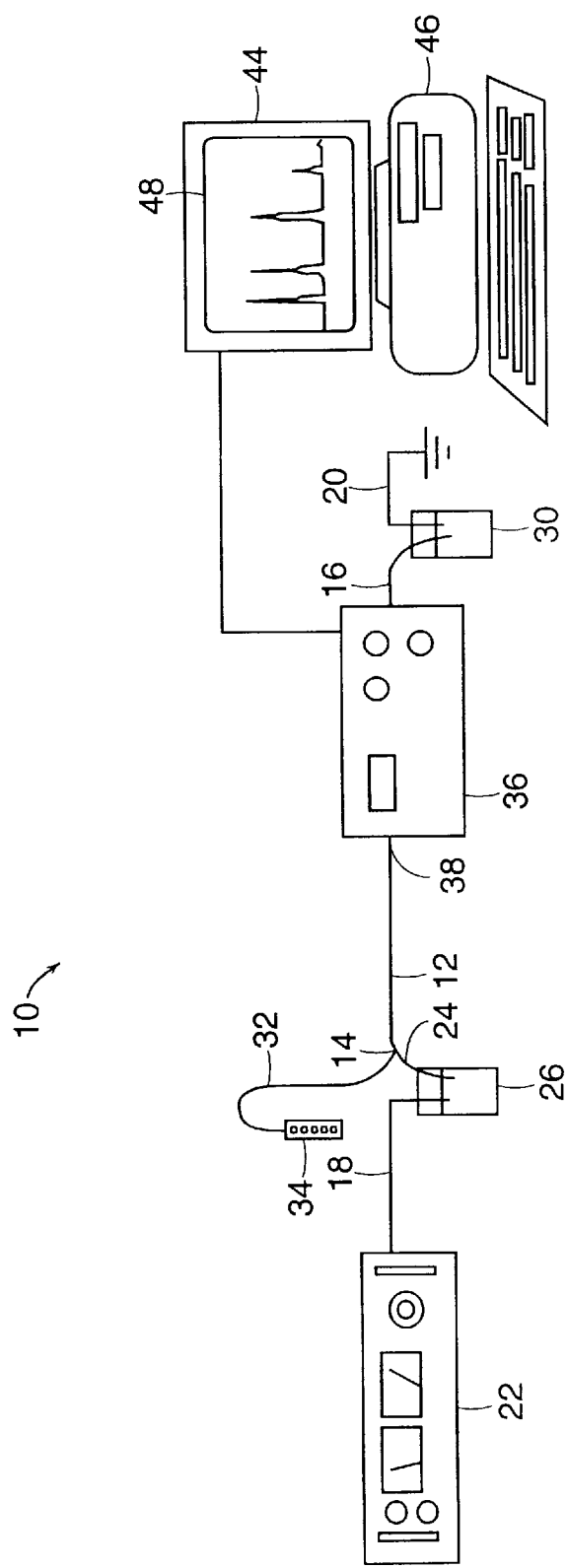
FIG. 7 is a schematic illustration of an apparatus useful for carrying out the methods of the invention.

In FIG. 7, the apparatus 10 includes a capillary 12 with an inlet end 14 and an outlet end 16. The capillary may be a pulled glass tube or any means for electrophoresing microsamples. A charged electrode 18 is in communication with conductive medium 26 and an oppositely charged electrode 20 with conductive medium 30. Electrodes 18 and 20 are electrically connected to a power supply 22. Apparatus 10 also includes a fresh supply of conductive medium 26 which is fed into inlet 14 of tube 12 via conduit 24. The buffer fills the tube and exits through conduit 28 into reservoir 30. The capillary may have a diameter in the range of 1–500 μm, preferably 25–200 μm, and most preferably 75–100 μm. The length of the capillary may be in the range of 1–500 centimeters from the inlet end to the outlet end, preferably 5–100 cm. Capillaries which operate under electric fields of from several hundred volts per centimeter up to several thousand volts per centimeter or more are preferred. See U.S. Pat. Nos. 4,865,706 and 4,865,707, hereby incorporated by reference.

Output from detector 36 is connected to a recorder 44 which is connected to a computer 46. Recorder 44 records data as an electropherogram 48. Sample 34 is introduced into tube 12 via conduit 32. Detector 36 detects chemical components which pass through the tube, e.g., at position 38. Detector 36 may be any detector capable of sensing components of the sample as they traverse capillary tube 12, with which the detector communicates. Detector which operate by sensing change in electromagnetic radiation, such as ultraviolet, infrared, and fluorescence detectors, require that any protective coating of organic material present on capillary tube 24 must be removed over the area of the capillary on which the detector is to operate.

Another on-column method of detection involves detection of a radioactive-labeled component of the reaction, utilizing an appropriately-designed radioactive sensing device. This detection approach could also be employed with off-line collection and subsequent determination.

It is also possible for the detector to operate by directly sensing separated sample constituents as they exit capillary tube 12. Examples of such detectors include mass spectrophotometric detectors and electrochemical detectors. In mass spectrometric detection the outlet end 16 of capillary tube 12 is placed in very close proximity to the inlet of a mass spectrometer and an electrode is also placed in close proximity to this capillary end, in contact with the conductive medium exiting the capillary. The field across the capillary is established between this electrode at the capillary's end and the corresponding electrode or wire making contact with the conductive medium in which the capillary tube inlet end 14 is in contact. In a further alternative detector embodiment, useful where a detector or probe must come into contact with the conductive medium exiting capillary tube 12, the exit end of the capillary tube is connected to a very short additional piece of capillary tube by means of a porous glass sleeve, and this sleeve is immersed in conductive medium. Electrical contacts for the imposition of the electrophoresis field are made with the reservoirs of conductive medium at the respective ends of the capillary tube, and the detector probe is placed in contact with the conductive medium exiting the capillary extension.

An optional programmable computer may communicate with and directs input into an optional waveform generator to control applied potential. The computers may be a single device or two independent devices. The generator may in turn be in communication with and direct input into power supply 22. Electrical output from power supply 22 travels along electrode 18 to conductive medium 26, or along electrode 20 to conductive medium 30.

The programmable computer may be programmed to direct the waveform generator to produce the amplitude or frequency desired in a given electrophoretic chemical reaction. The computer may also direct the movements of an optional automatic sampler, which in turn may direct input or output of the sample to or from the electrophoretic system. For example, the sampler may shunt the inlet end 14 between sample 34 and medium 26 so as to allow sample or medium into the capillary tube.

The waveform generator may be any conventional waveform generator (e.g., Model 75, Wavetech, San Diego, Calif.). The waveform may be run by computer control or in stand-above mode. It is preferably capable of providing a variety of waveforms, including sine waves, square waves, triangular waves, etc., in a positive or negative sense relative to a defined reference voltage.

In operation, apparatus 10 may be used as follows to detect an analyte. For example, where the analyte being determined is the activity of an enzyme, sample containing the enzyme 34 is introduced into capillary 12 at inlet 14 by electrophoresis or siphoning through conduit 32, the substrate is contained within capillary 12. Enzyme and substrate in this example possess charges and electrophoretic mobilities which orient them in opposite directions in the capillary when an electric potential is applied. Power supply 22 is turned on and adjusted so as to deliver an applied potential to the capillary via electrodes 18 and 20. The enzyme and substrate thus begin to migrate in the electric field and product is formed and begins to move toward detector 36, as shown in FIG. 4. When the product reaches detector 36, a signal is transmitted to recorder 44 and computer 46. Electropherogram 48 is then produced, mixed with the reagents in capillary 12 electrophoretically; i.e., each charged component in the tube migrates along the tube according to its charge and thus mixes with other components which migrate at a different rate.

Rapid mixing may be achieved using a post-reaction detector (El Rassi, 1976, *Journal of Chromatography* 559:367) as in liquid chromatography systems (Schlabach et al., 1978, *Clinical Chemistry* 24:1351; Snyder, 1976, *Journal of Chromatography* 125:287; Deelder et al., 1977, *Journal of Chromatography* 125:287). For example, substrate may be added to the system through a mixing-tee (e.g., where conduits 32 and 24 join in FIG. 7) at the inlet end of the capillary tube, and the reaction mixture is then pumped into the capillary tube. Product detection is achieved near the outlet end of the capillary using any conventional capillary electrophoresis detector. Because the transit time between the mixing-tee and the detector is constant, this system may approximate a fixed time assay. Enzyme activity or substrate concentration may be assayed by electrophoresing the product of an enzymatic reaction involving enzyme and substrate to the detector where it is detected. As described herein, under constant potential, the transport velocity of enzyme and product is generally different, and the product may become separated from the enzyme immediately after it is formed.

Apparatus useful for conducting assays involving a competitor having a biorecognition moiety may be similar to the devices described above. That is, the channel of the device may be a simple capillary tube and the entire apparatus may be represented by an embodiment as shown in FIG. 7.

In one of its simplest forms, an analytical device of the invention comprises a channel, with the channel containing an electrophoretic medium and a first reactant for reacting with a second reactant portion of a competitor as previously described. It is contemplated that this analytical device may be part of a diagnostic kit specific for a particular analyte or group of analytes. Upon obtaining a specimen for analysis, a binding reaction is conducted in a vessel, followed by introduction of a sample from the reaction vessel into the channel. The analytical device may be placed in an electrophoresis apparatus, either before or after introduction of the sample into the channel. Subsequently, an electric potential is applied, the molecules in the channel begin to migrate and the second reactant portion of the competitor, usually an enzyme, will react or catalyze the production of detectable product. The detectable product then migrates along the channel past a detector and is detected. If a quantitator is present, the detectable product can be quantified by a quantitator known to those skilled in the art. Typically the quantitator will be a computer interfaced with the apparatus. The manipulation of the input signal from the detector and the presentation of results will be known to those skilled in the art. The use of a quantitator will provide accurate and rapid results in the desired format. The channel may be a capillary as previously described or a flow system as part of a microchip.

The analytical device may comprise a sample injection zone for conducting a binding reaction, and a channel. Again, this device is contemplated to be part of a diagnostic kit. If the assay is to be homogeneous, no immobilized reactants will be present. A competitor or competitors may be present. However is the assay is to be heterogeneous, an immobilized reactant will be present in the sample injection zone. The device may have a competitor in addition to an immobilized reactant in the sample injection zone to mix with a sample introduced to the sample injection zone. The device may have a separation zone. Some devices may comprise a sample incubation zone. Similar apparatus are disclosed in U.S. patent application Ser. No. 08/726,093, filed on Oct. 4, 1996, which is owned by a common assignee of this invention and is herein incorporated by reference.

Figure 8:
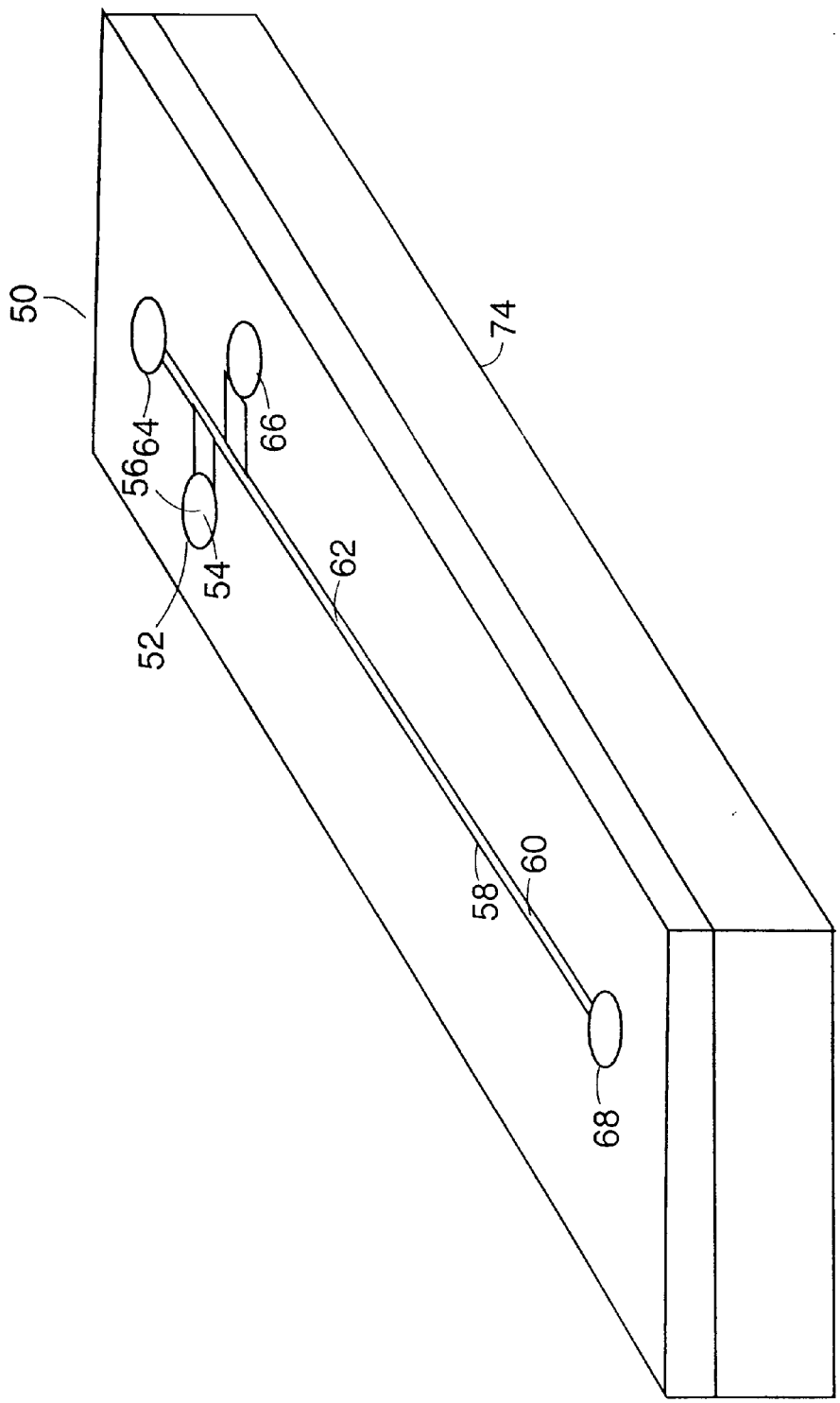
FIG. 8 is a schematic representation depicting a sectional view in the plane of a channel of an analytical device of the invention.

Referring to FIG. 8, a more preferred apparatus 50 comprises a sample injection zone 52. One or more immobilized reactants 54 and competitors 56 are disposed within the sample injection zone 52, such that, upon introduction of the sample into the sample injection zone 52, the immobilized reactants 54 and competitors 56 come into contact with a sample introduced to the sample injection zone 52. Preferably the immobilized reactants 54 are immobilized antibodies. The apparatus further comprises a channel 58 having disposed therein an electrophoretic medium 60 and a first reactant 62. The channel 58 is in communication with the sample injection zone 52, a buffer reservoir 64, an injection/waste reservoir 66, and a waste reservoir 68. Fluid communication typically exists between these zones. In certain embodiments, the junction of the sample injection zone 52 with the channel 58 is upstream from the junction of the injection/waste reservoir 66 with the channel 58. This offset design allows a larger injection volume to be realized.

Figure 9A:
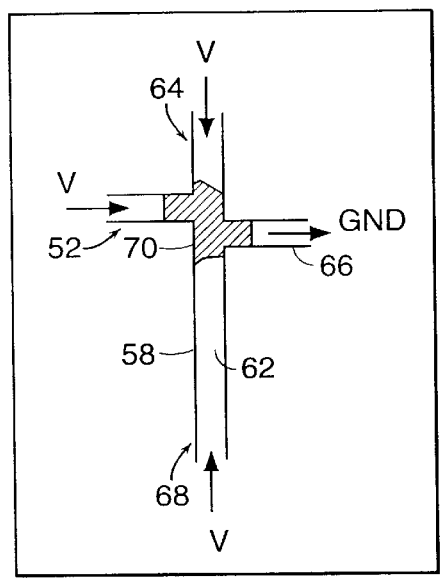
FIGS. 9(a) and 9(b) are schematic representations depicting (a) a sample loading process and (b) an electrophoretic separation process with an offset pinched injector.
Figure 9B:
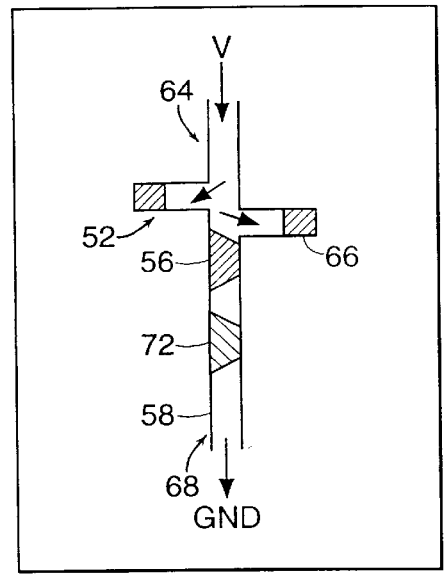

Referring to FIG. 9, panel A, the operation of one possible system configuration for a heterogeneous assay is described. An analyte is added to the sample injection zone 52, and a binding reaction occurs leaving unbound competitor 56 present in the sample injection zone 52. A voltage (V) is applied to the zones 64, 52 and 68 relative to the ground (GND) applied to zone 66 and is controlled to pinch off the flowing sample stream, preventing diffusion of sample 70 into the channel 58 providing an injection volume which is independent of sampling time. The electrical potential between zones 64, 52, 68 and 66 is then shut off, and a potential is imposed between zone 64 and zone 68 to migrate unbound competitor 56 into the channel 58 containing a first reactant 62. As shown in FIG. 9, panel B, control of the applied voltage will allow separation by size and electrophoretic mobility of, for example, the competitor 56 and a detectable product 72 formed from the reaction of the first reactant 62 and a second reactant portion on the unbound competitor 56. As described previously, the apparatus may be operated in a continuous mode, i.e., the electric potential continuously is applied, or in a "stop-flow" mode wherein the channel 58 is subjected to zero potential for sufficient time to permit the increase in the amount of detectable product 72.

The apparatus may be disposed in contact with a temperature controlling means 74 (FIG. 8). The temperature controlling means 74 can be activated to control the temperature at which the assay is performed providing further control over the reaction conditions and kinetics.

Figure 10:
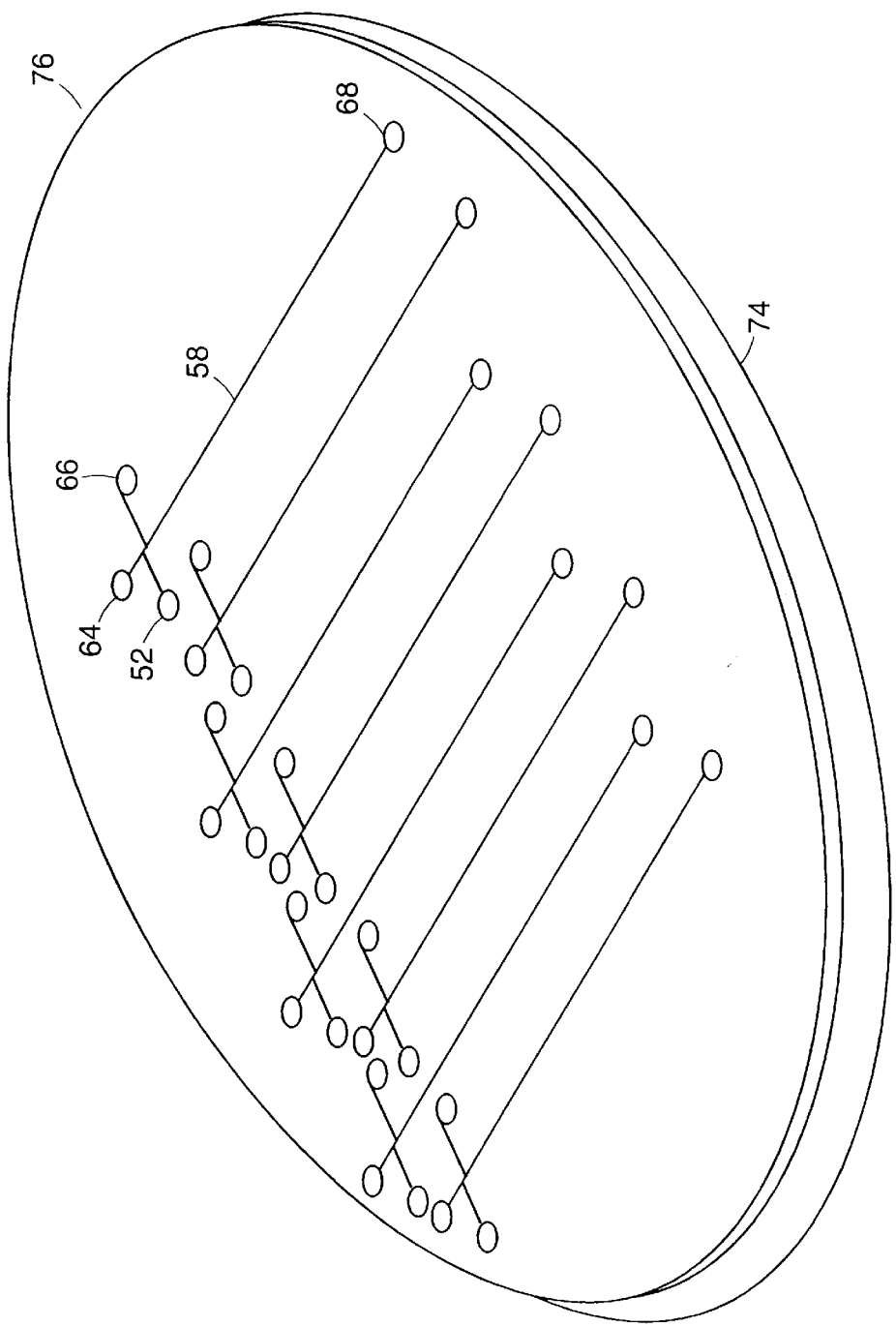
FIG. 10 is a schematic representation depicting a sectional view in the plane of channels of a multichannel chip of a preferred analytical device of the invention.

The apparatus also may be a chip such as a microchip having multiple parallel channels formed in solid substrates. Such devices allow many separate analyses to be performed in parallel, achieving a high throughput. Referring to FIG. 10, the apparatus 76 comprises multiple capillary channels 58 each having a sample injection zone 52, a buffer reservoir 64, an injection/waste reservoir 66, and a waste reservoir 68. The apparatus may be disposed in contact with a temperature controlling means 74. Any known detection means may be utilized in the apparatus of the invention, and can easily be selected by one skilled in the art. When utilized in accordance with the methods and compositions of the instant invention, the apparatus permits qualitative and quantitative detection of an analyte, competitor, analyte-competitor complex or detectable product.

A microfluidic system, e.g., a microchip of the invention, usually is constructed of a solid substrate. The microfluidic system can be fabricated using micromachining techniques similar to those used in the microelectronics fabrication industry. For example, a microchip separation device can be made using photolithography combined with chemical etchants to form channel structures in a solid substrate, e.g., fused silica wafers. The depth of etching and thus, the size of the channel, can be controlled by monitoring the etching time and measuring the depth of the channel. Access holes are laser drilled at channel terminals through the etched wafer. A second wafer is bonded to the etched wafer to produced enclosed channels if so desired. After bonding, the wafer may be cut into individual separation chips depending upon its intended application.

Solid substrates for microfluidic systems may be any material suitable for that application such as glass or silica. However, the microfluidic device also may be made from a suitable polymeric material such as polystyrene. A microfluidic device made of a polymeric material permits the use of an inexpensive molded part in the complete system thereby reducing the cost per test.

Figure 11:
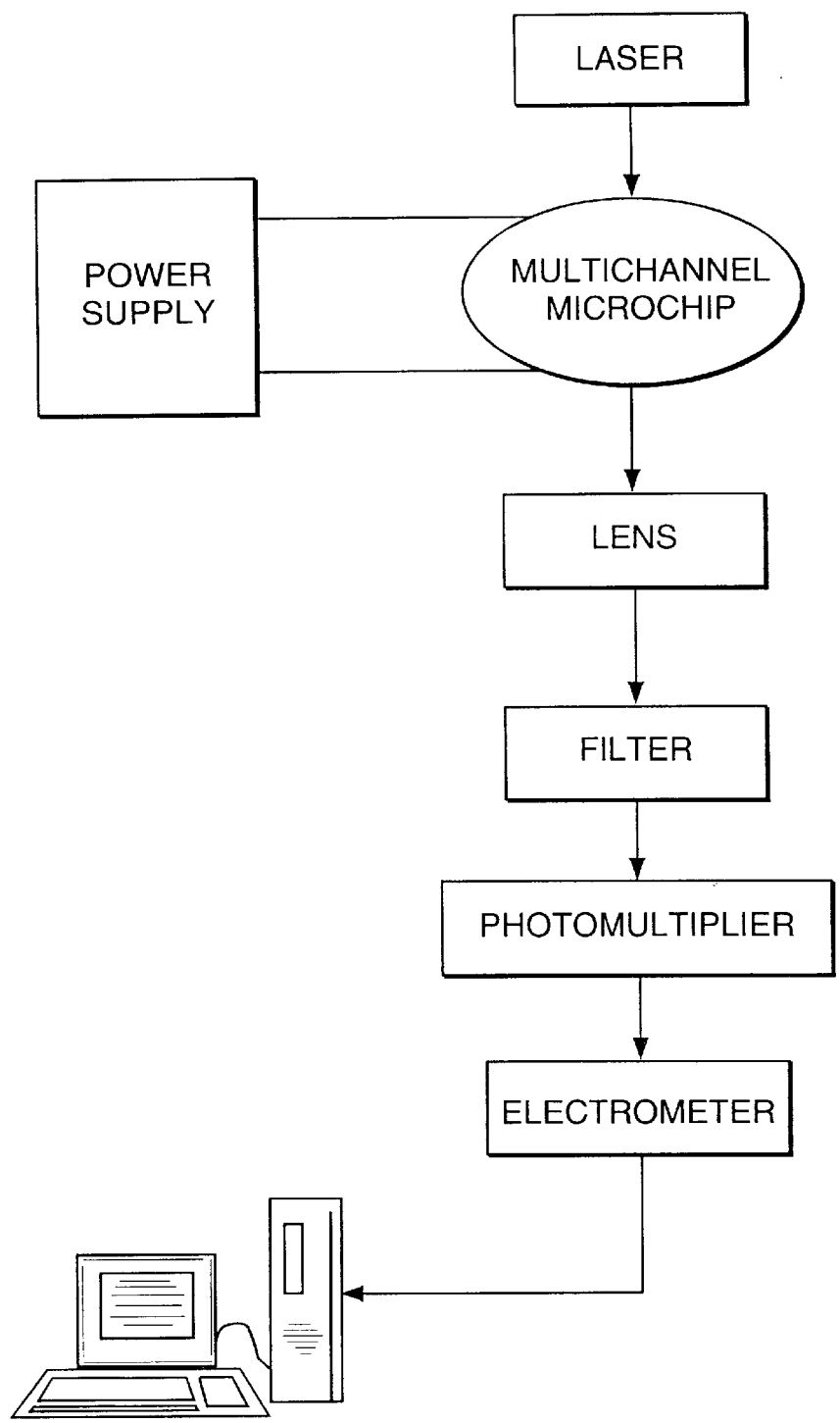
FIG. 11 is a schematic representation of an integrated apparatus for conducting multichannel chip analyses of the invention.

Referring to FIG. 11, a fused silica microchip may be coupled with a power supply and fluorescence optics for the chip-based assay. High voltage may be provided by a Spellman CZE 1000R power supply (Plainview, N.Y.) or other suitable supply through a switching circuit and resistor network. Laser-induced fluorescence detection may be performed using an Omnichrome (Chino, Calif.) argon ion laser, or other suitable device. A microscope objective may be used to collect the fluorescence emission. The collected light may be spatially filtered by an aperture in the image plane and optically filtered by bandpass filters. A photomultiplier tube, such as Hamamatsu R928 (Bridgewater, N.J.), connected to an electrometer, such as a Keithley 614 (Cleveland, Ohio) can detect the fluorescence signal. The signal may be digitized with a PC-controlled data acquisition system, such as a Data Translation 2804 (Marlborough, Mass.) and analyzed using appropriate software, such as Caesar software from ADI (Alameda, Calif.).

A major advantage of the microfabrication technique compared to conventional capillary tubes is the ability to construct channels structures with channel junctions so that multiple streams of fluid can be brought into contact. In the present invention, a first reactant, e.g., an enzyme substrate can be introduced into a channel at a different point than the introduction of a sample containing a competitor having a second reactant portion, e.g., an enzyme. Thus, greater control over the timing and location of the reaction between the first reactant and the second reactant portion is possible. In addition, the zone of the binding reaction can be separated from the zone of amplification to provide greater flexibility in the design of the assay procedure.

13. Preparation of Capillary

The capillaries employed in the invention typically are uncoated. However, coated capillaries may be used. The coated capillaries may be constructed of silica which is coated on the outer surface with an agent, such as polyimide, to prevent breakage due to the fragile nature of silica. While there are no inherent limitations on the lengths or inner diameters of capillaries employed in the invention, typical lengths range from 5 to 100 cm. A capillary tube having a diameter of between 10 and 500 μm is useful in the invention.

In the methods of the invention, it is frequently advantageous to use capillary coatings. These coatings offer several advantages to the use of uncoated silica. The ionization of silanol groups produces a negatively-charged silica surface. Positively-charged analytes, such as proteins, adsorb to the negatively-charged wall thereby altering the zeta potential at the silica/solution interface. Disruption of the zeta potential alters the electro-osmotic flow and may decrease reproducibility and reduce recovery of product. Variability in electro-osmotic flow is particularly detrimental in quantitative analyses because the area of a peak observed in capillary electrophoresis is inversely proportional to the electrophoretic velocity of the species. Any variation in electro-osmotic flow will produce a concurrent alteration in peak area. Capillary surface modification may also be useful for controlling electro-osmotic flow. The ability to regulate the electro-osmotic flow serves as a powerful tool for carrying out in the invention. The process of electrophoretic mixing of zones as well as the transport of the detectable product to the detector is dependent upon the electrophoretic velocities and, therefore, the electro-osmotic flow of the system.

Those coatings which have been employed in capillary electrophoresis include the covalent modification of the silica surface as well as the use of buffer additives to dynamically modify the capillary wall. Representative examples of the covalent modification technologies include epoxy polymers (Towns et al., 1992, *J. Chromatogr.* 599:227), polyethylene-imine (Towns and Regnier, 1990, *J. Chromatogr.* 516:69), aminopropyl-silylated coatings (Moseley et al., 1991, *Anal. Chem.* 63:109), polyacrylamide (Cobb et al., 1990, *Anal. Chem.* 62:2478; Hjerten, 1985, *J. Chromatogr.* 471:429). Representative examples of the use of dynamic coatings include amine additives (Lauer and McManigill, 1986, *Anal. Chem.* 58:166; Nielsen et al., 1989, *Anal. Biochem.* 177:20), cationic polymers (Wiktorowicz and Colburn, 1990, *Electrophoresis* 11:769), and a cationic fluorosurfactant (Emmer et. al., 1991, *J. Chromatogr.* 547:544). Covalent modification coupled to adsorbed dynamic coatings has also been utilized, such as in the use of nonionic surfactants adsorbed to silane-derivatized surfaces (Towns and Regnier, 1991, *Anal. Chem.* 63:1126).

14. Detectors and Detection Methods

Any conventional method of detection may be used in the invention, including those used in conventional capillary electrophoresis methods. A detection method may be chosen which allows for detection of any physical property of a chemical species. These detection systems include, but are not limited to, absorbance of ultraviolet or visible radiation, fluorescence, chemiluminescence, refractive index, Raman, mass spectrometry, electrochemical, and conductivity. Detection of the electrophoretically transported product may occur at a discrete position along the length of the capillary, off-line, or by imaging the entire length of the capillary (Wu et al., 1992, *Anal. Chem.* 54:219), hereby incorporated by reference.

15. Injection Methods

The sample or reactant volumes may be introduced by any of the methods employed in capillary electrophoretic systems, including hydrodynamic, electrokinetic, vacuum, injection port, and syringe methods. Furthermore, the system can be readily automated for injection with commercially available autoinjectors.

16. Preferred Embodiments of the Invention

The invention features an ultramicro method for performing chemical reactions in order to assay an analyte in a sample, e.g., enzyme activity or substrate concentration in a sample. The enzyme may be present in the sample, and the conversion of substrate monitored as an indication of the presence of enzyme in the sample. Alternatively, the substrate may be present in the sample, and enzymatic activity (e.g., the utilization of cofactor or the inactivation of enzyme) may be monitored to indicate the presence of substrate. An assay for enzyme activity is carried our under saturating concentrations of substrate, whereas an assay for substrate concentration is carried out under saturating conditions of enzyme. The assay may be performed in a deactivated fused silica capillary in a capillary electrophoresis apparatus, such as that shown in FIG. 7.

EXAMPLES

The results presented below demonstrate that small quantities of enzyme or competitor having a biorecognition moiety attached to an enzyme may be detected in a capillary zone electrophoresis system by performing the enzyme assay in the capillary according to the methods described herein. Assays rely on the differing transport velocities of the enzyme(s), competitor(s), analyte-competitor complexes, reagent(s), and product(s) under applied potential, a characteristic which may be used to both electrophoretically mix the reactants and electrophoretically separate the enzyme, competitor and/or analyte-competitor complex from product. Product is transported through the capillary tube until it reaches the detector, where its concentration is determined and related to the activity or concentration of enzyme, competitor or analyte-competitor complex in the sample. The detection limit according to the method of the invention appears to be three orders of magnitude more sensitive than the detection limit of conventional assays.

Example 1 demonstrates the use of an enzymatic reaction to catalyze formation of a detectable product in a capillary electrophoresis format. Example 2 demonstrates a method of the invention where a competitor having a biorecognition moiety is involved in a heterogeneous competitive immunological reaction prior to subjecting an aliquot of the immunological reaction solution to enzyme amplified capillary electrophoresis analysis.

1. Analysis of the Enzyme Glucose-6-phosphate dehydrogenase

The enzyme Glucose-6-phosphate dehydrogenase (G-6-PDH, EC 1.1.1.49) may be used as a representative enzyme for analysis according to the invention. G-6-PDH has been found in almost all animal tissues and microorganisms, and catalyzes the first reaction in the hexose monophosphate shunt pathway. The clinical biochemistry of G-6-PDH deficiency has been extensively reviewed (Yoshida, 1973, *Science* 179:532).

Glucose-6-phosphate dehydrogenase (G-6-PDH), also referred to as D-glucose-6-phosphate:NADP oxidoreductase, was chosen to examine ultramicro enzymes assays because this enzyme may be readily assayed spectrophotometrically (Sigma diagnostics procedure No. 345-UV, 1990). G-6-PDH oxidizes glucose-6-phosphate (G-6-P) to 6-phosphogluconate (6-PG) while reducing nicotinamide adenine dinucleotide phosphate (NADP) to its reduced form NADPH in the presence of G-6-P.

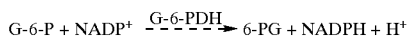

Figure 12:
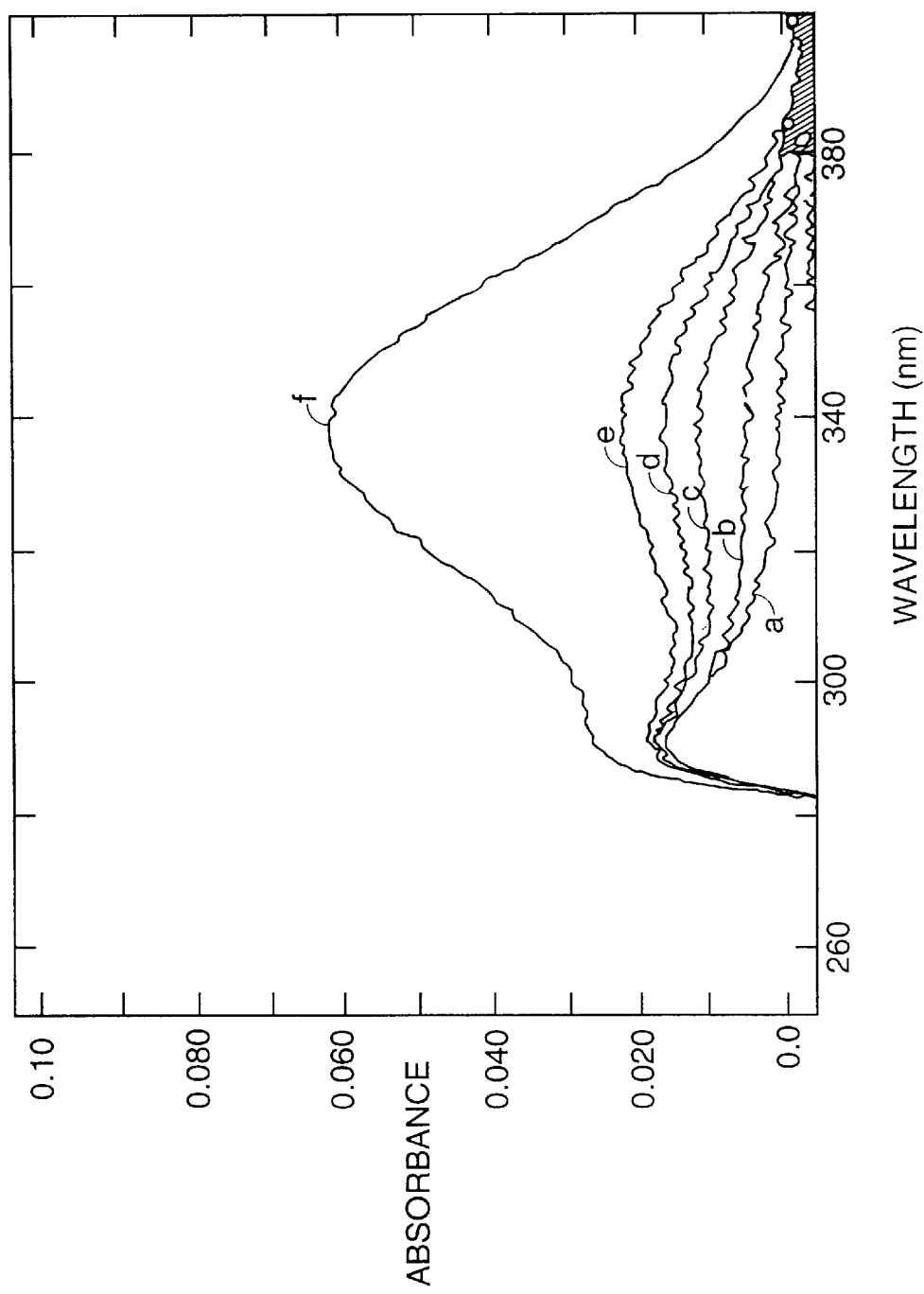
FIG. 12 shows an increase in absorbance of NADPH at 340 nm (a) 2, (b) 4, (c) 6, (d) 8, (e) 10 and (f) 28 minutes at zero potential.

The absorbance spectrum of the product NADPH is uniquely different than that of either the G-6-PDH or the running buffer. NADPH has an absorption maximum at 340 nm ($\xi = 6.22 \times 10^6$ cm$^2$/mole). The enzyme 6-phosphogluconate dehydrogenase (6-PDH) can interfere, such as in serum samples contaminated with 6-PGDH from erythrocytes which contain no G-6-PDH. In the presence of 6-PGDH, 6-phosphogluconic acid may be further oxidized to produce a second mole of NADPH. Addition of maleimide to the incubation mixture will inhibit 6-PGDH. FIG. 12 shows an increase in absorbance at 340 nm of NADPH after (a)2, (b)4, (c)6, (d)8, (e) 10 and (f) 28 min. at zero potential.

The method of the invention described in this example is be carried out using any conventional capillary electrophoresis system, e.g., those described in the U.S. Patents incorporated by reference above. A preferred capillary electrophoresis apparatus is an ISCO 3850 capillary electrophoresis system (Instrument Specialties Company, Lincoln, Nebr.). This system may be interfaced to a personal computer using the software "Inject" (Bioanalytical Systems, Lafayette, Ind.) to collect and process data. Another preferred capillary electrophoresis system is constructed using polyamine-coated, fused silica capillaries (Polymicro Technologies, Phoenix, Ariz.) of 50 $\mu$m inner diameter, 360 $\mu$m optical density (OD), and 35–60 cm in length to prepare the columns. The separation length is varied from 15–40 cm. Detection is achieved with a variable wavelength UV absorbance detector (Model V4, Instrument Specialties Company, Lincoln, Nebr.). Protein elution is monitored at 200 nm and the product is monitored at the appropriate wavelength; e.g., NADPH is monitored at 340 nm. The neutral marker mesityl oxide is detected at 254 nm. Strip chart recordings are obtained with a Linear 2000 recorder (Linear, Reno, Nev.).

Reagents, e.g., substrates, cofactors, enzymes, or markers may be obtained from any pharmaceutical or chemical company, e.g., Sigma Chemical Co. (St. Louis, Mo.), Aldrich (Milwaukee, Wis.), or Calbiochem (San Diego, Calif.). In the example described in detail herein, Glucose-6-phosphate dehydrogenase reagent and G-6-PDH substrate solutions were purchased from Sigma Chemical Co. Reagents were prepared and the assay carried out as described in Lohr et al., Glucose-6-Phosphate Dehydrogenase, in: H. U. Bergmeyer (ed.), *Methods of Enzymatic Analysis*, 2nd English edn., Verlag Chemie, Weinheim and Academic Press, New York, 1974, pp. 636. Ethyleneglycol diglycidylether (EGDE), 3-glycidoxypropyltrimethoxysilane (GOX), 1,4-Diazabicyclo[2.2.2]-octane (DABCO), mesityl oxide, solvents and buffers were obtained from Aldrich Chemical Co. (Milwaukee, Wis.). Buffers were prepared with deionized, double distilled water.

Protein samples may be injected into the capillary electrophoresis apparatus by syphoning. The inlet end of the capillary may be inserted into the protein sample and raised approximately 5 cm for 5 seconds. Neutral marker is introduced into the capillary in the same way. The running buffer may contain all of the reagents necessary to assay enzyme activity. Assay reagents are reconstituted according to the reagent supplier (Sigma Chemical Co., St. Louis, Mich.) (Jorgenson et al., 1982, *Analytical Chemistry* 53:1298). For example, for the G-6-PDH assay described herein, the buffer solution contained 0.7 mmol/L glucose-6-phosphate (G-6-P), 0.5 mmol/L of the coenzyme nicotinamide dinucleotide diphosphate (NADP) and 4 mmol/L maleimide, in addition to a stabilizer and lysing agent. Operating current was controlled within the range from 35 to 50 $\mu$A by limiting the applied potential, and was not operated above 60 $\mu$A. All assays were carried out at ambient temperature without temperature control Capillaries were cleaned by flushing with 0.01 M sodium hydroxide, double-distilled water, and then the working buffer solution.

Deactivation was achieved using a covalently bonded epoxy polymer layer. This coating has been shown to give greater than 95% recovery of proteins in capillary electrophoresis. Electro-osmotic flow in these deactivated capillaries is substantially reduced and negatively charged species, such as NADPH, can require 20–30 min. to pass through a 30 cm capillary. Because G-6-PDH has a relatively high pI value, it is transported quickly. The electrophoretic mobility of G-6-PDH and NADPH were found to be 5 and 18 min. respectively.

A capillary zone electrophoresis system was used in which the buffer tanks and capillary had been filled with running buffer containing all of the reagents necessary for the assay except the enzyme. Sample enzyme was introduced into the capillary by injection and potential was applied to initiate electrophoretic mixing of the enzyme and substrate. Product formation was measured with a UV detector at 340 nm. Assays were carried out separately under a constant potential mode, in which the reactants remained under constant potential throughout the time-course of the assay, and a zero potential mode, in which the separation of reactants was stopped during part of the assay.

Figure 13A:
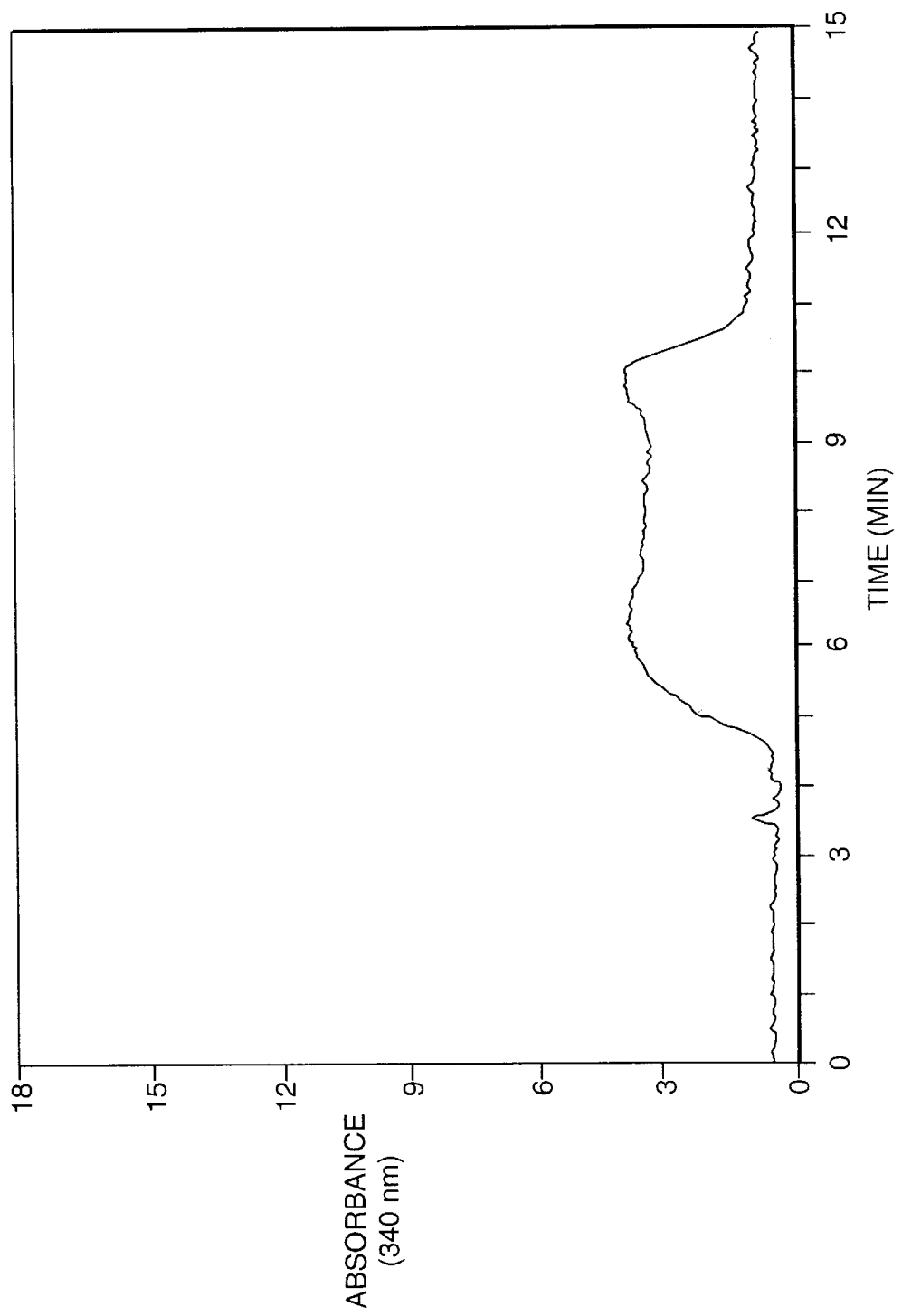
FIGS. 13(a) and 13(b) are electropherograms produced for the analysis of G-6-PDH at (a) high potential, and (b) low potential.
Figure 13B:
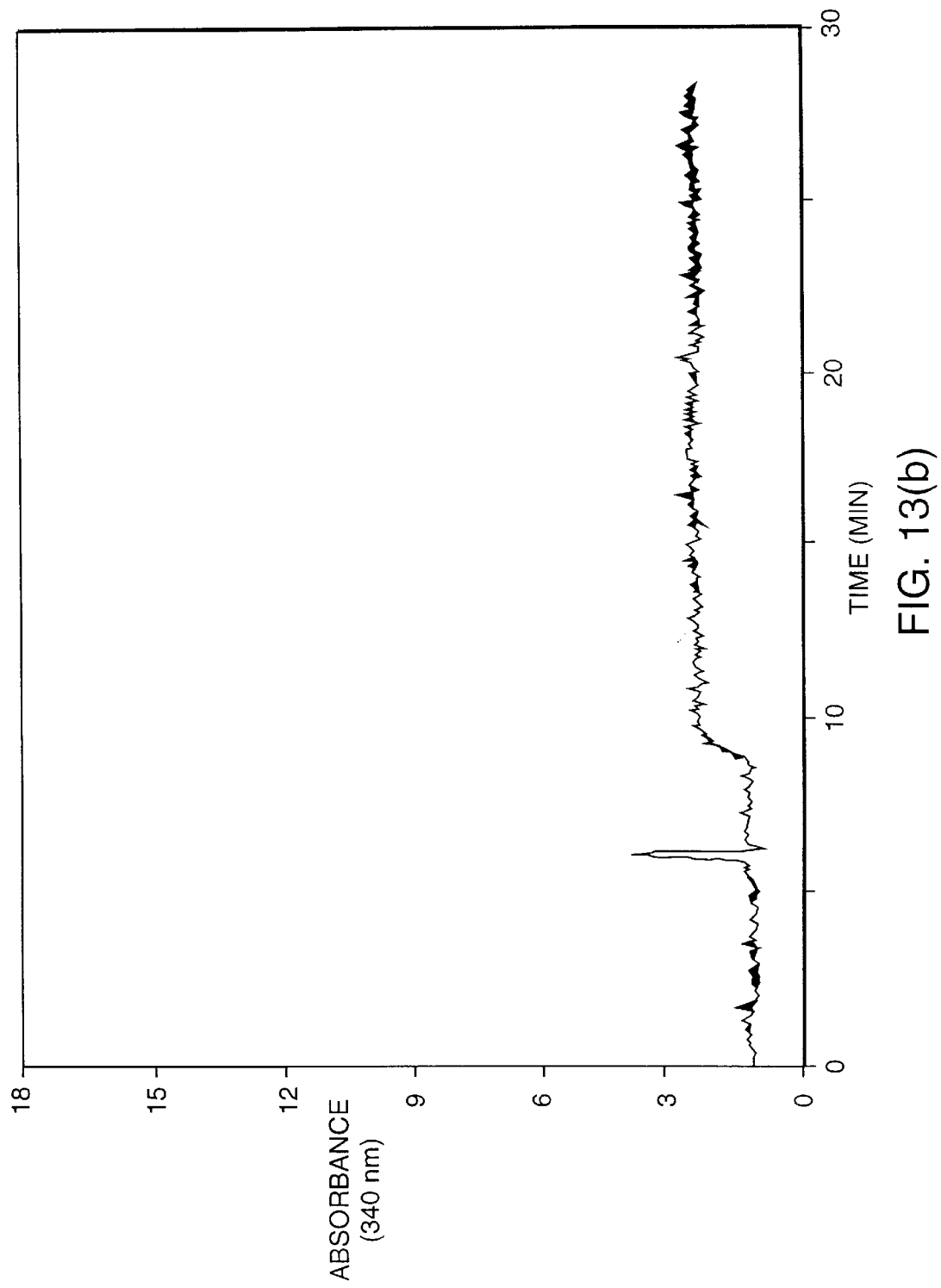

The electropherogram in FIG. 13(*a*) of a G-6-PDH assay obtained under constant potential has the general shape for an enzyme having a greater transport velocity than the product of the reaction it catalyzes. The total time required for the assay in this case is slightly less than 12 min. When a longer capillary was used with a more dilute solution of enzyme, FIG. 13(*b*) shows that plateau height is lower and the elution time of the enzyme is longer. Data collection was terminated in this case before the trailing injection artifact peak eluted. (The height of the injection artifact peak was variable and of no analytical value.) The size of the injection artifact peak was found to be related to three factors: the size, volume and degree of mixing during the injection; enzyme concentration in the sample; and the time elapsed between injection and the start of electrophoresis.

Figure 14A:
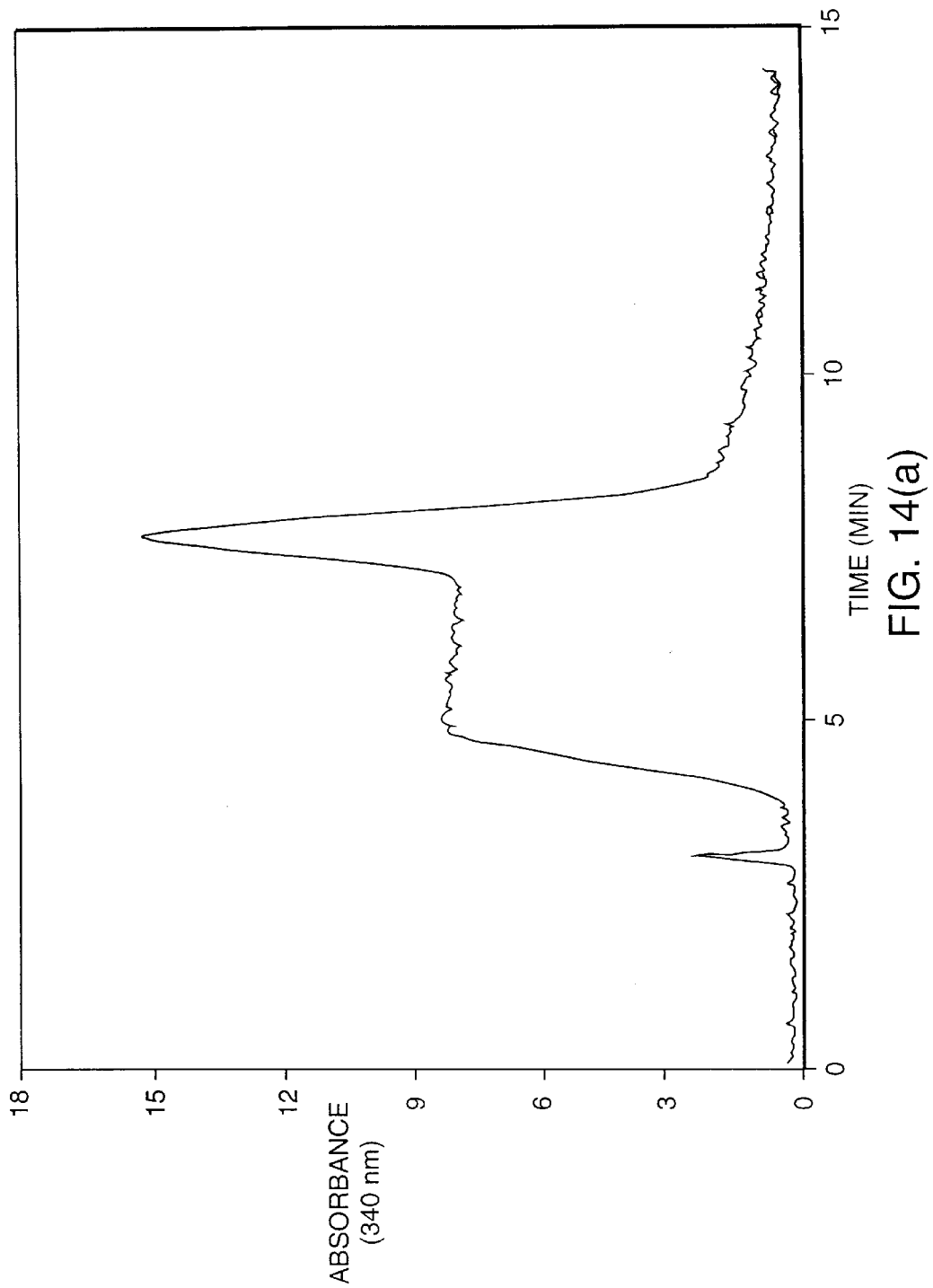

An example of an electropherogram in which several minutes was allowed to elapse between injection of the sample and the start of electrophoresis is shown in FIG. 14(*a*). For comparison, the electropherogram shown in FIG. 14(*b*) was produced as a results of an assay in which sample was injected quickly and the potential dropped to zero for several minutes before the enzyme passed the detector. The large peak at approximately 8 min. is the result of a several minute interruption in the potential, 5 min. into the run.

Analysis time also could have been decreased below 12 min. without loss in sensitivity by shortening the capillary. The optimum length in terms of minimizing analysis time would be the length required for the product elution curve to plateau. Increasing the potential to shorten analysis time was found to be counter-productive, as increasing the potential diminishes product accumulation and sensitivity.

The small peak eluting at 3.5 min. and 6.0 min. in FIGS. 10(*a*) and 10(*b*), respectively, adsorbed at 200 and 340 nm, and may be a protein in the sample that either adsorbs at 340 nm or binds NADPH but does not play a role in catalysis.

Figure 15:
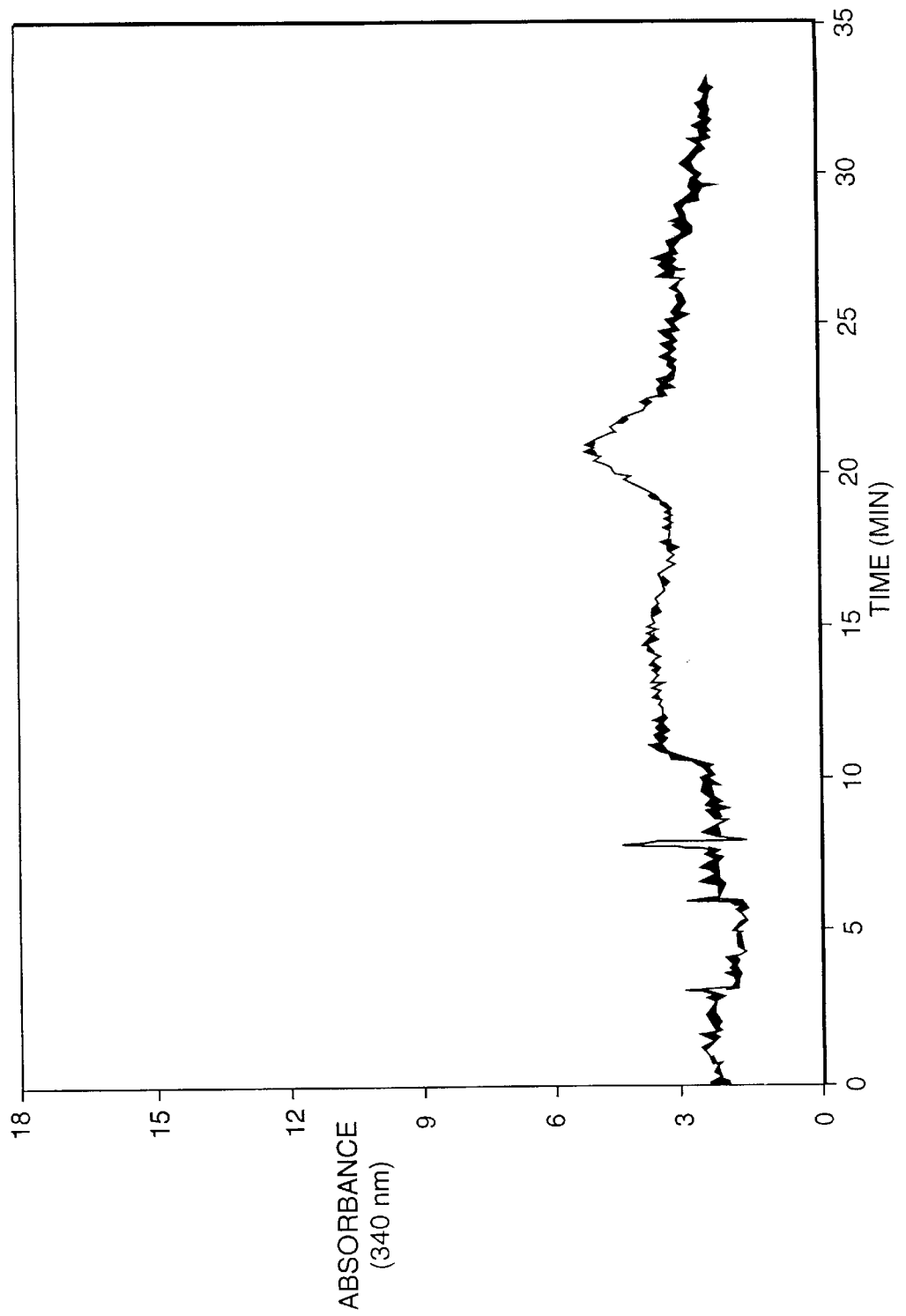
FIG. 15 is an electropherogram which shows accumulation of NADPH by switching to zero potential.
Figure 16:
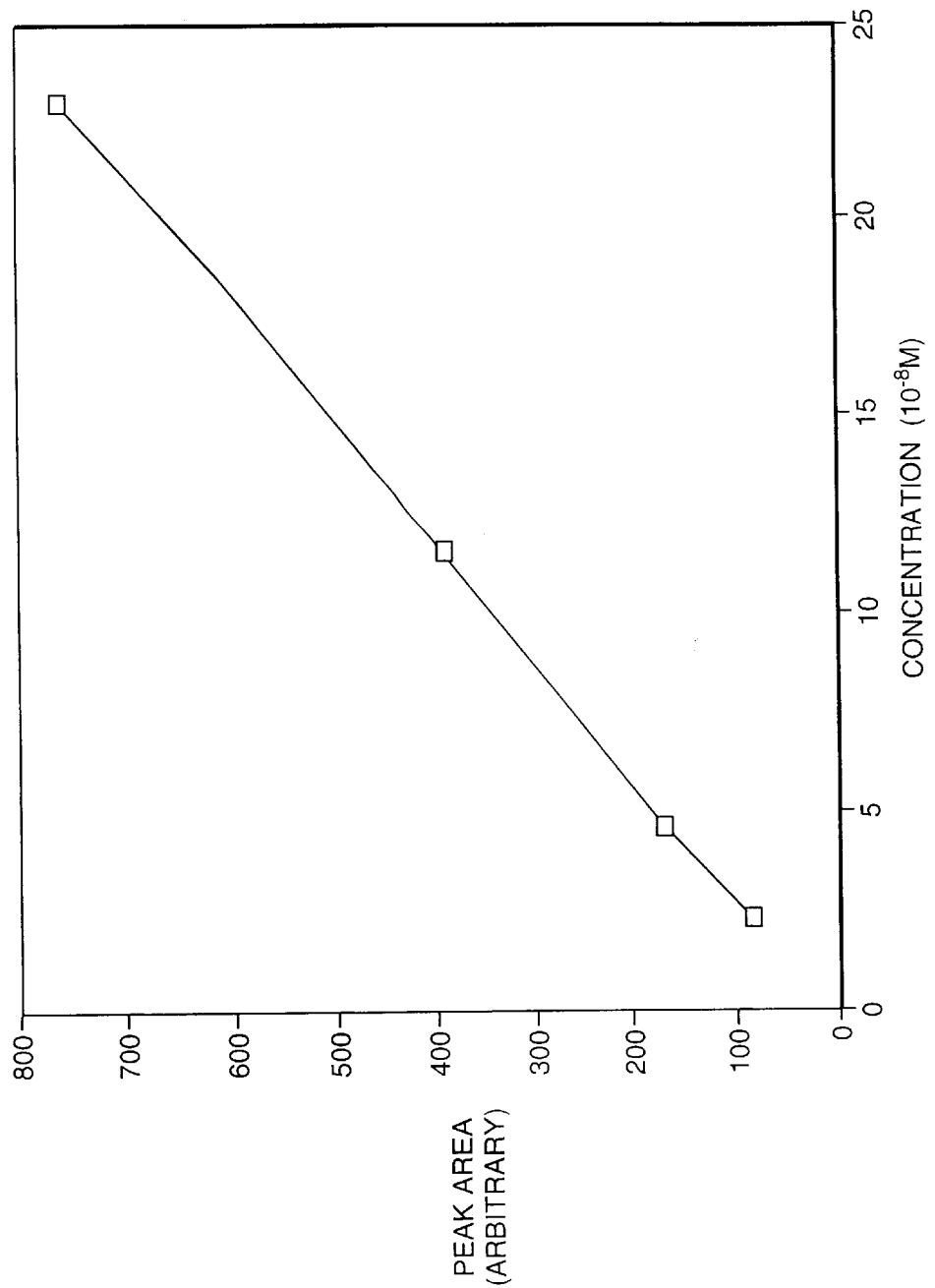
FIG. 16 is a plot of the relationship between the peak areas of detected NADPH product and the corresponding concentrations of the G-6-PDH analyte.

Switching the potential to zero before the enzyme elutes from the capillary allows one to increase the incubation time and thus the sensitivity. Zero potential assays were carried out in a 41 cm segment of capillary for a zero potential pause of up to approximately 6 min. The potential was interrupted after 3 min. and held at zero potential for 5 min., after which the potential was returned to 8700 V for product elution. An electropherogram of a sample estimated to contain $4.6 \times 10^{-17}$ moles of G-6-PDH is shown in FIG. 15. This estimate is based on the assumption of a 2 nL injection volume. Note the peak at 20 min. which resulted from the 5 min. zero potential incubation. The dose-response curve for G-6-PDH using this assay procedure is seen in FIG. 16. Data for this Figure were obtained from Table 1. The G-6-PDH assay shown in Table 1 was performed using a 17.8/41 cm GOX-EDGE coated capillary (50 μm internal diameter). The power supply was set at 8700 volts, 50 mA. Sample was injected by raising the cathode end of the capillary tube for 10 seconds. Detection was carried out at 340 nm at a sensitivity of 0.02 au. Quantitation is based on determinations of the peak area above the constant potential product plateau in the electropherogram. A solution containing one unit/mL of G-6-PDH is approximately $3 \times 10^{-8}$ M. No attempt was made to determine the linear dynamic range of the assay, but similar macroscopic assays suggest that it may be two orders of magnitude (Sigma diagnostics procedure No. 345-UV, 1990).

TABLE 1

G-6-PDH ACTIVITIES OBTAINED BY CAPILLARY ELECTROPHORESIS ASSAY

| Assay Number | G-6-PDH activity | G-6-PDH concentration (Molar) | Quantity of G-6-PDH (moles) | Peak Area (Arbitrary) |
|---|---|---|---|---|
| 1 | 0.75 | $2.3 \times 10^{-8}$ | $4.6 \times 10^{-17}$ | 85,241 |
| 2 | 1.50 | $4.6 \times 10^{-8}$ | $9.2 \times 10^{-17}$ | 164,554 |
| 3 | 3.75 | $1.15 \times 10^{-7}$ | $2.3 \times 10^{-16}$ | 386,763 |
| 4 | 7.50 | $2.3 \times 10^{-7}$ | $4.6 \times 10^{-16}$ | 760,207 |

2. Analysis of Triiodothyronine

Triiodothyronine (3,3',5-triiodo-L-thyronine; "T3") and thyroxine ("T4") are the two active thyroid hormones found in the bloodstream. Approximately 20% of circulating T3 is derived from direct synthesis and secretion by the thyroid gland, while 80% is produced by deiodination of T4 in peripheral tissues (Larson, *Metabolism,* 21:1073–1092 (1972)).

T3 is transported through the peripheral blood stream primarily bound to serum proteins, specifically Thyroxine Binding Globulin ("TBG"), Thyroid Binding Prealbumin ("TBPA") and Albumin. Only about 0.3% of the total serum T3 is unbound and free to diffuse into tissues to exert its biological effects. T3 has its primary influence on the rate of oxygen consumption and heat production in virtually all tissues. The hormone also plays a critical role in the growth, development and sexual maturation of growing organisms. The determination of total T3 is one parameter used in the differentiation and clinical diagnosis of thyroid diseases, particularly hyperthyroidism (Sterling, et al., *Annual Review of Physiology,* 39:349–371 (1977)).

T3 was assayed from serum, a complex biological sample mixture, using the methods of the invention. The T3 assay is a competitive assay. T3 in the sample competes with T3-Alkaline Phosphatase ("T3-ALP conjugate") for antibody binding sites on a well coated with an anti-T3 monoclonal antibodies. Since the number of binding sites is limited, as more sites are occupied by T3, fewer sites are available to bind T3-ALP conjugate. After an incubation period, the amount of T3 in the sample is inversely proportional to the amount of T3-ALP conjugate bound in the well and is directly proportional to the amount of unbound T3-ALP conjugate in the incubation solution. Accordingly, an aliquot of the incubation solution was injected into the capillary for enzyme-amplified electrophoretically mediated micro-analysis of the unbound T3-ALP conjugate to determine indirectly the quantity of T3 in the serum sample.

T3-ALP conjugate, an immunologically active species, underwent on-line enzymatic amplification and quantitation in a capillary electrophoresis format. Quantitation of T3 to the lower limits of its clinical range ($10^{-10}$M) readily was achieved by combining enzymatic amplification with laser induced fluorescence detection The T3 assay demonstrates that this methodology is applicable to more sensitive clinical assays given the control and flexibility provided by the capillary electrophoresis format and the amenability of the methods to automation.

The method of the invention described in this example may be carried out using any conventional capillary electrophoresis system, e.g., those described in the U.S. Patents incorporated by reference above and in any microfluidic system described herein. A preferred capillary electrophoresis apparatus is an A P/ACE 2050 capillary electrophoresis instrument with a Laser Module 488 argon ion laser (Beckman Instruments, Fullerton, Calif.). This system was used with a 520 nanometer (nm) bandpass filter for laser induced fluorescence ("LIF") detection. Separations were performed in the normal polarity mode with the anode on the injection side. A preferred capillary was an untreated capillary (Polymicro Technologies, Phoenix, Ariz., USA) was 35 centimeter (cm) in length (28 cm to detector and had a 50 μm inside diameter (i.d.).

Reagents, e.g., substrates, cofactors, enzymes, competitors, biorecognition compounds, biomolecules or markers may be obtained from any pharmaceutical or chemical company, e.g., Sigma Chemical Co. (St. Louis, Mo.), Aldrich (Milwaukee, Wis.), JBL Scientific (San Luis Obispo, Calif.) or Calbiochem (San Diego, Calif.). PNA monomer synthons and PNAs can be obtained from PerSeptive Biosystems, Inc. (Framingham, Mass.). In the example herein described in detail, the Microzyme Enzyme Immunoassay Test Kit for the quantitative determination of T3 in serum and the AttoPhos Alkaline Phosphatase Substrate ("AttoPhos Substrate") was purchased from Diatech Diagnostics Inc. (Boston, Mass.). Tris-Borate-Ethylenediaminetetraacetic acid ("TBE") buffer powder was obtained from Sigma Chemical Co. (St. Louis, MO) and a TBE buffer solution (pH 8.3) was prepared. Buffers were prepared with deionized, double distilled water.

T3-ALP conjugate was chosen for the T3 electrophoretically mediated micro-analysis enzyme immunoassay because of its much higher sensitivity than para-Nitrophenyl Phosphate ("pNPP"). T3-ALP converts AttoPhos Substrate, a non-fluorescent compound, into a fluorescent product as shown below.

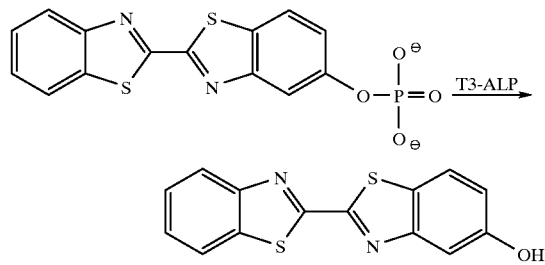

The fluorescent product is detected by laser induced fluorescence at 430 nm excitation wavelength and 560 nm emission wavelength. Because of the large Stokes shift (130 nm), the background fluorescence and light scattering significantly is reduced.

The serum sample containing T3 was added to TBE buffer in a well of a microtiter plate coated with anti-T3 monoclonal antibodies. T3 was allowed to bind to the immobilized antibodies for approximately one hour. Then a calibrated solution of T3-ALP conjugate was added to the well, the T3-ALP conjugate competing for antibody binding sites. After approximately 15 minutes, a measured aliquot of the incubated solution was injected into the capillary. The capillary and the buffer reservoirs are filled with the TBE buffer solution containing AttoPhos Substrate. The aliquot of T3-ALP conjugate from the incubation solution was injected at one end of the capillary. Generally, the assay can be performed at constant or zero potential mode. Constant potential assays are performed in a single step. After the enzyme conjugate is injected to the capillary, a constant potential is maintained until both the enzyme conjugate and product passed the detector window. Although product is continuously swept away from the enzyme conjugate, the reaction rate at which product is produced is adequately high relative to the separation time that a small amount of product accumulates. When the electrophoretic mobility of the enzyme conjugate-substrate complex is greater than that of the product, an injection peak will be evident on the electropherogram on the right hand side of the absorbance plateau as seen in FIGS. 5(A), 6(a) and 6(b).

During zero potential mode, the product is allowed to accumulate and then transported to the detector. Zero potential assays are performed in three steps: separation, incubation and product transportation. In the separation step, the injected enzyme conjugate migrates in the buffered substrate-filled capillary for a predetermined period of time under a electric field. Then power is interrupted and the product is allowed to accumulate for a fixed time in the incubation step. The product formed is then transported to the detector by reapplying potential. The profile in this mode is a peak on the top of a plateau as seen in FIG. 6(a).

Figure 17:
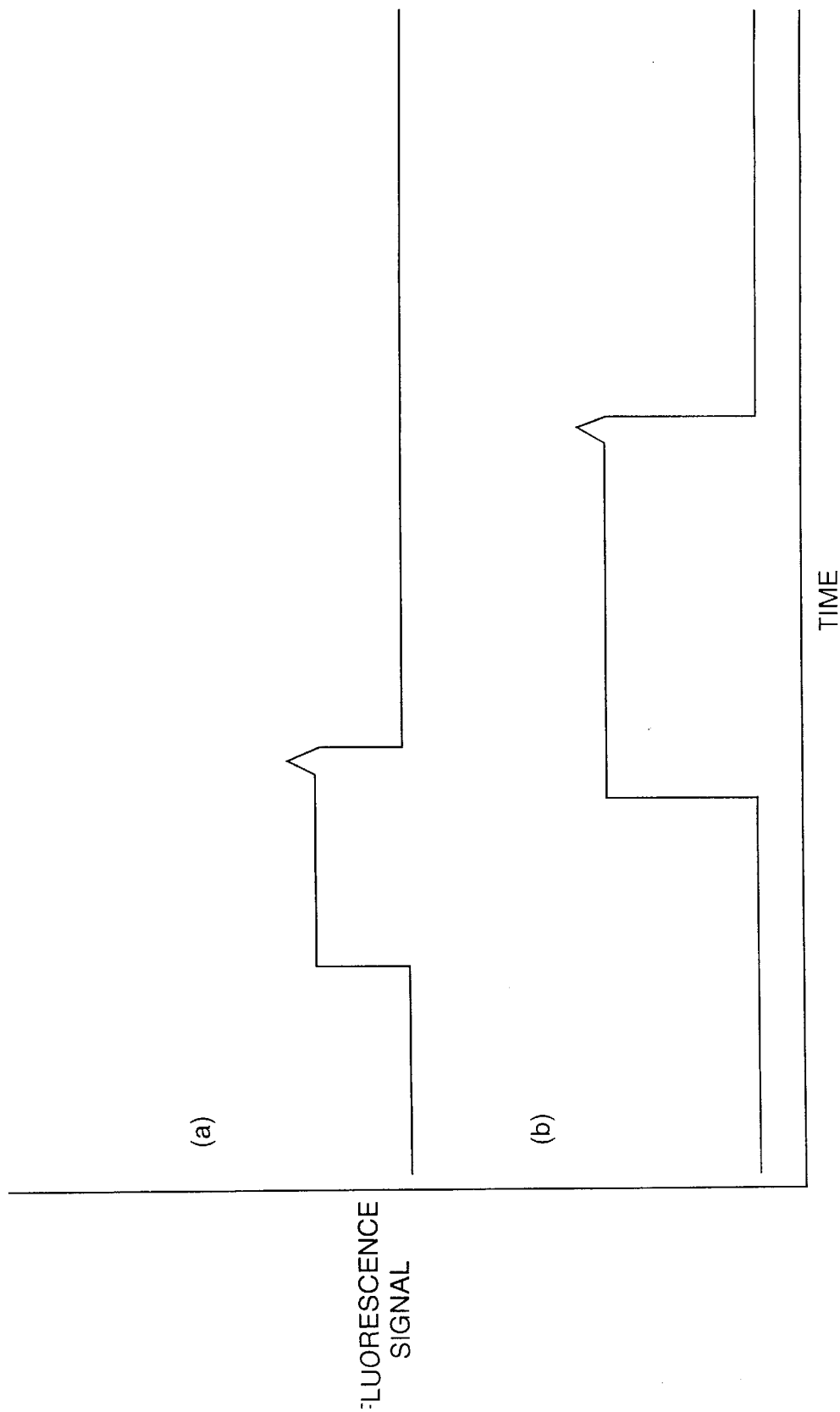
FIGS. 17: (a) and (b) show the expected electropherograms (time versus fluorescence signal) in the continuous potential mode for (a) high voltage, and (b) low voltage.

In continuous potential mode (or constant potential mode), a plateau of the fluorescent product is expected. FIGS. 17(a) and 17(b) show representative electropherograms for high and low applied voltage, respectively, in the continuous mode. As expected, the fluorescent signal increases as the applied voltage decreases. At lower applied voltage, T3-ALP conjugate moved slower in the AttosPhos Substrate-filled capillary so the contact time of the T3-ALP conjugate and the AttoPhos Substrate is increased, producing more fluorescent product as evidenced by a higher plateau (FIG. 17(b)).

Figure 18:
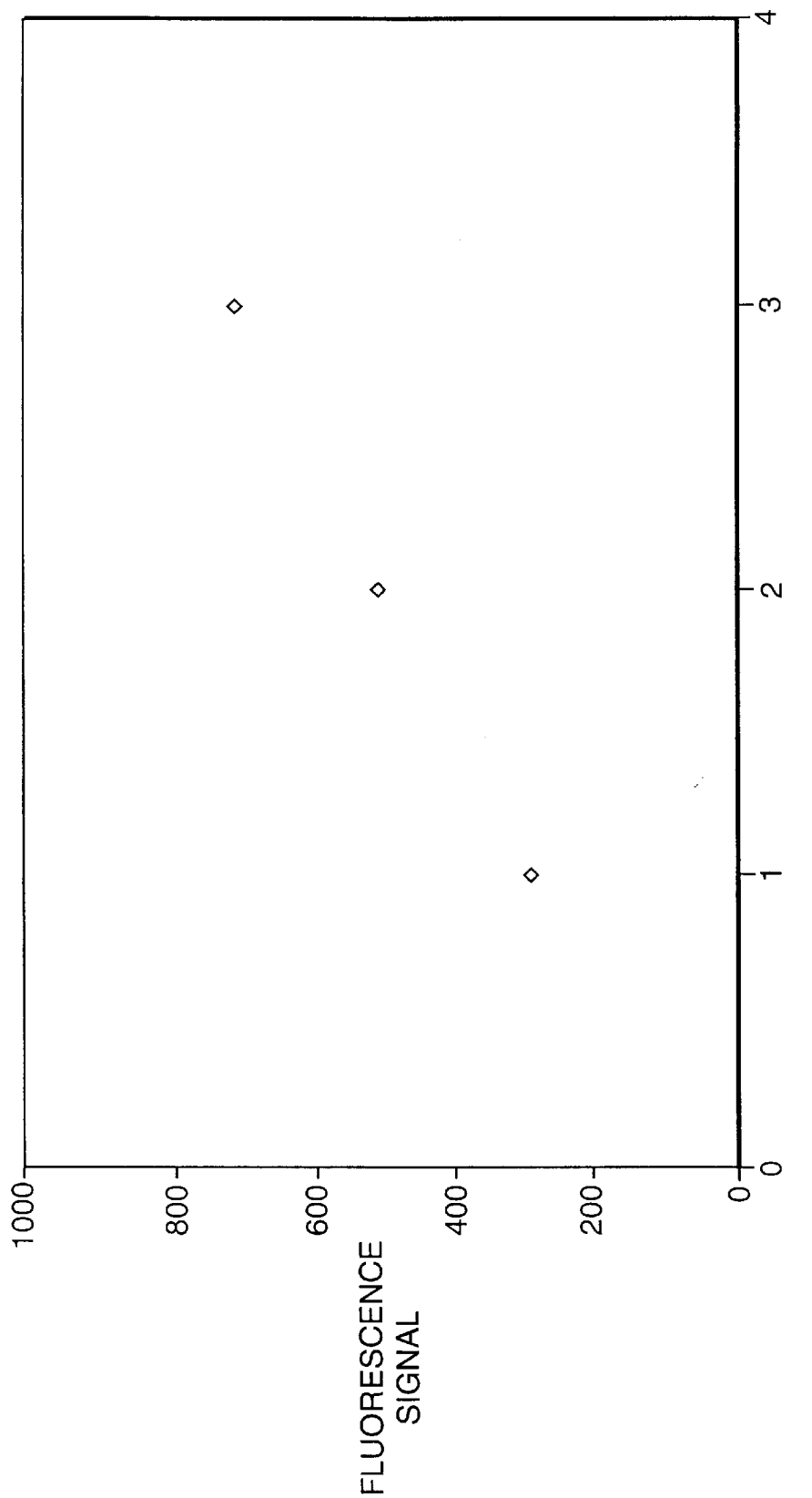
FIG. 18 is a plot of incubation time in minutes versus the fluorescence signal for the T3 electrophoretically mediated micro-analysis enzyme immunoassay.

In the zero potential mode, the fluorescent product accumulated in a the zone of the capillary where the T3-ALP conjugate stopped. Switching the potential to zero before the T3-ALP conjugate passed the detector allowed an increased incubation time and thus, increased sensitivity. That is, the amount of T3-ALP conjugate detected can be very small since the T3-ALP conjugate generates a greater amount of fluorescent product, i.e., the amount of T3-ALP conjugate is "amplified." Consequently, a very sensitive analysis is achieved. FIG. 18 shows the incubation time versus the fluorescence signal for the T3 electrophoretically mediated micro-analysis enzyme immunoassay. As expected, the greater incubation time, the greater the fluorescent signal. Since the AttoPhos Substrate was in large excess, there was a linear relationship between the incubation time and the fluorescence signal.

Figure 19:
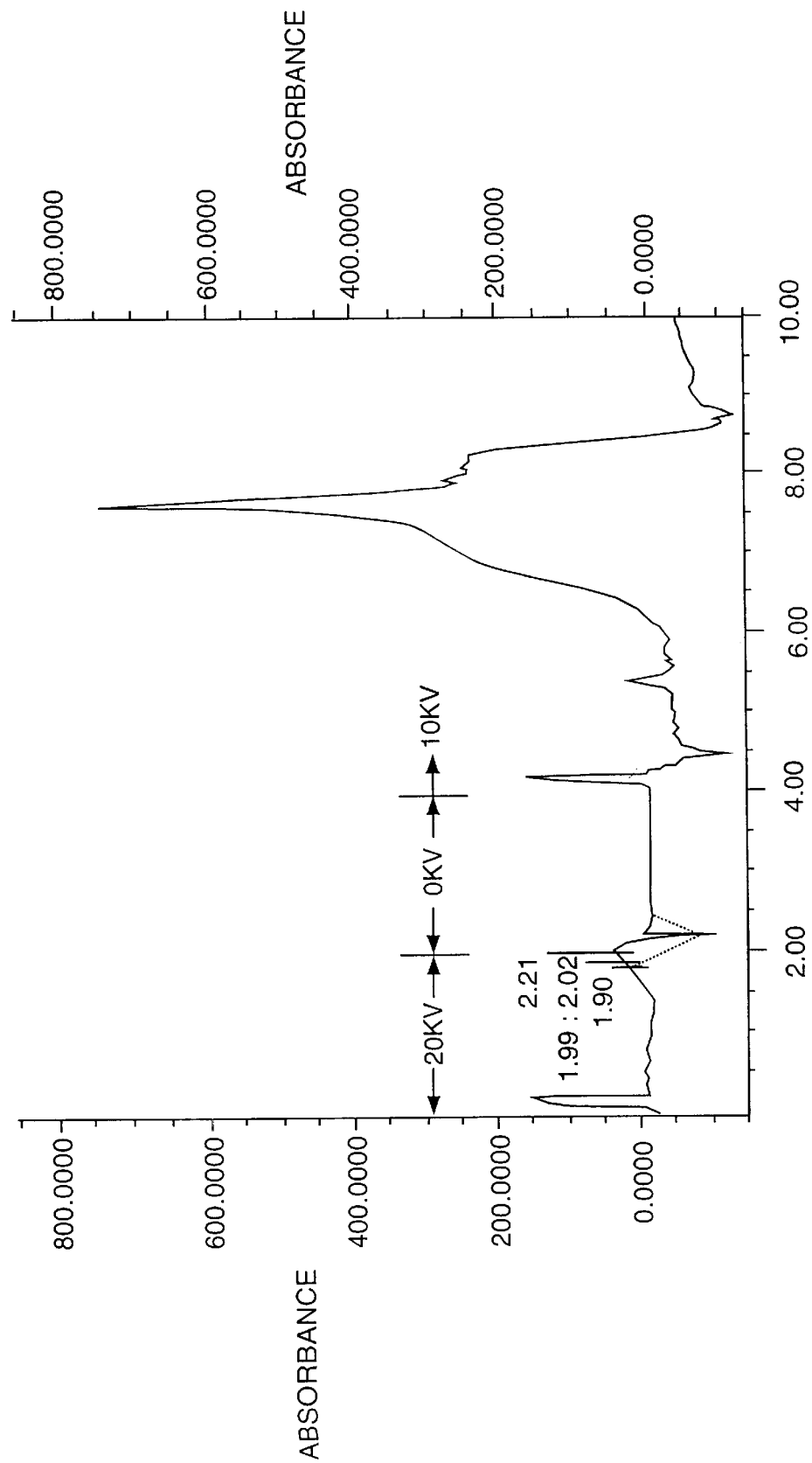
FIG. 19 shows an electropherogram conducted for the T3 electrophoretically mediated micro-analysis enzyme immunoassay using a T3 serum standard having 8.0 ng/mL of T3. An electric potential of 20 kV was applied for 2 minutes, followed by a zero potential incubation period of 2 minutes, followed by an applied electric potential of 10 kV for the remainder of the assay.

Both high and low voltage was tested in the assay. With high voltage (20 or 30 kV), the analysis time was reduced to 3 minutes without a zero potential incubation period. With low voltage (10 kV), a more stable baseline and signal were obtained even after a zero potential incubation period. The combination of high voltage (20 kV) and low voltage (10 kV) was finally determined to produce the best results (FIG. 19). The high voltage was applied before the zero potential incubation period to reduce the analysis time and low voltage was applied after the zero potential incubation period to stabilize the baseline.

The zero potential assay was carried out for a zero potential pause of 1, 2 and 3 minutes. The fluorescent signal was substantially linear for all times. The T3 electrophoretically mediated micro-analysis assay conditions were optimized so a zero potential incubation period in the capillary amplified the fluorescence signal from the product as much as possible without affecting the linearity of the signal. The optimal electrophoretically mediated micro-analysis of T3-ALP conjugate was determined to have a zero potential incubation period of 3 minutes.

Figure 20:
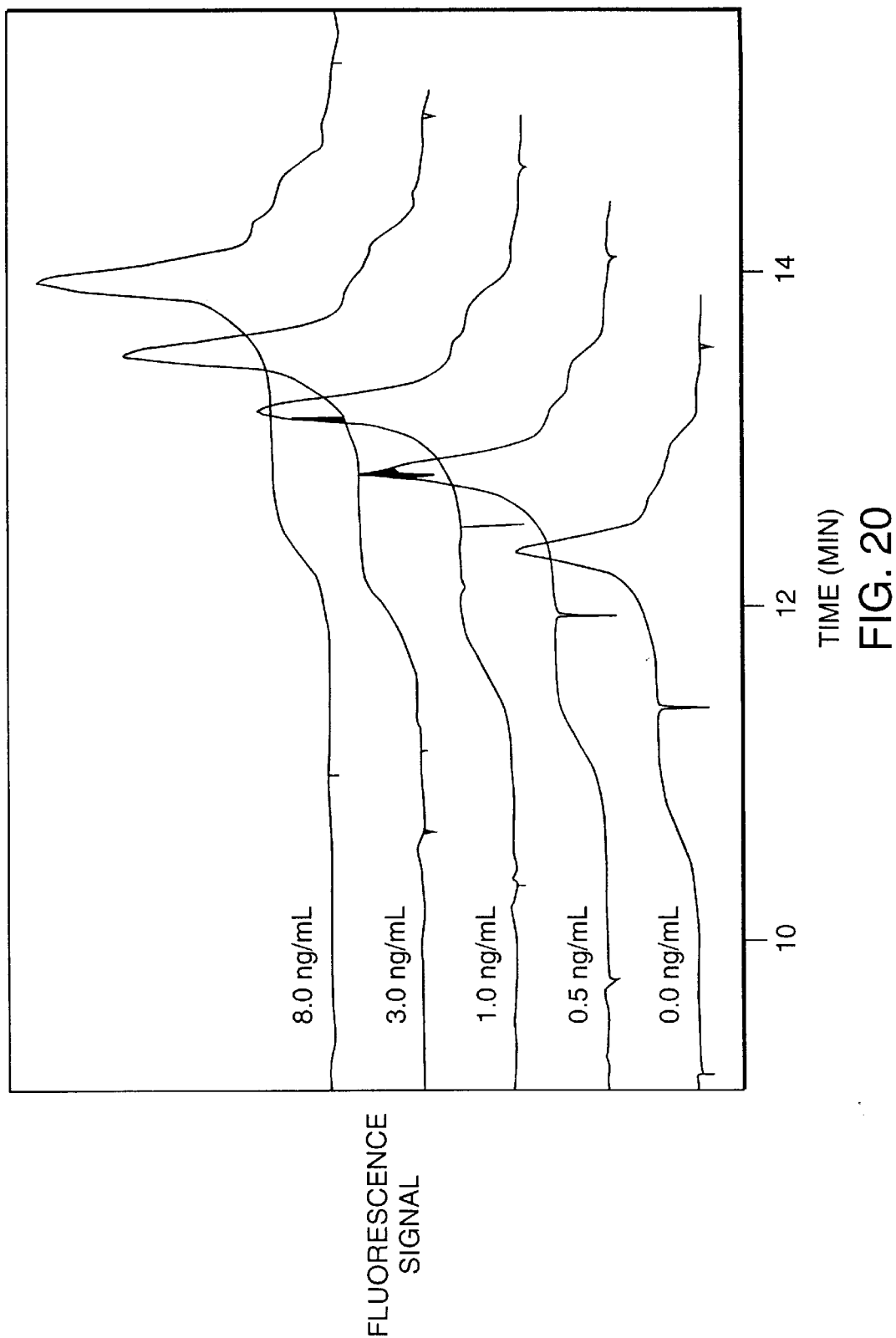
FIG. 20 shows a series of electropherograms (time versus fluorescence signal) for various known concentrations of triiodothyronine ("T3") in serum standards that were subjected to the T3 electrophoretically mediated micro-analysis enzyme immunoassay; i.e., the fluorescence signal measured is of the fluorescent product produced by T3 Alkaline Phosphatase conjugate, the amount of which is related to the amount of T3 in the original serum sample.
Figure 21:
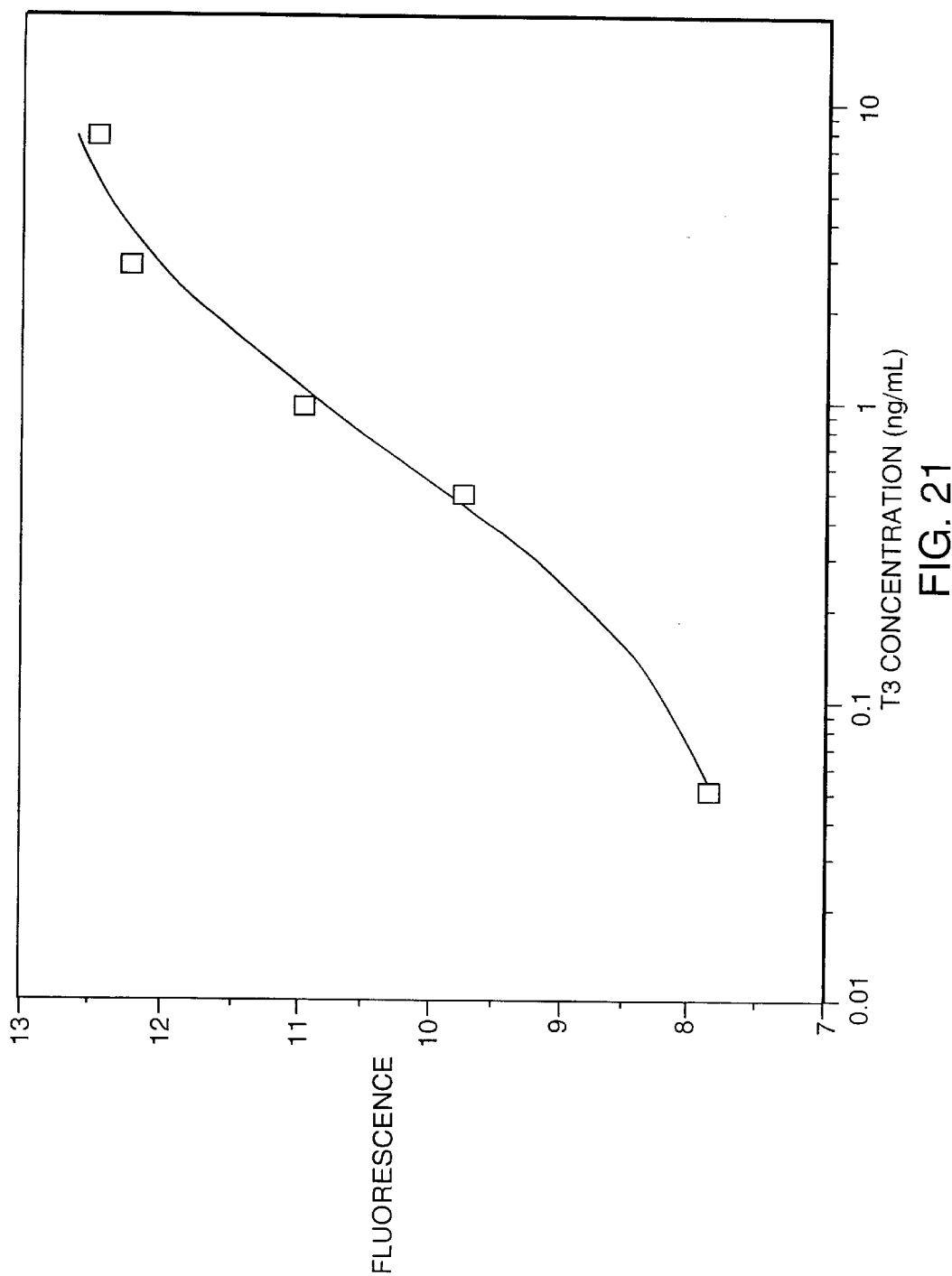
FIG. 21 is a calibration curve for the T3 electrophoretically mediated micro-analysis enzyme immunoassay in which T3 concentration (ng/mL) is plotted versus fluorescence signal.

The electropherograms in FIG. 20 are of various known concentrations of T3 serum standards that were subjected to the immunological reaction with T3-ALP conjugate and capillary electrophoresis micro-analysis using the optimal conditions described above. The fluorescence signal of the product produced from the unbound T3-ALP conjugate was measured for each concentration of T3 subjected to the competitive reaction with the T3-ALP conjugate. Under the same experimental conditions, the correlation between the amount of product detected and the amount of T3 in the serum standards permitted a calibration curve to be constructed (FIG. 21). Quantitation was based on determinations of the peak height above the constant potential product plateau in the electropherogram. The peak area above the constant potential product plateau also can be used to determine the amount of product formed.

The amount of unbound T3-ALP conjugate is proportional to the amount of T3 present in a sample. In the T3 electrophoretically mediated micro-analysis enzyme immunoassay, the amount of unbound T3-ALP conjugate quantitatively was determined by measurement of the fluorescent product so the amount of T3 in the original sample could be calculated. A calibration curve was constructed using a known amount of T3 under a given set of experimental conditions to determine the fluorescence signal the results. Using the same relationships, under the same set of experimental conditions, an unknown amount of T3 in a sample can be quantitatively determined using the constructed calibration curve.

The results indicate that the variation of the signals for is not related to the electrophoretically mediated micro-analysis technique. Possible sources for the variation of the signal may be non-specific binding of the free ALP and/or T3-ALP conjugate to the microplate wall, variation in the incubation time of the serum standards and a high free ALP concentration that disrupts the background.

Other embodiments are within the following claims.

What is claimed is:

1. A method for performing an assay comprising:
   (a) introducing a first reactant and a sample containing an analyte into a channel containing an electrophoresis medium,
   wherein the analyte comprises or is complexed to a competitor, said competitor comprising a biorecognition portion and a second reactant portion;
   (b) applying an electric potential along the length of the channel to cause said first reactant and said second reactant portion of said competitor to form or deplete a detectable product;
   (c) imposing along the length of said channel an electric potential sufficient to cause said detectable product to be separated from said first reactant by differential migration along said channel; and
   (d) detecting said detectable product.

2. The method of claim 1 comprising the additional step of:
  (e) quantitatively determining the amount of said detectable product formed or depleted in said channel.

3. The method of claim 1 wherein one of said first reactant or said second reactant portion comprises an enzyme and the other of said first reactant or said second reactant portion comprises an enzyme substrate.

4. The method of claim 1 comprising the additional steps before step (a) of:
  (i) contacting an immobilized reactant and an analyte in a solution;
  (ii) adding to said solution said competitor; and
  (iii) using an aliquot of said solution, said aliquot defining said sample.

5. The method of claim 4 wherein said immobilized reactant is an immobilized antibody.

6. The method of claim 1 wherein said sample is the result of an immunological reaction.

7. The method of claim 6 wherein said immunological reaction is a competitive reaction.

8. The method of claim 1 wherein the analyte is charged.

9. The method of claim 1 wherein the analyte is complexed to the competitor which defines an analyte-competitor complex, and the analyte-competitor complex comprises a charge modifier.

10. The method of claim 1 wherein said biorecognition portion is selected from the group consisting of antibodies, antigens, enzymes, peptides, peptide nucleic acids, oligonucleotides, deoxyribonucleic acids, ribonucleic acids, biotins and their complementary binding complexes, lectins and their complementary carbohydrate binding complexes, and cellular receptor binding proteins and their complementary binding products.

11. The method of claim 1 wherein said channel used in step (a) contains said first reactant prior to the introduction of said sample.

12. The method of claim 1 including the additional step of:
  subjecting said channel to zero potential by removing said electric potential after contact between said competitor and said first reactant for a time sufficient to allow said detectable product to form or to deplete.

13. The method of claim 12 further comprising, after said step of subjecting said channel to zero potential, and, the step of:
  re-imposing along the length of said channel said electric potential for a time sufficient to allow said detectable product to migrate in said channel.

14. The method of claim 1 wherein said sample comprises one or more competitors comprising different biorecognition portions.

15. The method of claim 14 wherein one or more first reactants are introduced into said channel.

16. The method of claim 15 wherein plural detectable products are formed or depleted.

17. A method for performing an assay, said method comprising:
  (a) conducting a heterogeneous competitive reaction in a vessel among an immobilized reactant, an analyte, and a competitor, wherein the competitor comprises a biorecognition portion and a second reactant portion;
  (b) introducing an aliquot of the competitor which is unbound in step (a) into a channel containing an electrophoresis medium and a first reactant;
  (c) imposing an electrical potential along the length of the channel to cause, the second reactant portion of the competitor and the first reactant to form or deplete a detectable product within the channel; and
  (d) detecting the detectable product.

18. The method of claim 17 comprising the additional step of:
  (e) quantitatively determining the amount of said detectable product formed or depleted in said channel.

19. The method of claim 17 wherein one of said first reactant or said second reactant portion comprises an enzyme and the other of said first reactant or said second reactant portion comprises an enzyme substrate.

20. The method of claim 17 wherein said biorecognition portion is selected from the group consisting of antibodies, antigens, enzymes, peptides, peptide nucleic acids, oligonucleotides, deoxyribonucleic acids, ribonucleic acids, biotins and their complementary binding complexes, lectins and their complementary carbohydrate binding complexes, and cellular receptor binding proteins and their complementary binding products.

21. The method of claim 17 wherein said immobilized reactant is an immobilized antibody.

22. The method of claim 17 wherein said channel used in step (b) contains said first reactant prior to the introduction of said aliquot.

23. The method of claim 17 including the additional step of:
  subjecting said channel to zero potential by removing said electric potential after contact between said competitor and said first reactant for a time sufficient to allow said detectable product to form or to deplete.

24. The method of claim 23 further comprising, after said step of subjecting said channel to zero potential, and the step of:
  re-imposing along the length of said channel said electric potential for a time sufficient to allow said detectable product to migrate in said channel.

25. An analytical device comprising a capillary zone electrophoresis channel, said channel comprising:
  a free solution electrophoretic medium,
  a first reactant in said electrophoretic medium that will react in said channel with a second reactant portion of a competitor to form or deplete a detectable product wherein the competitor further comprises a biorecognition portion; and
  said analytical device further comprising electrical power means for applying a field across the ends of said channel to cause said first reactant and said second reactant portion of said competitor to migrate and react.

26. The device of claim 25 further comprising a detector for detecting said detectable product.

27. The device of claim 26 further comprising a quantitator for quantitatively determining the amount of said detectable product detected.

28. The device of claim 25 wherein said channel is a capillary.

29. The device of claim 25 wherein said competitor and said first reactant are spaced apart within said channel such that, upon the application of an electric field along the length of said channel by said electrophoresis apparatus, said competitor or said first reactant migrates in said channel to permit said first reactant to react with said second reactant portion of said competitor to form or deplete said detectable product.

* * * * *